United States Patent
Shaw

(10) Patent No.: US 11,152,198 B2
(45) Date of Patent: Oct. 19, 2021

(54) DIRECT DETERMINATION OF ANTIBODY CHAIN PAIRING

(71) Applicant: Battelle Memorial Institute, Richland, WA (US)

(72) Inventor: Jared B. Shaw, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 150 days.

(21) Appl. No.: 16/782,705

(22) Filed: Feb. 5, 2020

(65) Prior Publication Data

US 2020/0251318 A1 Aug. 6, 2020

Related U.S. Application Data

(60) Provisional application No. 62/801,514, filed on Feb. 5, 2019.

(51) Int. Cl.
*H01J 49/00* (2006.01)
*G01N 33/68* (2006.01)

(52) U.S. Cl.
CPC ...... *H01J 49/0036* (2013.01); *G01N 33/6857* (2013.01); *H01J 49/0054* (2013.01); *H01J 49/0059* (2013.01)

(58) Field of Classification Search
CPC ............. H01J 49/0036; H01J 49/0054; H01J 49/0059; G01N 33/6857
USPC .............. 250/281, 282, 283, 287, 288
See application file for complete search history.

(56) References Cited

U.S. PATENT DOCUMENTS

| | | | | |
|---|---|---|---|---|
| 5,236,825 A | * | 8/1993 | Iverson | C07K 14/705 435/68.1 |
| 2003/0130485 A1 | * | 7/2003 | Meyers | C12N 9/0004 530/350 |
| 2008/0318213 A1 | * | 12/2008 | Denny | G16B 40/10 435/6.12 |

* cited by examiner

*Primary Examiner* — Nicole M Ippolito
(74) *Attorney, Agent, or Firm* — Klarquist Sparkman, LLP

(57) ABSTRACT

Methods are described for using a combination of mass spectroscopic and proteomic approaches for identifying the specific pairing of heavy and light chains for an intact antibody, an antibody fragment, a mixture of intact antibodies, or a mixture of antibody fragments.

21 Claims, 17 Drawing Sheets
(12 of 17 Drawing Sheet(s) Filed in Color)

FIG. 1
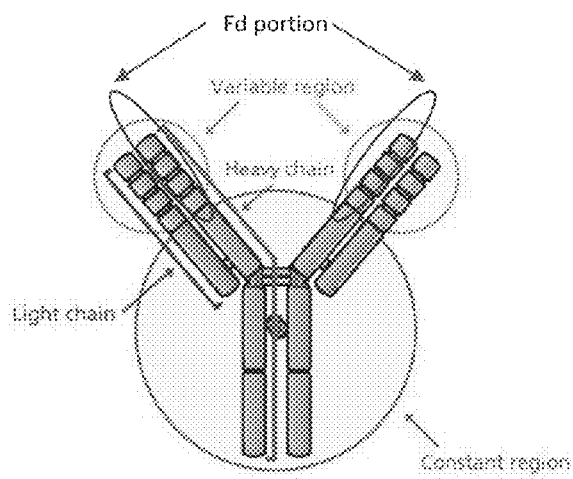
- Combination of intact masses
  - Light chain
  - Heavy chain or Fd
  - Intact mAb, Fab, F(ab')$_2$
- Sequence information unique to the mAb
  - Complementarity determining regions (CDR)
IgG1 variable region disulfide bonds

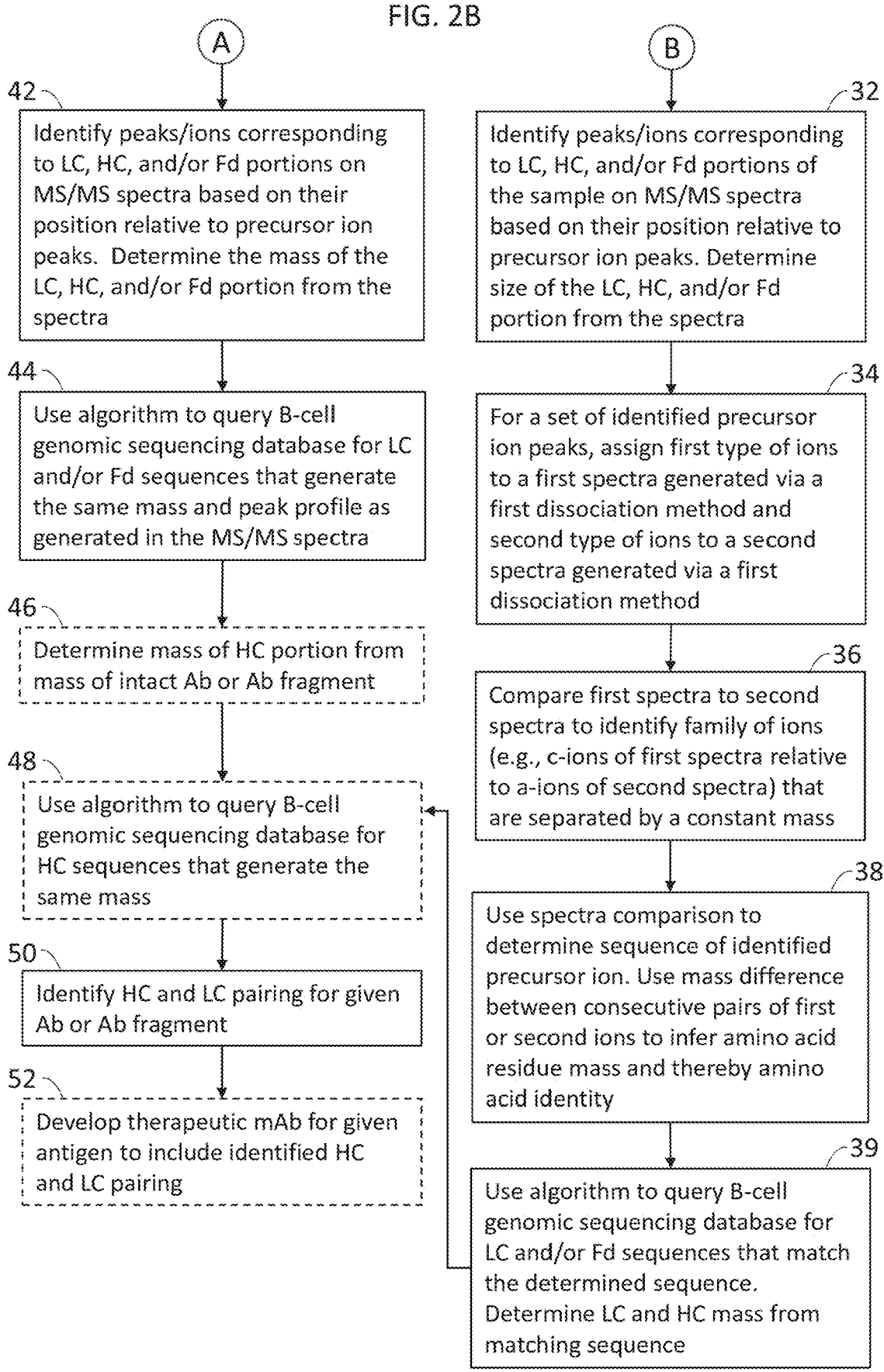

Characteristic mass differences of ion series for de novo sequencing:
a and c-ions = 45.0215
a and b-ions = 27.9949
c and b-ions = 17.0267

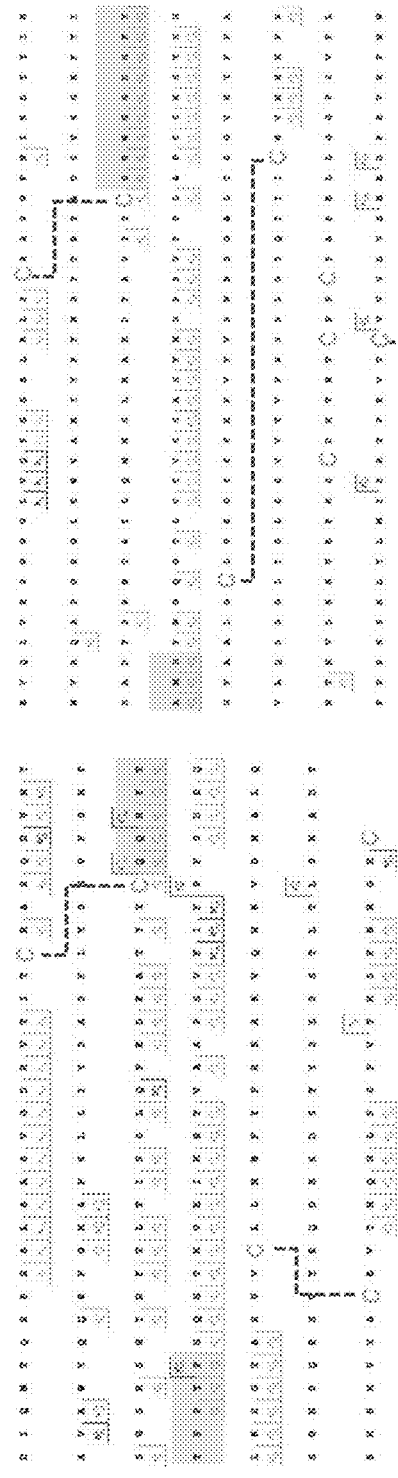
FIG. 5A) Light chain: 42% sequence coverage
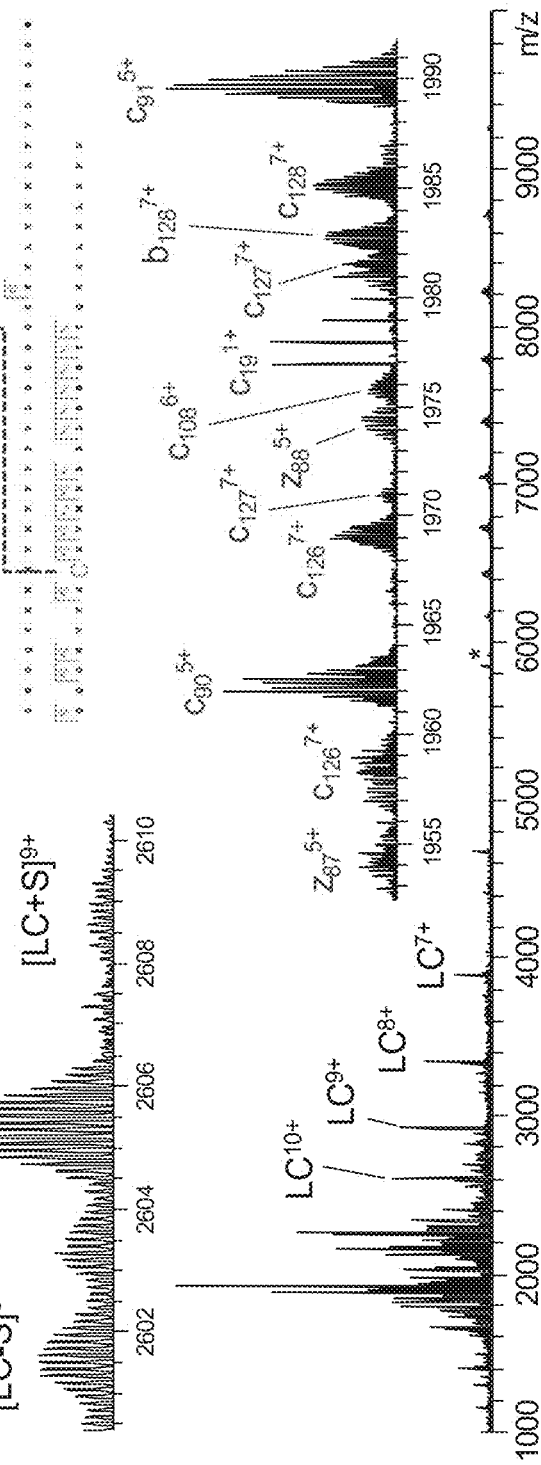
FIG. 5B) Heavy chain: 20% sequence coverage
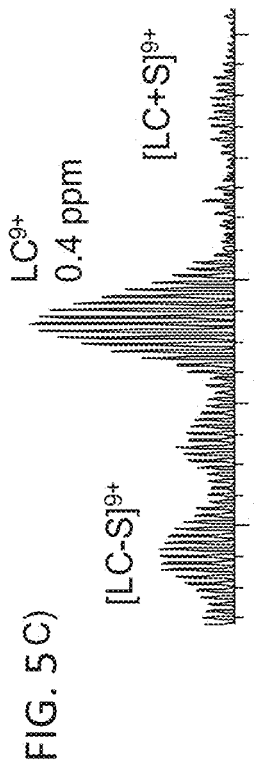
FIG. 5C)

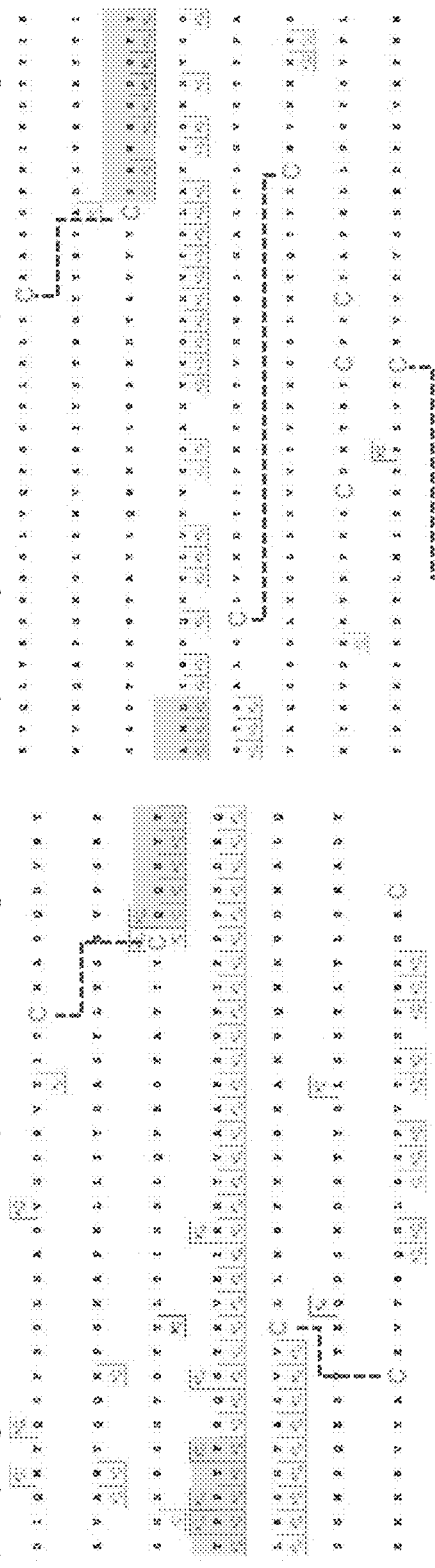
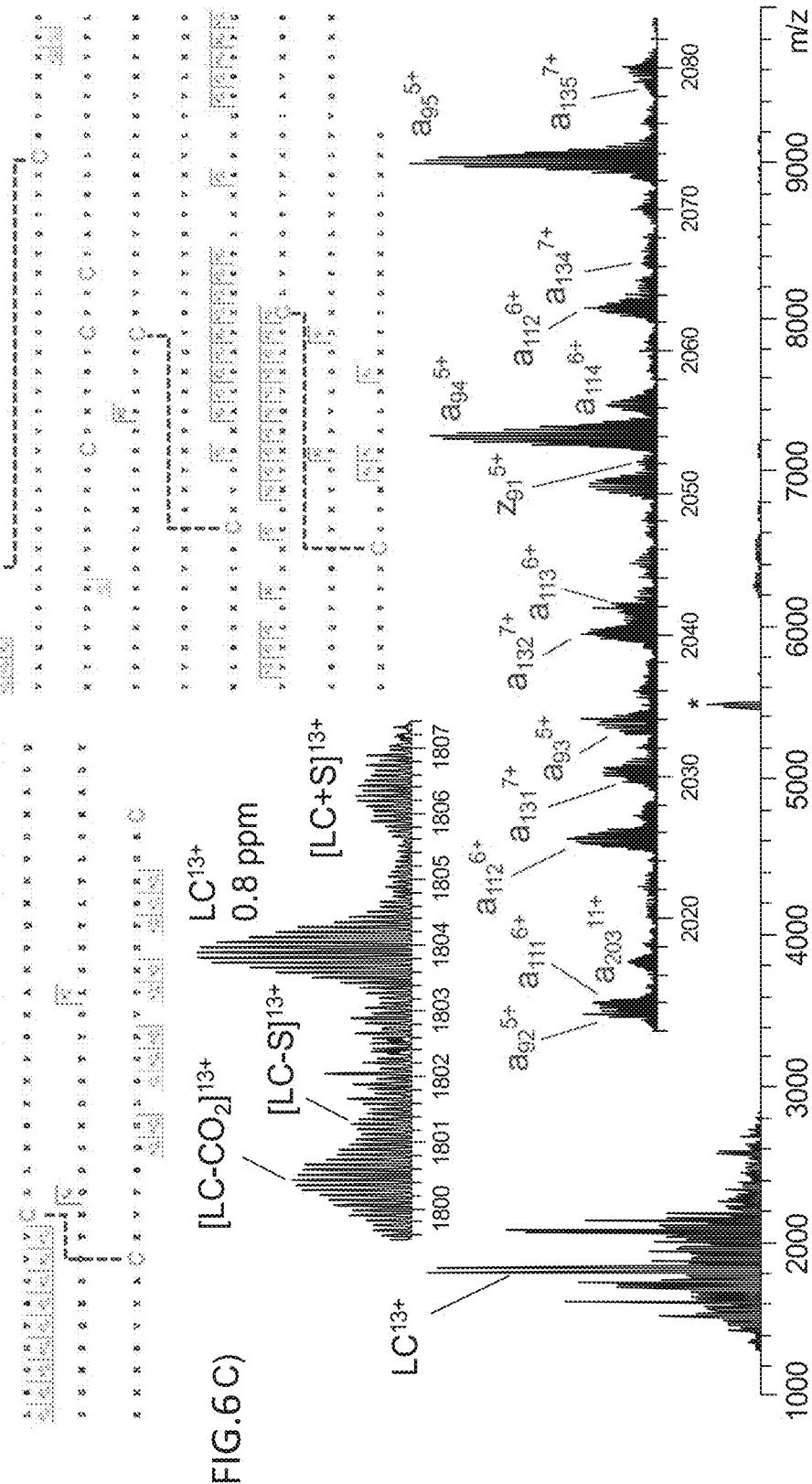
FIG. 6 A) Light chain: 32% sequence coverage  FIG. 6B) Heavy chain: 17% sequence coverage
FIG. 6C)

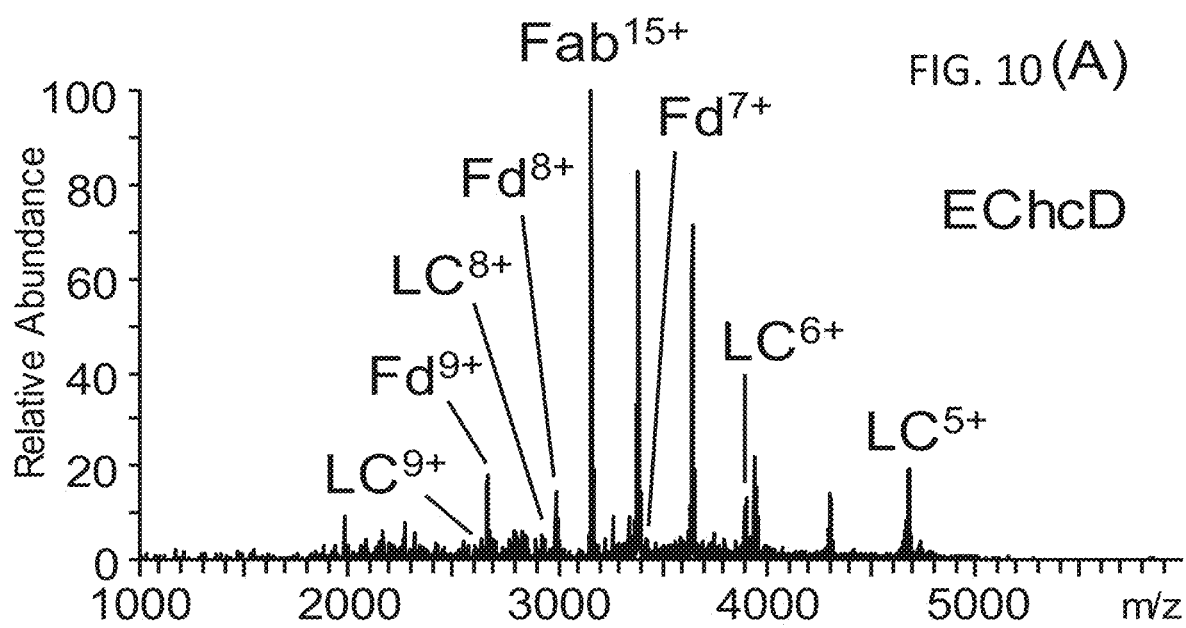
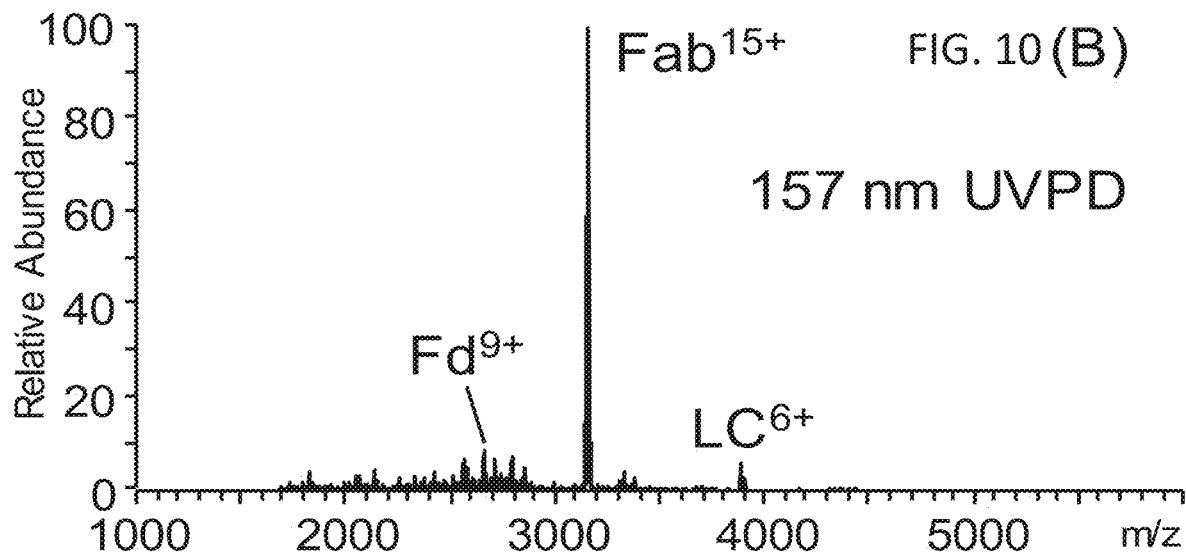

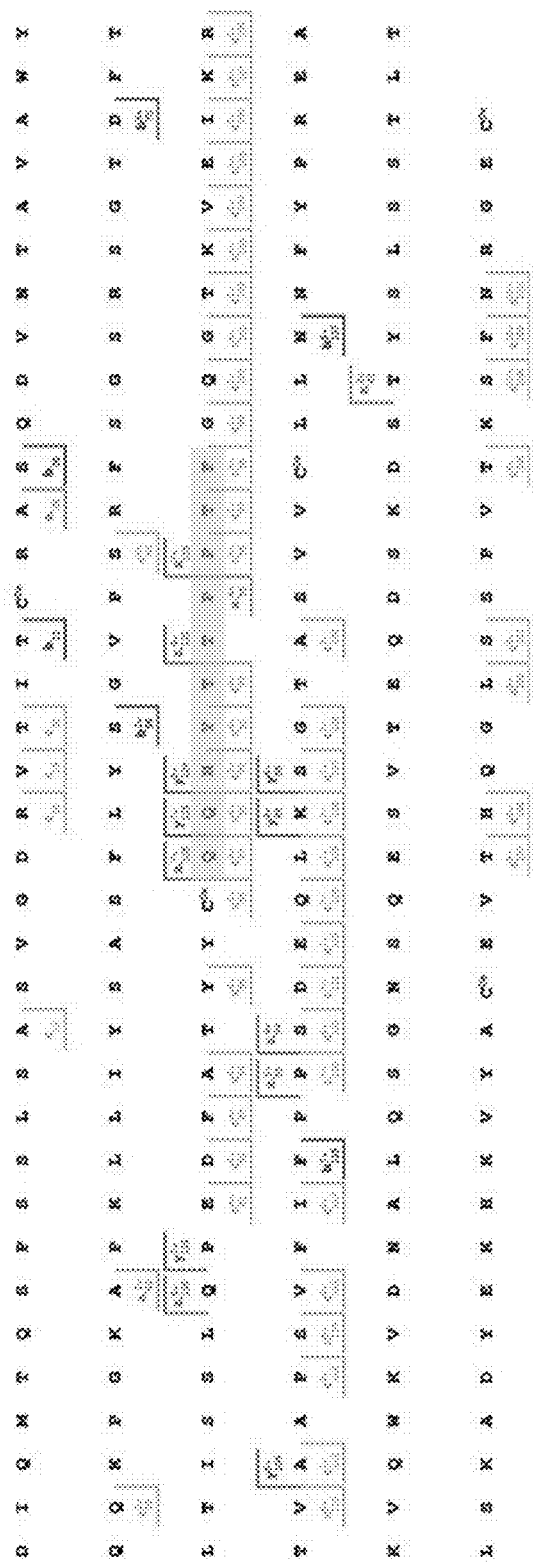
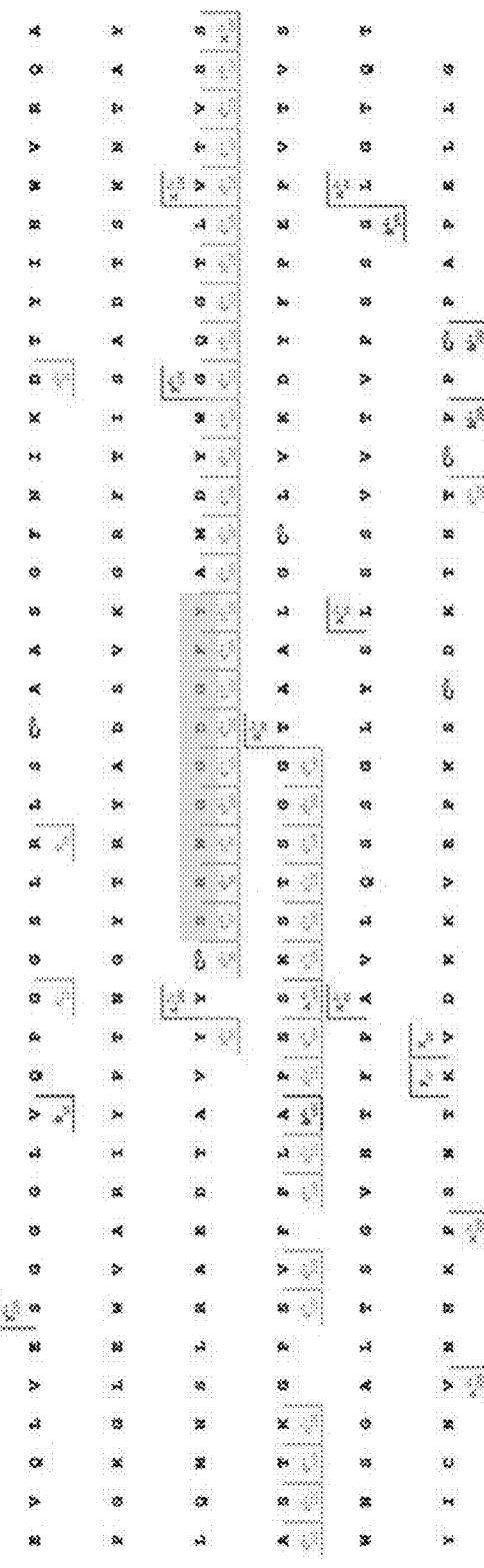
FIG. 11A
FIG. 11B

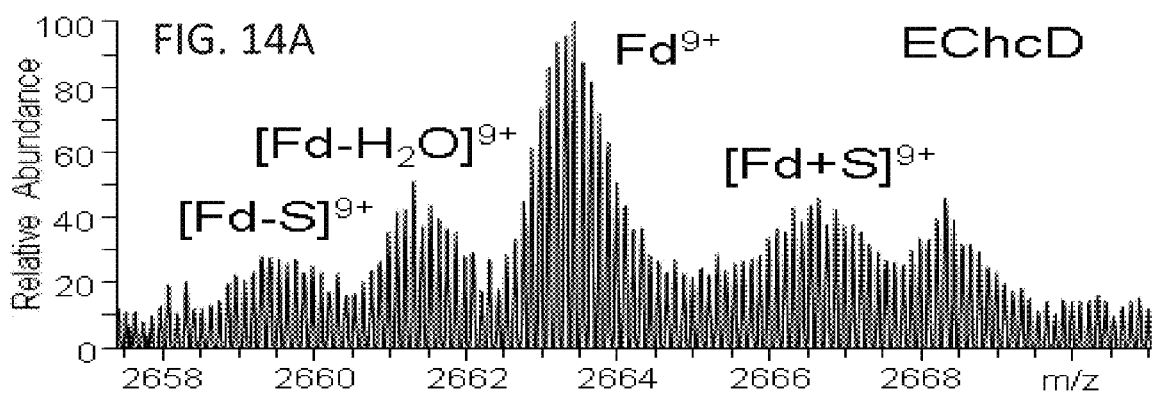
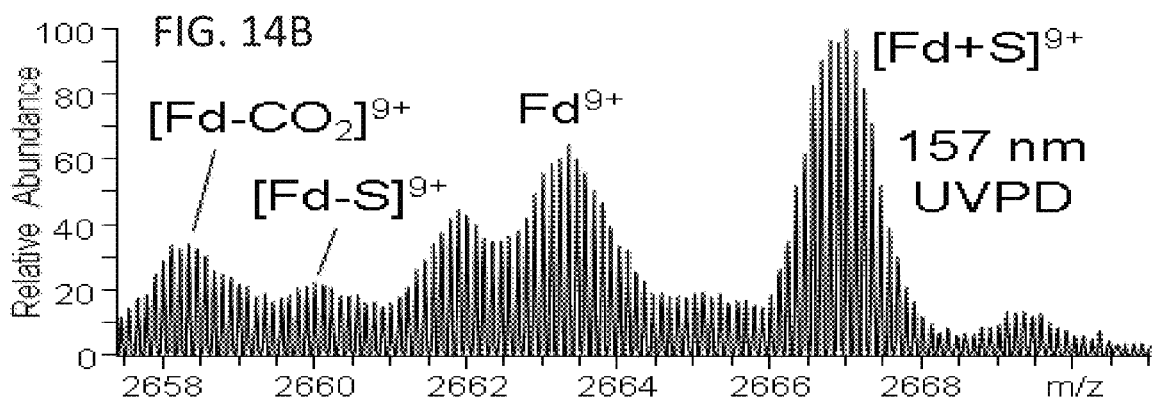
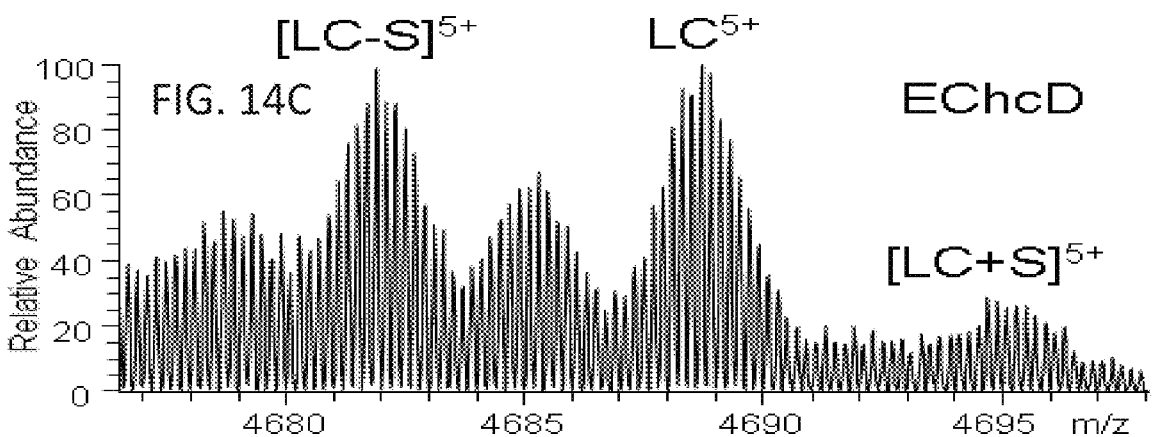
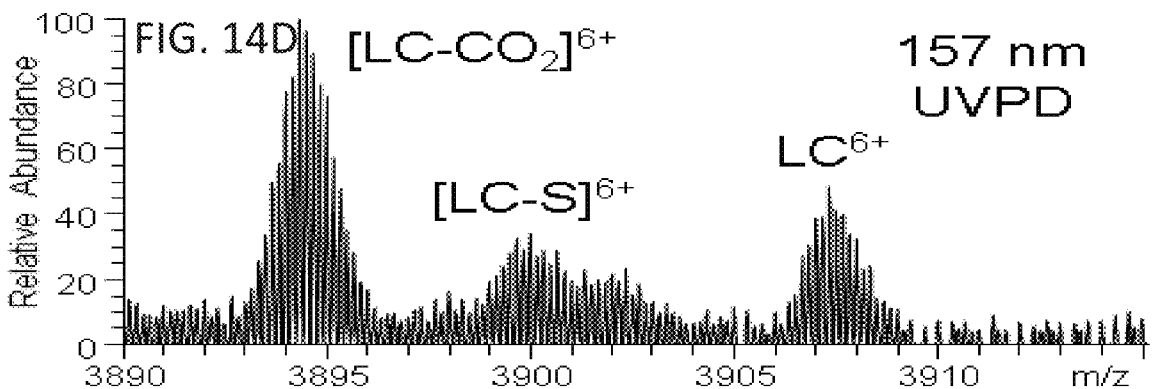

GingisKHAN digest of 13 mAbs
Targeted online analysis of Fab fragments

GingisKHAN digest of 13 mAbs
Targeted online analysis of Fab fragments

DIRECT DETERMINATION OF ANTIBODY CHAIN PAIRING

CROSS REFERENCE TO RELATED APPLICATION

This application claims priority to U.S. Provisional Application No. 62/801,514 filed Feb. 5, 2019, herein incorporated by reference in its entirety.

ACKNOWLEDGMENT OF GOVERNMENT SUPPORT

This invention was made with government support under Contract DE-AC0576RLO1830 awarded by the U.S. Department of Energy and under R43GM122131-01 and R44GM122131-02 awarded by the National Institutes of Health. The government has certain rights in the invention.

FIELD

The present disclosure provides methods that use mass spectroscopy and proteomic analyses for the direct determination of antibody chain pairing. Such methods can be used to determine the specific pairing of a light chain (LC) and a heavy chain (HC) of an antibody.

BACKGROUND

Monoclonal antibody (mAb) therapeutics are the basis of treatment for many illnesses ranging from viral pathogens to various forms of cancer. To be prepared as new threats emerge and novel immuno-oncology targets are identified, rapid vaccine testing and mAb discovery capabilities are critical. One method for interrogation of the polyclonal antibody (pAb) response and discovery of potent human mAbs is isolation of peripheral B cells from survivors/seropositive individuals for single B-cell sequencing [1] and/or hybridoma generation [2]. These methods rely on DNA sequencing and/or tandem mass spectrometry (MS/MS) de novo sequencing [3-7] to determine the primary amino acid (AA) sequence of individual heavy chain (HC) and light chain (LC) mAb protein subunits. It is common to find multiple mAbs from the same host sharing the same HC or LC, making structural HC/LC pairing crucial. Even hybridoma cell lines, which are typically thought to be monoclonal, can produce multiple ambiguous HC/LC pairs with frequency >30% [8].

The absence of effective pairing in existing mAb sequencing strategies limits analysis to isolated B cell colonies that each produce a single mAb (where there is only one possible pair of HC/LC), or necessitates the use of B-cell-sorting techniques. This limitation is profound particularly when interrogating the complex pAb response. It is estimated that at most 2% of all pAbs are expressed by peripheral serum B cells (compared to B cells in all tissues including spleen, bone marrow, and lymph nodes), of which only a fraction may be retained following single-cell sorting or hybridoma fusion [9].

Mass spectrometry (MS) based de novo structure characterization of antibodies has the potential to greatly reduce reliance on B cell sequencing and hybridoma methods for antibody discovery. Bottom-up proteomics based de novo sequencing methods have advanced significantly in recent years due to developments in MS instrumentation, methodology, and informatics approaches. However, HC and LC pairing information is lost in the bottom-up approach.

Top-down and middle-down approaches have the potential to reduce peptide assembly and eliminate chain pairing challenges associated with bottom-up proteomics methods. Top-down and middle-down de novo sequencing approaches are under development [10-14]; however, the direct determination of antibody chain pairing at the intact mAb, $F(ab')_2$, or Fab levels poses challenges. These challenges are predominantly associated with sequence coverage limitations imposed by intramolecular disulfide bonds and intermolecular disulfide bonds that prevent separation of the intact chains as well as chain fragments during MS/MS experiments. Middle-down analyses utilizing branched product ions (i.e., product ions containing a portion of the HC and LC linked by a disulfide bond) from the Fab fragment of Trastuzumab have demonstrated the potential to determine chain pairing from multiplexed MS/MS spectra [15]. However, this approach may be limited for antibody mixtures due to the large number of possible branched product ions which could reduce confidence in identification. A complementary method for determination of chain pairing is needed.

A wide variety of MS/MS methods have been used to cleave disulfide bonds in both polypeptide cations and anions with varying degrees of efficiency and specificity [16-27]. The common themes among these methods are the use of high energy photons (i.e., UV or vacuum-UV wavelengths) and ion-electron or ion-ion reactions to induce disulfide bond cleavage. Ultraviolet photodissociation (UVPD) using UV and VUV photons yields homolytic cleavage of the disulfide bond from an excited electronic state. UV photons generally provide greater specificity for disulfide bond cleavage, and VUV photons yield polypeptide backbone fragments as well as disulfide bond cleavage. On the other hand, the mechanism and specificity of electron-based methods, such as electron capture dissociation (ECD) and electron transfer dissociation (ETD), for disulfide bond cleavage has been debated [18, 28]. High energy collision induced dissociation and matrix assisted laser desorption ionization with in-source decay have been demonstrated to cleave disulfide bonds, but instrumentation with these capabilities is not frequently used in modern proteomics analyses. Although not an MS/MS based method, online electro-chemical reduction of interchain disulfides is another method for rapid separation of heavy and light chains.

Top-down analysis of mAbs under denaturing conditions using ECD and ETD have been reported. Polypeptide backbone cleavage product ions within di-sulfide bridges of the LC and HC were observed, but intact HC and LC ions were not reported. This is most likely due to secondary electron capture/transfer events by highly charge product ions (e.g., intact LC or HC) that undergo further fragmentation.

SUMMARY

Herein, a new methodology is disclosed for direct determination of antibody chain pairing using top-down and middle-down proteomics approaches. The method provides for efficient cleavage of disulfide bonds to enable accurate mass measurement of intact chain or subunit masses. Further, the method yields chain specific product ions. Furthermore, the methods disclosed herein enable complete sequence coverage of a CDR region of an antibody to be determined, which provides a unique sequence tag for each chain. The approach provides a unique top-down/middle-down characterization of mAb, pAb, Fab, and $F(ab')_2$ from native like charge states using cleavage methods such as ECD and UVPD. More generally, the approach demonstrates disulfide bond cleavage and separation of protein subunits in a large native protein complex.

Provided herein are methods of determining chain pairing of an intact antibody. In some examples, the methods include ionizing the intact antibody into precursor ions; determining a mass of the intact antibody from a mass spectrum of the precursor ions; selecting one or more precursor ions for MS/MS analysis; dissociating by a first dissociation method, a light chain of the intact antibody from a heavy chain of the intact antibody to generate a first type of product ions of the light chain and produce a first mass spectrum of the light chain; and dissociating by a second dissociation method, the light chain of the intact antibody from the heavy chain of the intact antibody to generate a second type of product ions of the light chain and produce a second mass spectrum of the light chain, wherein the first dissociation method cleaves a backbone of the light chain at a different location than the second dissociation method. The method can further include comparing the first mass spectrum to the second mass spectrum to identify a first group of the first type of product ions that differ in mass from a second group of the second type of product ions by a constant value; determining an amino acid sequence of the light chain based on a mass difference between consecutive product ions of the first group and/or consecutive product ions of the second group; determining a mass of the light chain from the first or second mass spectrum; determining a mass of the heavy chain of the intact antibody based on the mass of the intact antibody and the mass of the light chain; comparing the determined sequence of the light chain and the mass of the heavy chain with a database containing amino acid sequences of light chain sequences and heavy chain sequences; and determining heavy chain and light chain pairing of the intact antibody or antibody fragment.

Also provided are methods of determining chain pairing of an antibody fragment, such as an Fab or F(ab')$_2$ fragment. Such methods can include ionizing the antibody fragment into precursor ions; determining a mass of the antibody fragment from a mass spectrum of the precursor ions; selecting one or more precursor ions for MS/MS analysis; dissociating by a first dissociation method, a light chain of the antibody fragment from an Fd portion of the antibody fragment to generate a first type of product ions of the light chain and a first mass spectrum of the light chain, and a first type of product ions of the Fd portion and a first mass spectrum of the Fd portion, wherein the Fd portion is derived from a heavy chain; dissociating by a second dissociation method, the light chain of the antibody fragment from the Fd portion of the antibody fragment to generate a second type of product ions of the LC chain and a second mass spectrum of the LC chain, and a second type of product ions of the Fd portion and a second mass spectrum of the Fd portion, wherein the first dissociation method cleaves a backbone of the Fd portion at a different location than the second dissociation method. The method can further include comparing the first mass spectrum of the light chain to the second mass spectrum of the light chain to identify a first group of the first type of product ions that differ in mass from a second group of the second type of product ions by a constant value; comparing the first mass spectrum of the Fd portion to the second mass spectrum of the Fd portion to identify a first group of the first type of product ions that differ in mass from a second group of the second type of product ions by a constant value; determining, from the first and/or second mass spectrum of the light chain, an amino acid sequence of the light chain based on a mass difference between consecutive product ions of the first group and/or consecutive product ions of the second group; determining an amino acid sequence of the light chain based on a mass difference between consecutive product ions of the first group and/or consecutive product ions of the second group; determining, from the first and/or second mass spectrum of the Fd portion, an amino acid sequence of the Fd portion based on a mass difference between consecutive product ions of the first group and/or consecutive product ions of the second group; and determining an amino acid sequence of the Fd portion based on a mass difference between consecutive product ions of the first group and/or consecutive product ions of the second group. The method can further include comparing the determined sequence of the light chain and Fd portion with a database containing amino acid sequences of light chain sequences and heavy chain sequences; and determining heavy chain and light chain pairing of the antibody fragment.

In another example of determining chain pairing, the methods include ionizing an intact antibody or antibody fragment into precursor ions; determining a mass of the intact antibody or a mass of the antibody fragment from a mass spectroscopy spectrum of the precursor ions; selecting one or more precursor ions for MS/MS analysis; dissociating at least a light chain from the intact antibody by cleaving one or more disulfide bonds linking a heavy chain and the light chain of the intact antibody, or dissociating an intact light chain and a heavy chain fragment from the antibody fragment by cleaving disulfide bonds linking the heavy chain fragment and the light chain of the antibody fragment. The method can further include determining a mass of the light chain of the intact antibody from a mass spectroscopy spectrum of a product ion of the light chain of the intact antibody, or determining a mass of the light chain of the antibody fragment from a mass spectroscopy spectrum of a product ion of the light chain of the antibody fragment and determining a mass of the heavy chain fragment from a mass spectroscopy spectrum of a product ion of the heavy chain fragment of the antibody fragment; and comparing the identified mass of the light chain and the mass of the intact antibody with a database comprising amino acid sequences of light chain sequences and heavy chain sequences or comparing the identified mass of the light chain and the mass of the heavy chain fragment with a database comprising amino acid sequences of light chain sequences and heavy chain sequences. The method can further include determining heavy chain and light chain pairing of the intact antibody or antibody fragment.

The foregoing and other objects and features of the disclosure will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 provides an overview of the information needed for unambiguous identification of antibody chain pairing. Also shown are the location disulfide bonds in the variable region of IgG1.

FIGS. 2A-2B is a flowchart of an exemplary method for determining antibody chain pairing in a sample consisting of one or more types of intact antibodies or antibody fragments.

FIGS. 5A-5C. Trastuzumab (herein also referred to as Herceptin) light chain (A) and heavy chain with G0F glycosylation. (B) Product ion maps illustrating sequence coverage produced by EChcD with 80 eV/q collision energy. Intramolecular disulfide bonds are illustrated with dashed lines, and the CDR3 region of each chain is highlighted. The corresponding MS/MS spectrum. (C) For the 25+ charge state of intact Trastuzumab with insets showing the zoomed in region containing the 9+ charge state of the light chain and various prod-uct ions. Blue and red product ion labels correspond to the heavy and light chains, respectively. Asterisk indicates the mass selected precursor ion.

FIGS. 6A-6C. Trastuzumab light chain (A) and heavy chain with GoF glycosylation. (B) Product ion maps illustrating sequence coverage produced by 157 nm UVPD (2 laser pulses at 1 mJ) with 20 eV/q collision energy during transfer from the HCD cell to the C-trap. Intramolecular disulfide bonds are illustrated with dashed lines, and the CDR3 region of each chain is high-lighted. The corresponding MS/MS spectrum. (C) For the 27+ charge state of intact Trastuzumab with insets showing the zoomed in region containing the 13+ charge state of the light chain and various product ions. Blue and red product ion labels correspond to the heavy and light chains, respectively. Asterisk indicates the mass selected precursor ion.

FIGS. 10A-10B. EChcD with 80 eV/q collision energy (A) and 157 nm UVPD (three 1 mJ pulses; B) spectra of the 15+ charge state of the Fab fragment of Trastuzumab.

FIGS. 11A-11B. Product ion maps for the light chain (A) and Fd subunit (B) produced by EChcD of the F(ab')2 fragment of Trastuzumab using ExD cell setting that yielded more efficient ECD (FIG. 9). CDR3 regions are highlighted in yellow.

Figures 12A, 12B:
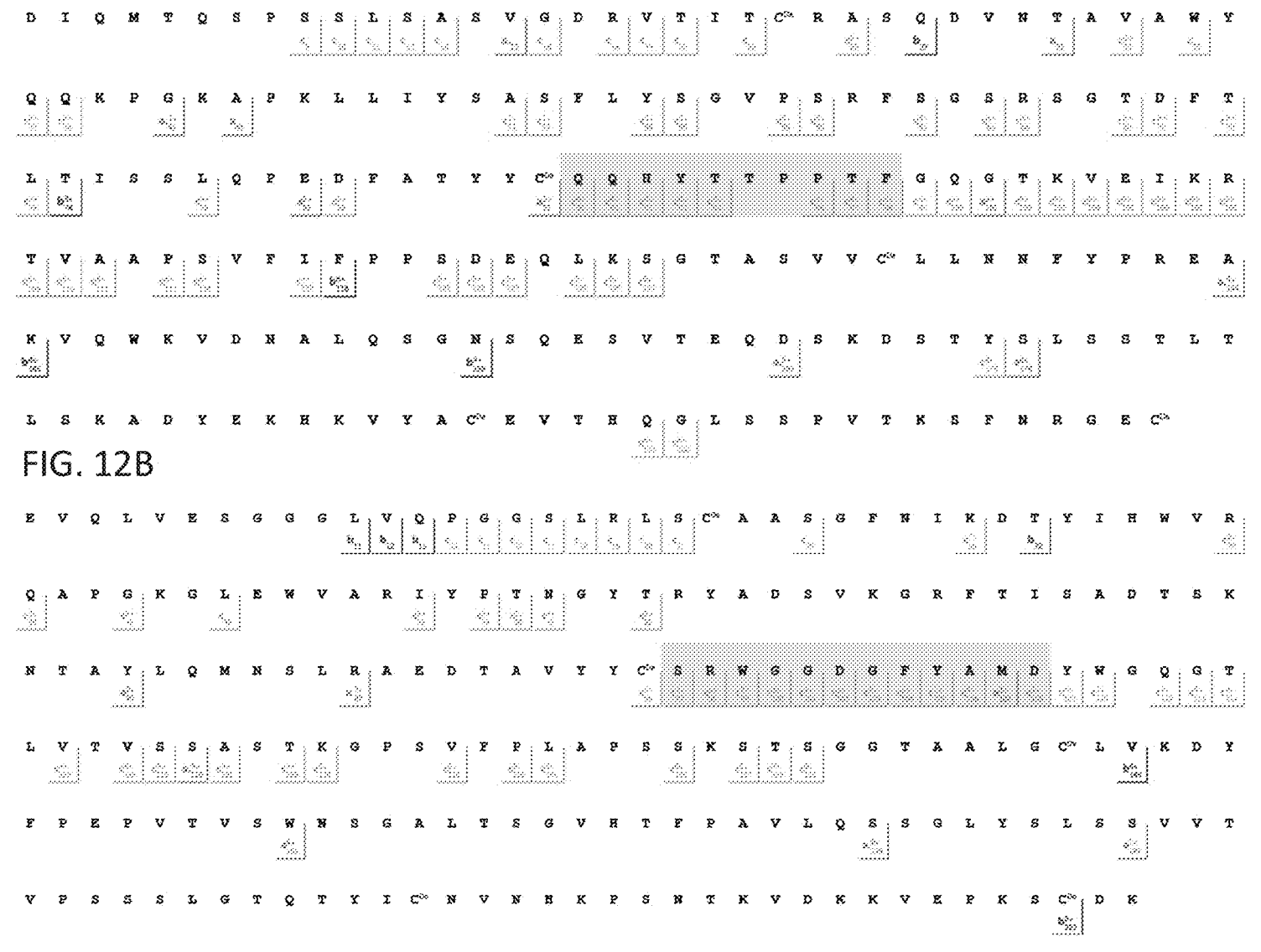

FIGS. 12A-12B. Light chain (A) and Fd (B) product ion maps for EChcD with 70 eV/q collision energy of the 15+ charge state of the Trastuzumab Fab fragment. CDR3 is highlighted in yellow.

Figures 13A, 13B:
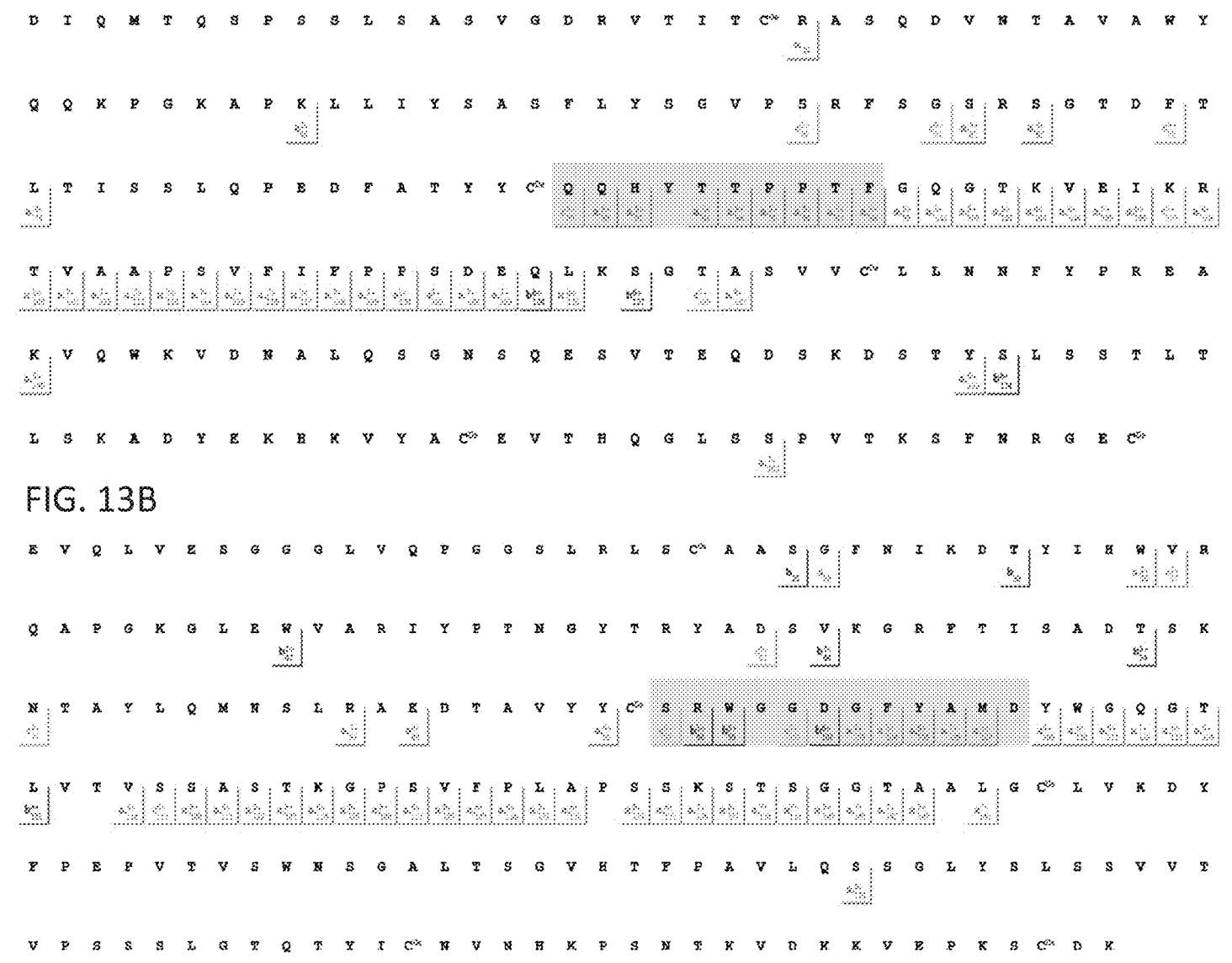

FIGS. 13A-13B. Light chain (A) and Fd (B) product ion maps for 157 nm UVPD (3 pulses at 1 mJ/pulse) of the 15+ charge state of the Trastuzumab Fab fragment. CDR3 is highlighted in yellow.

FIGS. 14A-14D. Zoomed in portions of EChcD with 80 eV/q collision energy (A and C) and 157 nm UVPD (3 pules at 1 mJ; B and D) spectra showing species related to the Fd subunit (A and B) and light chain (C and D) resulting from cleavage of the intermolecular disulfide bond of the Trastuzumab Fab fragment.

DETAILED DESCRIPTION

Figure 2A:
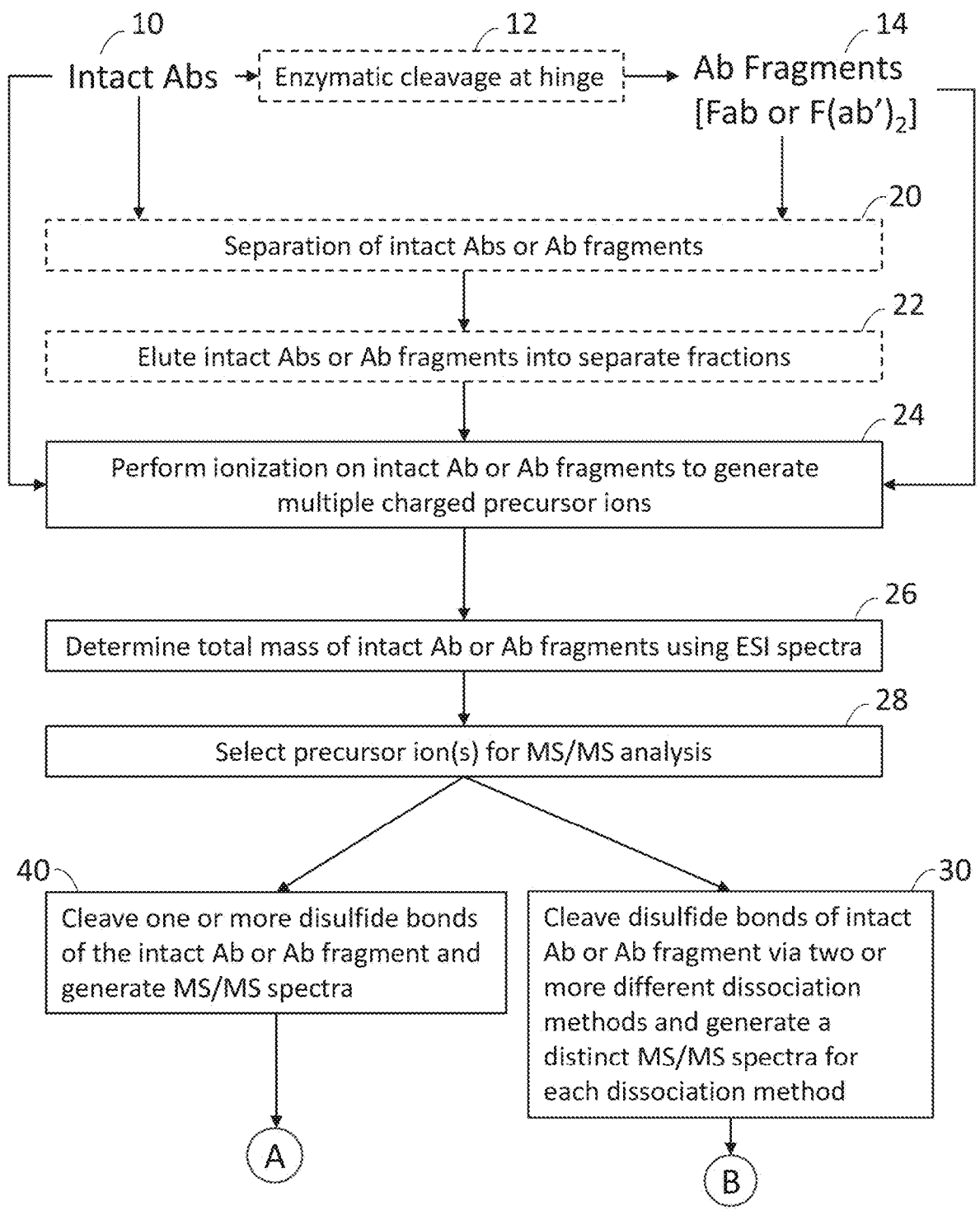
Figure 3:
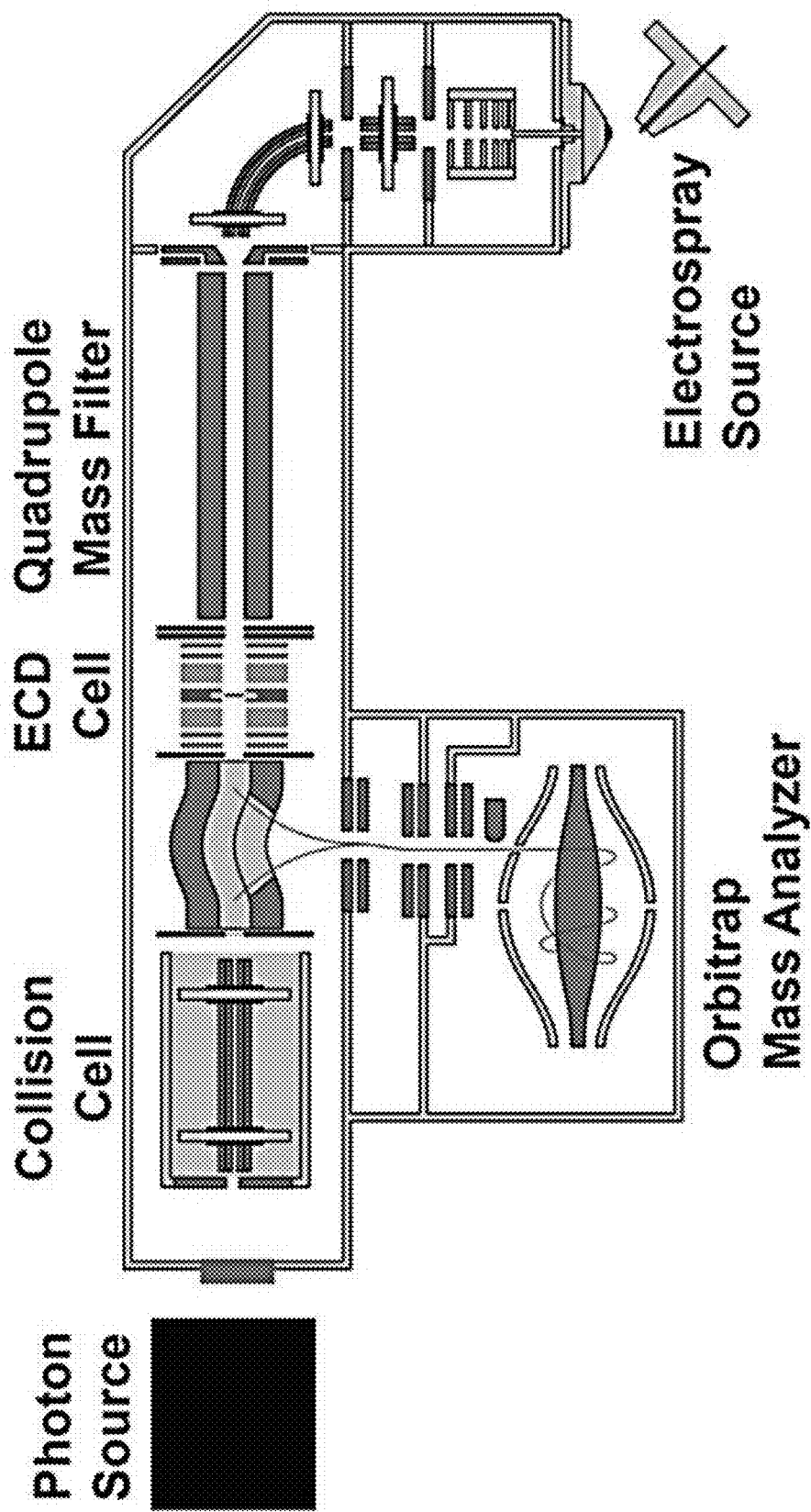
FIG. 3 is a schematic diagram showing an exemplary Ultra High Mass Range Hybrid Mass spectrometer that may be used for the direct determination of antibody chain pairing in accordance with an embodiment of the present disclosure. The spectrometer includes an electrospray ion source, quadrupole mass filter, ECD cell, collision cell/ion-trapping device, photon source, and mass analyzer.

Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 1995 (ISBN 0471186341); and George P. Rédei, *Encyclopedic Dictionary of Genetics, Genomics, and Proteomics*, 2nd Edition, 2003 (ISBN: 0-471-26821-6).

The singular forms "a," "an," and "the" refer to one or more than one, unless the context clearly dictates otherwise. For example, the term "comprising an antibody" includes single or plural antibodies and is considered equivalent to the phrase "comprising at least one antibody." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Except as otherwise noted, the methods and techniques of the present disclosure can be performed according to conventional methods known in the art and as described in various general and more specific references that are cited and discussed throughout the present specification. See, e.g., Sambrook et al., *Molecular Cloning: A Laboratory Manual,* 2d ed., Cold Spring Harbor Laboratory Press, 1989; Sambrook et al., *Molecular Cloning: A Laboratory Manual,* 3d ed., Cold Spring Harbor Press, 2001; Ausubel et al., *Current Protocols in Molecular Biology,* Greene Publishing Associates, 1992 (and Supplements to 2000); Ausubel et al., *Short Protocols in Molecular Biology: A Compendium of Methods from Current Protocols in Molecular Biology,* 4th ed., Wiley & Sons, 1999; Harlow and Lane, Antibodies: A Laboratory Manual, Cold Spring Harbor Laboratory Press, 1990; and Harlow and Lane, *Using Antibodies: A Laboratory Manual,* Cold Spring Harbor Laboratory Press, 1999.

I. Explanation of Terms

Antibody: A polypeptide ligand comprising at least a light chain or heavy chain immunoglobulin variable region which specifically recognizes and binds an epitope of an antigen. Antibodies are composed of a heavy chain (HC) and a light chain (LC), each of which has a variable region, termed the variable heavy ($V_H$) region and the variable light ($V_L$) region. Together, the $V_H$ region and the $V_L$ region are responsible for binding the antigen recognized by the antibody.

Antibodies include portions of antibodies, such as those not having an Fc region, such as Fab fragments, Fab' fragments, F(ab')$_2$ fragments, CH2 deleted Ab, single domain V-region Ab, single chain Fv proteins ("scFv"), and disulfide stabilized Fv proteins ("dsFv"). Another exemplary antibody fragment is the Fd region. A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook,* 1994-1995 (Pierce Chemical Co., Rockford, Ill.); Kuby, J., *Immunology,* 3$^{rd}$ Ed., W. H. Freeman & Co., New York, 1997.

In some examples, antibodies include immunoglobulins that have an Fc region that is mutated or even deleted to substantially decrease the function of the Fc region. In some examples, the mutation decreases the function of the Fc region, such as an ability to bind to Fcy receptor, by at least 50%, at least 75%, at least 80%, at least 90%, at least 95%, at least 99%, or 100% as compared to the function of the Fc region without the mutation.

Typically, a naturally occurring immunoglobulin has heavy (H) chains and light (L) chains interconnected by disulfide bonds. There are two types of light chain, lambda (l) and kappa (k). There are five main heavy chain classes (or isotypes) which determine the functional activity of an antibody molecule: IgM, IgD, IgG, IgA and IgE.

Each heavy and light chain contains a constant region and a variable region (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs have been defined (see, Kabat et al., *Sequences of Proteins of Immunological Interest,* U.S. Department of Health and Human Services, 1991, which is hereby incorporated by reference). The Kabat database is now maintained online. The sequences of the framework regions of different light or heavy chains are relatively conserved within a species, such as humans. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. Antibodies with different specificities (i.e., different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

"Polyclonal antibodies" (pAb) are antibodies secreted by different B cell lineages within the body (whereas monoclonal antibodies come from a single cell lineage). They are a collection of immunoglobulin molecules that react against a specific antigen, each identifying a different epitope. Polyclonal antibodies include a plurality of different monoclonal antibodies, each generated to a different epitope of the antigen.

A "monoclonal antibody" (mAb) is an antibody produced by a single clone of B lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs (which generally confer antigen binding) from another species, such as a murine antibody.

A "humanized" immunoglobulin is an immunoglobulin including a human framework region and one or more CDRs from a non-human (for example a mouse, rat, or synthetic)

immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they are substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

A "human" antibody (also called a "fully human" antibody) is an antibody that includes human framework regions and all of the CDRs from a human immunoglobulin. In one example, the framework and the CDRs are from the same originating human heavy and/or light chain amino acid sequence. However, frameworks from one human antibody can be engineered to include CDRs from a different human antibody. All parts of a human immunoglobulin are substantially identical to corresponding parts of natural human immunoglobulin sequences.

"Specifically binds" refers to the ability of individual antibodies to specifically immunoreact with an antigen, relative to binding to unrelated proteins. The binding is a non-random binding reaction between an antibody molecule and an antigenic determinant of the T cell surface molecule. The desired binding specificity is typically determined from the reference point of the ability of the antibody to differentially bind the T cell surface molecule and an unrelated antigen, and therefore distinguish between two different antigens, particularly where the two antigens have unique epitopes. An antibody that specifically binds to a particular epitope is referred to as a "specific antibody".

In some examples, an antibody or fragment thereof specifically binds to a target with a binding constant that is at least $10^3$ $M^{-1}$ greater, $10^4$ $M^{-1}$ greater or $10^5$ $M^{-1}$ greater than a binding constant for other molecules in a sample or subject. In some examples, an antibody (e.g., monoclonal antibody) or fragments thereof, has an equilibrium constant (Kd) of 1 nM or less. For example, an antibody or fragment thereof binds to a target with a binding affinity of at least about $0.1 \times 10^{-8}$ M, at least about $0.3 \times 10^{-8}$ M, at least about $0.5 \times 10^{-8}$ M, at least about $0.75 \times 10^{-8}$ M, at least about $1.0 \times 10^{-8}$ M, at least about $1.3 \times 10^{-8}$ M at least about $1.5 \times 10^{-8}$ M, or at least about $2.0 \times 10^{-8}$ M, at least about $2.5 \times 10^{-8}$, at least about $3.0 \times 10^{-8}$, at least about $3.5 \times 10^{-8}$, at least about $4.0 \times 10^{-8}$, at least about $4.5 \times 10^{-8}$, or at least about $5.0 \times 10^{-8}$ M. In certain embodiments, a specific binding agent that binds to target has a dissociation constant (Kd) of ≤104 nM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M). In one embodiment, Kd is measured by a radiolabeled antigen binding assay (RIA) performed with the Fab version of an antibody of interest and its antigen (see, e.g., Chen et al., *J. Mol. Biol.* 293:865-881, 1999). In another example, Kd is measured using surface plasmon resonance assays using a BIACORES-2000 or a BIACORES-3000 (BIAcore, Inc., Piscataway, N.J.) at 25° C. with immobilized antigen CMS chips at about 10 response units (RU).

Antibody Class: There are five immunoglobulin classes (isotypes) of antibody molecules: IgG, IgM, IgA, IgE and IgD. They are distinguished by the type of heavy chain they contain. IgG molecules possess heavy chains known as γ-chains; IgMs have μ-chains; IgAs have α-chains; IgEs have ε-chains; and IgDs have δ-chains. The amino acid sequences that confer these functional differences are located mainly within the Fc domain. Immunoglobulins can be further broken down into subclasses. For example, for IgA, there are two (IgA1, IgA2) and for IgG there are four (IgG1, IgG2, IgG3 and IgG4).

Antibody classes also differ in their valency, i.e. the number of arms available to bind antigen. This arises from the ability of certain immunoglobulins to form multimers through linkage of their Fc domains via a J chain. For example, IgM is a pentamer of five identical "Y" shaped monomers. Therefore, the complete IgM protein contains 10 heavy chains, 10 light chains and 10 antigen binding arms (giving IgM a valency of 10). In humans, there are only two kinds of light chains—κ and λ (based on amino acid differences in the VL and CL regions). Any antibody can be formed by the association of one heavy chain type with one light chain type. In every possible combination there will be two identical heavy and light chains in the antibody unit (monomer). Hence the IgM pentamer can either comprise (μ2κ2)5 or (μ2λ2)5.

Electrospray ionization (ESI): A technique used in mass spectrometry to produce ions using an electrospray in which a high voltage is applied to a liquid to create an aerosol. It is used in producing ions from macromolecules (such as antibodies or antibody fragments) because it overcomes the propensity of these molecules to fragment when ionized. Due to the smaller degree of fragmentation produced via ESI, the molecular ion is observed and can be used to infer the mass of the molecule accurately.

ESI differs from other ionization processes (e.g., matrix-assisted laser desorption/ionization (MALDI)) since it may produce multiple-charged ions, effectively extending the mass range of the analyser to accommodate the kDa-MDa orders of magnitude observed in proteins and their associated polypeptide fragments. Mass spectrometry using ESI is called electrospray ionization mass spectrometry (ESI-MS). The ionization chamber is kept in a vacuum so the ions that are produced can progress through the instrument without running into molecules from air. Next, in the mass analyzer, the ions are accelerated through a potential difference and focused into a beam. The ion beam passes through a magnetic field which bends the charged stream. Lighter components or components with more ionic charge will deflect in the field more than heavier or less charged components. When used, MALDI generates singly charged precursor ions.

F(ab')$_2$ fragment: F(ab')$_2$ fragments have two antigen-binding Fab portions linked together by disulfide bonds, and therefore are divalent. This fragment is void of most, but not all, of the Fc region. Pepsin can be used to cleave an immunoglobulin monomer into an F(ab')$_2$ fragment and a portion of the Fc region. In some examples, an F(ab')$_2$ fragment is about 110 kD.

Fab fragment: A region of an antibody that binds to the antigen. These fragments are composed of one constant and one variable domain of each of the HC and LC. The variable domain contains the paratope (the antigen-binding site), comprising a set of complementarity-determining regions, at the amino terminal end of the monomer. Each arm of the Y thus binds an epitope on the antigen. Papain can be used to cleave an immunoglobulin monomer into two Fab fragments and an Fc fragment. In some examples, a Fab fragment is about 50 kD.

Fd region: A portion of an antibody located at the N-terminal part of the heavy chain. It is an essential component of the antigen-binding fragment Fab. Fd, like the light chain, contains a C-terminal constant (CH1) and N-terminal variable (VH) domain. See FIG. 1.

Hinge cleavage enzyme: An enzyme capable of digesting or cleaving an antibody at or near the hinge, to produce antibody fragments, such as Fab and F(ab')2. Such enzymes can cleave antibodies below or above the inter-HC disulfide bonds in the hinge region. The immunoglobulin hinge (interdomain) region is a flexible amino acid stretch in the central part of the heavy chains of the IgG and IgA immunoglobulin classes, which links these two chains by disulfide bonds. In one example, the enzyme digests an intact antibody into an Fab region and an Fc region. Examples of such antibodies include papain (a thiol-type protease). In another example, the enzyme digests an intact antibody into an F(ab')2 region and a pFc' region. Examples of such antibodies include pepsin (an acid-type protease). In one example, the enzyme is ficin (a thiol-type protease), which can digest mouse monoclonal IgG1 into either F(ab')2 or Fab fragments.

Isolated: An "isolated" biological component (such as an antibody or antibody fragment) has been substantially separated, produced apart from, or purified away from other biological components in the cell of the organism in which the component occurs, such as chromosomal and extrachromosomal DNA and RNA, and other proteins. Nucleic acids molecules and proteins which have been "isolated" thus include nucleic acids and proteins purified by standard purification methods. The term also embraces nucleic acid molecules and proteins prepared by recombinant expression in a host cell as well as chemically synthesized nucleic acids and proteins. A purified or isolated antibody or antibody fragment can be at least 70%, at least 80%, at least 90%, at least 95%, at least 96%, at least 97%, at least 98%, or at least 99% pure.

Liquid chromatography (LC): An analytical chemistry technique used to separate, identify, and quantify each component in a mixture (for example, separating components of a biological sample such as a mixture of intact antibodies, or a mixture of antibody fragments; separating natural or synthetic chemicals from each other, etc). The method uses pumps to pass a pressurized liquid solvent containing the sample mixture through a column filled with a solid adsorbent material. Each component in the sample interacts differently with the adsorbent material, causing different flow rates for the different components and leading to the separation of the components as they flow out of the column. The different interactions of each component with the adsorbent may be a function of their mass, their charge, their ionization state at the pH of the elution buffer, their hydrophobicity, other parameters, or any combination of the parameters.

The active component of the column, the adsorbent, is typically a granular material made of solid particles (e.g., silica, polymers, etc.), which in some examples are 2-50 µm in size. The components of a sample (such as one containing intact antibodies and/or antibody fragments) are separated from each other due to their different degrees of interaction with the adsorbent particles. The pressurized liquid is typically a mixture of solvents (e.g., water, acetonitrile and/or methanol) and is referred to as a "mobile phase". The composition and temperature affect the separation process by influencing the interactions taking place between sample components and the adsorbent. These interactions can be physical in nature, such as hydrophobic (dispersive), dipole-dipole and ionic, or a combination thereof.

LC performed in tandem with a mass spectrometer is referred to as high pressure liquid chromatography (HPLC), wherein operational pressures are significantly raised (e.g., about 50-350 bar) through the use of a pressure pump as compared to ordinary low pressure liquid chromatography which relies on the force of gravity to pass the mobile phase through the column. Due to the small sample amount separated in analytical HPLC, exemplary column dimensions are 2.1-4.6 mm diameter, and 30-250 mm length. Also HPLC columns are made with smaller adsorbent particles (e.g., about 2-50 µm in average particle size).

The HPLC instrument typically includes a degasser, sampler, pumps, and a detector. The sampler brings the sample mixture into the mobile phase stream which carries it into the column. The pumps deliver the desired flow and composition of the mobile phase through the column. The detector generates a signal proportional to the amount of sample component emerging from the column (or "eluting" from the column), hence allowing for quantitative analysis of the sample component. In one example, as described herein, different components of a sample (such as a sample containing multiple intact antibodies of different types, or multiple antibody fragments of different types) are loaded onto the LC column and are eluted into separate fractions, each fraction then analyzed via mass spectroscopy.

In some examples, pumps used in LC can mix multiple solvents together in ratios changing over time, generating a composition gradient in the mobile phase. Various detectors are in common use, such as UV/Visible, photodiode array (PDA) o mass spectrometry based detection. HPLC instruments can also have a column oven that allows for adjusting the temperature at which the separation is performed.

One exemplary LC method is reverse phase liquid chromatography (RPLC) that is used to separate non-polar molecules in solution. In RPLC, the stationary phase or adsorbent is non-polar while the mobile phase or solvent is polar. Example adsorbents used in RPLC columns include alkyl groups that are chemically bonded to a silica gel such as butyl group (C4), octadecyl group (C18), octyl group (C8), trimethyl group, phenyl groups, cyanopropyl group, etc.

Another exemplary liquid chromatography method is normal phase liquid chromatography, which can be used to separate polar molecules in solution based on their interaction with a polar stationary phase in the presence of a non-polar mobile phase or solvent.

Mammal: This term includes both human and non-human mammals. Similarly, the term "subject" includes both human and veterinary subjects (such as cats, dogs, cows, and pigs) and rodents (such as mice and rats).

Mass spectrometry (MS): An analytical technique used to separate the components of a sample (such as intact antibodies and antibody fragments) by their mass and electrical charge. A mass spectrometer instrument produces a mass spectrum that plots the mass-to-charge (m/z) ratio of compounds in a mixture. The three main components of a mass spectrometer are the ion source, the mass analyzer, and the detector.

The sample introduced into the mass spectrometer may be a solid, liquid, or gas. The sample is vaporized into a gas and then ionized by the ion source, usually by losing an electron to become a cation. Ionization occurs from electrons that are produced by heating up a metal coil until it releases electrons. These electrons collide with sample molecules, knocking off one or more electrons. Since it takes more energy to remove more than one electron, most cations produced in the ionization chamber carry a +1 charge.

There are several different types of mass analyzers. A time-of-flight (TOF) analyzer accelerates ions to the same potential and then determines how long is needed for them to hit the detector. If the particles all start with the same charge, the velocity depends on the mass, with lighter components reaching the detector first. Other types of detectors measure not only how much time it takes for a particle to reach the detector, but how much it is deflected by an electric and/or magnetic field, yielding information besides just mass. The detector counts the number of ions at different deflections. The data is plotted as a graph or spectrum of different masses. Detectors record the induced charge or current caused by an ion striking a surface. Because the signal is very small, an electron multiplier, Faraday cup, or ion-to-photon detector may be used to amplify the signal to produce a spectrum having a plurality of peaks.

Precursor ion: In MS, such as tandem MS, a precursor ion is an ion of a particular mass that is selected for fragmentation/dissociation. During ionization, for example ESI (e.g., using a mass spectrometer), a sample can undergo specified losses of an electron due to collision induced dissociation to generate precursor ions.

Product ion: In MS, such as tandem MS, a product ion is an ion of a particular mass generated by fragmentation of a product ion. The precursor ion can undergo different types of losses to generate the product ion such as unimolecular dissociation, ion/molecule reaction, change in charge state, and/or isomerization.

Sample: Any biological specimen obtained from a subject, such as a mammalian subject, that contains antibodies. Biological samples include all useful clinical samples, including, but not limited to, cells, tissues, and bodily fluids, such as blood; derivatives and fractions of blood (such as serum and plasma); cerebrospinal fluid; urine; biopsied or surgically removed tissue; fine needle aspirates; sputum; and saliva.

Subject: Any mammal, such as humans, non-human primates, pigs, sheep, cows, dogs, cats, rodents and the like which may have antibodies that can be analyzed using the methods provided herein. In two non-limiting examples, a subject is a human subject or a murine subject.

II. Overview

As shown in FIG. 1, immunoglobulins (Ig) contain two identical HC and two identical LC linked by a plurality of disulfide bonds. Antigen specificity is dictated by three complementarity determining regions (CDR1, CDR2, CDR3) in the N-terminal portion of each chain. There are four subclasses of IgG (IgG1, IgG2, IgG3, IgG4) that are numbered in order of abundance and differ in the number and structure of the intermolecular disulfide bonds in the hinge region. IgG1 has two intermolecular disulfide bonds linking the two HC and one disulfide bond linking the LC to the HC.

As shown in FIG. 1, several pieces of information are needed to unambiguously determine HC and LC pairing using the disclosed methods. First, intact mass of the intact antibody, F(ab')$_2$, or Fab needs to be made as accurately as possible, especially if working with pAbs. The intact mass of the LC and HC (or Fd domain) also needs to be measured as accurately as possible after gas phase cleavage of intermolecular disulfide bonds. Finally, product ions that yield sequence coverage of a unique region of the antibody, such as the complementarity determining regions (CDRs, such as CDR3), are needed to unambiguously determine chain pairing. This information can then used to query antibody chain sequence databases generated by B cell sequencing, MS/MS de novo sequencing, or other methods. CDR sequences alone may be sufficient to identify chains in the database. However, in cases where CDR sequences are not unique, accurate intact mass of the chains can be used to confirm/eliminate candidate chain sequences.

The present disclosure provides methods that allow for direct determination of heavy chain (HC) and light chain (LC) pairing of an intact antibody or antibody fragment, for example, in a sample containing one or more intact polyclonal antibodies (pAbs), a sample containing one or more intact monoclonal antibodies (mAbs), or a sample containing one or more antibody fragments (which can be generated from pAbs or mAbs (e.g., Fab fragments and/or F(ab')$_2$ fragments)). The disclosed methods provide several improvements over currently available proteomics-based approaches for antibody chain pairing determination.

The method was initially tested using an antibody with a known sequence, Trastuzumab (Herceptin). Trastuzumab is an IgG1. Trastuzumab was examined with all the disulfide bonds intact and under native electrospray conditions. Efficient dissociation of native-like charge state mAb ions was heavily reliant on multiple stages of ion activation. In-source trapping [38] was used for collision induced unfolding followed by precursor selection in the quadrupole mass filter and MS/MS using ECD with supplemental collisional activation in the HCD cell (termed EChcD) [36] or 157 nm UVPD.

The ability to cleave intermolecular disulfide bonds linking the heavy and light chains of a monoclonal antibody at the intact and fragment levels under native electrospray conditions using EChcD and 157 nm UVPD is shown herein. This enabled accurate mass determination of the intact light chains and Fd subunit. Extensive sequence coverage of the regions between intramolecular disulfide bonds yield high sequence coverage of the heavy and light chain CDR3s. Additionally, the ability to fragment low charge state precursor ions yielded MS/MS spectra far less congested than traditionally observed from denaturing conditions. The results presented here illustrate de novo structure characterization workflows that lessen reliance on single-cell B cell sequencing and hybridoma based methods for therapeutic antibody discovery.

Methods for determining chain pairing of an intact antibody are provided. In one example, the method includes ionizing the intact antibody into precursor ions; determining a mass of the intact antibody from a mass spectrum of the precursor ions; selecting one or more precursor ions for MS/MS analysis; dissociating by a first dissociation method, a light chain of the intact antibody from a heavy chain of the intact antibody to generate a first type of product ions of the light chain and produce a first mass spectrum of the light chain; and dissociating by a second dissociation method, the light chain of the intact antibody from the heavy chain of the intact antibody to generate a second type of product ions of the light chain and produce a second mass spectrum of the light chain, wherein the first dissociation method cleaves a backbone of the light chain at a different location than the second dissociation method. The methods can further include comparing the first mass spectrum to the second mass spectrum to identify a first group of the first type of product ions that differ in mass from a second group of the second type of product ions by a constant value; determining an amino acid sequence of the light chain based on a mass difference between consecutive product ions of the first group and/or consecutive product ions of the second group; determining a mass of the light chain from the first or second mass spectrum; determining a mass of the heavy chain of the intact antibody based on the mass of the intact antibody and the mass of the light chain; comparing the determined sequence of the light chain and the mass of the heavy chain with a database including amino acid sequences of light chain sequences and heavy chain sequences; and determining heavy chain and light chain pairing of the intact antibody or antibody fragment.

Also provided are methods of determining chain pairing of an antibody fragment. Such methods can include ionizing the antibody fragment into precursor ions; determining a mass of the antibody fragment from a mass spectrum of the precursor ions; selecting one or more precursor ions for MS/MS analysis; dissociating by a first dissociation method, a light chain of the antibody fragment from an Fd portion of the antibody fragment to generate a first type of product ions of the light chain and a first mass spectrum of the light chain, and a first type of product ions of the Fd portion and a first mass spectrum of the Fd portion, wherein the Fd portion is derived from a heavy chain; dissociating by a second dissociation method, the light chain of the antibody fragment from the Fd portion of the antibody fragment to generate a second type of product ions of the LC chain and a second mass spectrum of the LC chain, and a second type of product ions of the Fd portion and a second mass spectrum of the Fd portion, wherein the first dissociation method cleaves a backbone of the Fd portion at a different location than the second dissociation method. The method can further include comparing the first mass spectrum of the light chain to the second mass spectrum of the light chain to identify a first group of the first type of product ions that differ in mass from a second group of the second type of product ions by a constant value; comparing the first mass spectrum of the Fd portion to the second mass spectrum of the Fd portion to identify a first group of the first type of product ions that differ in mass from a second group of the second type of product ions by a constant value; determining, from the first and/or second mass spectrum of the light chain, an amino acid sequence of the light chain based on a mass difference between consecutive product ions of the first group and/or consecutive product ions of the second group; determining an amino acid sequence of the light chain based on a mass difference between consecutive product ions of the first group and/or consecutive product ions of the second group; determining, from the first and/or second mass spectrum of the Fd portion, an amino acid sequence of the Fd portion based on a mass difference between consecutive product ions of the first group and/or consecutive product ions of the second group; and determining an amino acid sequence of the Fd portion based on a mass difference between consecutive product ions of the first group and/or consecutive product ions of the second group. The method can further include comparing the determined sequence of the light chain and Fd portion with a database containing amino acid sequences of light chain sequences and heavy chain sequences; and determining heavy chain and light chain pairing of the antibody fragment.

In other examples, determining chain pairing of an or antibody fragment, includes ionizing the intact antibody or antibody fragment into precursor ions; determining a mass of the intact antibody or a mass of the antibody fragment from a mass spectroscopy spectrum of the precursor ions; selecting one or more precursor ions for MS/MS analysis; dissociating at least a light chain from the intact antibody by cleaving one or more disulfide bonds linking a heavy chain and the light chain of the intact antibody, or dissociating an intact light chain and a heavy chain fragment from the antibody fragment by cleaving disulfide bonds linking the heavy chain fragment and the light chain of the antibody fragment. The method can further include determining a mass of the light chain of the intact antibody from a mass spectroscopy spectrum of a product ion of the light chain of the intact antibody, or determining a mass of the light chain of the antibody fragment from a mass spectroscopy spectrum of a product ion of the light chain of the antibody fragment and determining a mass of the heavy chain fragment from a mass spectroscopy spectrum of a product ion of the heavy chain fragment of the antibody fragment; and comparing the identified mass of the light chain and the mass of the intact antibody with a database comprising amino acid sequences of light chain sequences and heavy chain sequences or comparing the identified mass of the light chain and the mass of the heavy chain fragment with a database containing amino acid sequences of light chain sequences and heavy chain sequences. The method can further include determining heavy chain and light chain pairing of the intact antibody or antibody fragment.

In some examples, the intact antibody or antibody fragment comprises a plurality of intact antibodies or a plurality of antibody fragments. In some examples, the sequence of the antibody or antibody fragment is unknown prior to analysis with the disclosed methods.

In some examples, the method further includes enzymatically cleaving the intact antibody at or near the hinge with a hinge cleavage enzyme, such as pepsin or papain, to generate one or more antibody fragments.

In some examples, the intact antibody is an IgG or IgA, such as IgG1. In some examples, the antibody fragment is Fab, F(ab')$_2$, or both.

In some examples, the method further includes, prior to ionizing the intact antibody or antibody fragment, separating the intact antibody or the antibody fragment into individual intact antibody populations or antibody fragment populations. For example, the separating can be by mass, total charge, or hydrophobicity of the intact antibody or antibody fragment. In some examples liquid chromatography is used. In some examples, the following the separating, the individual intact antibody populations or antibody fragment populations are eluted into separate fractions.

In some examples, the ionizing method uses electrospray ionization (ESI).

In some examples, the dissociation method used is one or more of electron capture dissociation (ECD), electron transfer dissociation (ETD), electron detachment dissociation (EDD), or ultraviolet photodissociation (UVPD).

In some examples, the first dissociation method is ultraviolet photodissociation (UVPD) and the first type of product ions are a-ions, and the second dissociation method is electron capture dissociation (ECD) and the second type of product ions are c-ions, and the constant value is 45.0215. In some examples, the first type of product ions are a-ions, and the second type of product ions are c-ions, and the constant value is 45.0215; the first type of product ions are a-ions, and the second type of product ions are b-ions, and the constant value is 27.99495, or the first type of product ions are c-ions, and the second type of product ions are b-ions, and the constant value is 17.0267.

In some examples, determining a mass of the intact antibody or mass of the antibody fragment from a mass spectrum of the precursor ions comprises determining an m/z value of a precursor ion having a +1 charge state.

In some examples, selecting one or more precursor ions for MS/MS analysis comprises selecting a most abundant precursor ion for MS/MS analysis.

In some examples, the method further includes determining a mass of an intact heavy chain from the intact antibody.

In some examples, the method further includes comparing the identified mass of the light chain with a calculated theoretical mass of each light chain sequence of a database comprising a plurality of light chain sequences, and selecting a candidate light chain having the calculated theoretical mass within a threshold error of the identified mass of the light chain; and comparing the identified mass of the Fd portion with a calculated theoretical mass of an Fd portion of each heavy chain sequence of a database containing a plurality of heavy chain sequences, and selecting a candidate heavy chain having the calculated theoretical mass within a threshold error of the identified mass of the Fd portion.

In some examples, the method further includes comparing the identified mass of the light chain with a calculated theoretical mass of each light chain sequence of a database comprising a plurality of light chain sequences, and selecting a candidate light chain having the calculated theoretical mass within a threshold error of the identified mass of the light chain; and comparing the identified mass of the heavy chain with a calculated theoretical mass of each heavy chain sequence of a database containing a plurality of heavy chain sequences, and selecting a candidate heavy chain having the calculated theoretical mass within a threshold error of the identified mass of the Fd portion.

In some examples, the intact antibody or antibody fragment is selected for an antigen, and the method further comprises generating a monoclonal antibody selected for the antigen, wherein the monoclonal antibody includes a light chain corresponding to the candidate light chain sequence and a heavy chain corresponding to the candidate heavy chain sequence.

III. Methods of Determining Heavy Chain (HC) and Light Chain (LC) Pairing

Provided herein are methods for determining the heavy chain (HC) and light chain (LC) pairing of an antibody or antibody fragment (such as Fab or F(ab')$_2$). An overview of the method is provided in FIGS. 2A-2B. In some examples, a plurality of intact antibodies are analyzed using the disclosed methods simultaneously or contemporaneously, such as a plurality of polyclonal antibodies. In some examples, the plurality of antibodies are a mixture of antibodies specific for the same antigen. In some examples, the plurality of antibodies are a mixture of antibodies specific for different antigens. In some examples, a plurality of antibody fragments are analyzed using the disclosed methods simultaneously or contemporaneously, such as a plurality of antibody fragments. In some examples, the plurality of antibody fragments are a mixture of antibody fragments specific for the same antigen. In some examples, the plurality of antibody fragments are a mixture of antibody fragments specific for different antigens.

As shown in FIG. 2A, intact antibodies 10 or antibody fragments 14 can be analyzed for LC and HC pairing. In some examples, the sequence of antibodies 10 or antibody fragments 14 is not known prior to performing the method, and the method allows for a determination of where the pairing between HC and LC occurs. In some examples, intact antibodies 10 are exposed to an enzyme that can cleave the antibody at the hinge region 12. Digestion with such an enzyme produces antibody fragments 14, such as Fab and F(ab')$_2$. Examples of such enzymes include pepsin and papain. The resulting antibody fragments 14 can be analyzed with the disclosed methods. However, enzymatic cleavage 12 is optional, as the method can be used to analyze intact antibodies 10 not previously exposed to an enzyme that cleaves the antibody at or near the hinge region.

In some examples, the intact antibody 10 or antibody fragments 14 is subjected to an optional separation step 20. For example, if a sample to be analyzed contains a mixture of different intact antibodies 10 (such as a mixture of antibodies that bind to the same antigen, or a mixture of intact antibodies that bind to different antigens), or mixtures of different antibody fragments 14 (such as a mixture of antibody fragments that bind to the same antigen, or a mixture of antibody fragments that bind to different antigens, or a mixture of antibody fragment types (such as a mixture of Fab and Fc, or F(ab')$_2$ and pFc'), the sample may be separated into individual components. Such a separation step can simplify downstream analysis, as it allows for individual intact antibodies or individual antibody fragments to be introduced into the mass spectrometer and reduces interference of peaks in the resulting spectra. Intact antibodies or antibody fragments can be separated 20 by mass, total charge, or hydrophobicity, such as by using liquid chromatography (LC) or capillary electrophoresis (CE).

The resulting separation allows for eluting of the intact antibodies or antibody fragments into individual or separate fractions 22. For example, the resulting separated intact antibodies or antibody fragments can be analyzed serially one at a time.

Intact antibodies 10 and antibody fragments 14 can be directly used for mass spectrometric analysis. The method may include performing electrospray ionization (ESI) on the intact antibodies or antibody fragments to generate multiple charged precursor ions 24. Alternatively, if separation and elution of the intact antibodies 10 and antibody fragments 14 was performed 20, 22, ESI may be performed on the fractions resulting from elution 22. In some examples, the ESI equipment may be coupled to LC equipment allowing for individual eluting fractions having significant separation of individual or populations of intact antibodies or individual or populations of antibody fragments to be directly electrospray ionized into a mass spectrometer. If eluting fractions do not have significant separation, individual elution peaks corresponding to the eluting fractions may be selected for ESI analysis to reduce multiplexing errors.

In one example, ESI of one or more intact antibodies 10, one or more antibody fragments 14, or the individual fractions obtained from the elution 22, generates a corresponding ESI spectra which includes m/z values for each of the multiple charged precursor ions. The ESI spectra generated for a given intact antibody 10 or antibody fragment 14 (which may be in a fraction) is used to determine the total mass of the intact antibody or total mass of the antibody fragment 26. Each mass is determined based on one or more of: (1) the m/z value of a given peak, (2) the multiple charged state of the precursor ion corresponding to the given peak, and (3) the relative distribution of other multiple charged precursor ions. In one example, the mass of the intact antibody or the mass of the antibody fragment can be determined from the m/z value of the precursor ion having a +1 charge state.

After determining the total mass of the intact antibody or total mass of the antibody fragment 26, the method selects one or more precursor ions for tandem MS/MS analysis 28. In one example, the most abundant precursor ion(s) (visible as the tallest peak(s)) is selected for MS/MS analysis. In other examples, a distribution of precursor ions within the ESI spectrum is selected for further MS/MS analysis. That is, several (such as all or less than all) of the precursor ions may be selected for further MS/MS analysis.

The selected precursor ions 28 are subjected to a disulfide bond dissociation or cleavage method 40, 30. That is, the method 40, 30 includes cleaving one or more disulfide bonds (such as 1, 2, 3, 4, 5, 6, 7, 8, 9, or 10 different disulfide bonds) of the selected precursor ion(s) of the intact antibody or antibody fragment 30, 40. In one example, the number of disulfide bonds cleaved is dependent on the class and/or subclass of the intact antibody or antibody fragment. For each intact antibody and antibody fragment, at least one disulfide bond, such as the disulfide bond linking the LC to the HC, is cleaved. Based on whether the antibody fragment is a Fab fragment or a F(ab')$_2$ fragment, there may be additional disulfide bonds in a hinge region coupling the heavy chains to each other (such as may be present in the F(ab')$_2$ fragment but not the Fab fragment). Further, the number of disulfide bonds coupling the heavy chains to each other in the hinge region are based on the antibody class type (e.g., based on whether the antibody fragments are IgG fragments or IgM fragments or IgA fragments, etc.). One or more of the disulfide binds in the hinge region can be cleaved.

Similarly, in the case of an intact antibody, at least one disulfide bond, such as the disulfide bond linking the LC to the HC, is cleaved. The number of additional disulfide bonds coupling the heavy chains to each other are based on the antibody class type (e.g., based on whether the antibody fragments are IgG fragments or IgM fragments or IgA fragments, etc.). During the cleaving 30, 40, one or more of the disulfide bonds coupling the heavy chains to each other may be cleaved.

Figure 4:
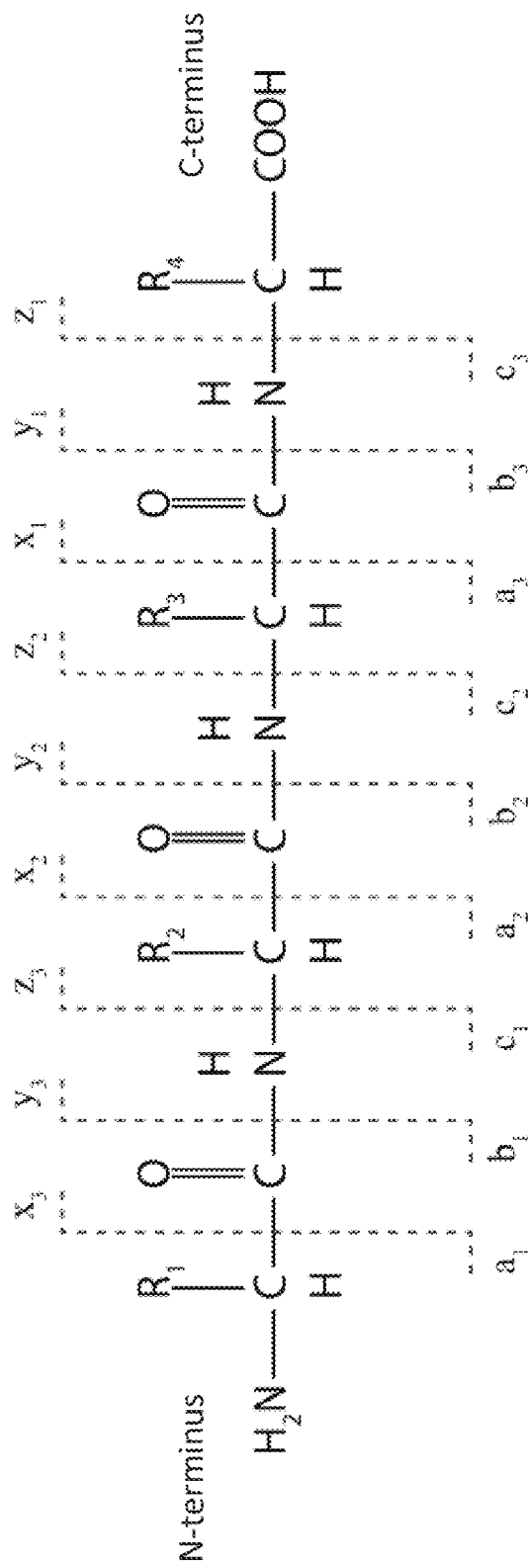
FIG. 4 is a schematic drawing showing peptide fragmentation nomenclature.

In examples where the methods uses a proteomic approach to determine the HC and LC chain pairing, one method can be used to cleave one or more disulfide bonds of the intact antibody or antibody fragment 40. This results in the generation of one set of MS/MS spectra. In some examples, for example when de novo sequencing is used to determine the HC and LC chain pairing, the method uses at least two different methods (such as 2, 3, 4, 5, or 6 different dissociation methods) to cleave one or more disulfide bonds of the intact antibody or antibody fragment 30. This results in at least two different sets of MS/MS spectra, each set corresponding to one of the cleavage methods used. Methods that can be used to cleave or dissociate one or more disulfide bonds of the intact antibody or antibody fragment 30, 40 include one or more of electron capture dissociation (ECD), electron transfer dissociation (ETD), electron detachment dissociation (EDD), ultraviolet photodissociation (UVPD) (for example at 266 nm, 248 nm, 213 nm, 193 nm, 157 nm, etc.), and high energy collision induced dissociation (CID). Each dissociation method produces a unique ion, such as an N-terminal ion (a-ion, b-ion, or c-ion) or a C-terminal ion (x-ion, y-ion, or z-ion). As shown in FIG. 4, although different methods may cleave at the same amino acids, different methods cleave at different bonds, resulting in different masses. Any combination of two methods can be used, as long as each method produces a different ion. For example, UVPD (for example at 193 nm and 157 nm) generates a-ions, while ECD (such as EChcD and ECuvPD) or produces c-ions, thus these two methods (i.e., UVPD and ECD) can be used together. As another example, collision induced dissociation (CID) generates b-ions and can be used with either or both of the above-mentioned methods that generate a-ions and c-ions.

After dissociating one or more disulfide bonds of the precursor ion(s) 40, 30, the MS/MS spectra are used to identify product ions corresponding to the LC, HC, and/or Fd portions of the intact antibody or antibody fragment 32, 42. This identification is performed based on the relative position of product ion peaks relative to the position of the precursor ion peak(s) on the MS/MS spectra. Precursor ions are observed in the MS/MS spectra due to at least a portion of the original intact antibody or antibody fragment not being cleaved during the cleavage step. The mass of the LC, HC, and/or Fd portions is then determined, for example from the m/z value and charge state of a product ion and the m/z value and charge state of a precursor ion corresponding to the given peak.

In the proteomics based approach for determining chain pairing ("A" in FIG. 2A, 2B, steps 40, 42, 44, 46, 48, 50, 52), the determined mass of the LC, HC, and/or Fd portions is used to query a B cell genomic sequencing database for corresponding LC, HC, and/or Fd sequences that correspond to the same mass (or within a threshold mass error tolerance) and/or which result in a similar MS/MS peak profile 44. For example, an algorithm can be used which determines the theoretical mass of all known LC sequences in the database. The theoretical masses are compared to the mass of the LC (for the intact antibody or antibody fragment) as determined via MS/MS analysis, and results are filtered to include theoretical masses that are within a threshold mass error of the queried mass. Based on a match between mass values, one or more candidate sequences are identified for the given LC. In one example, where the mass of the LC determined via MS/MS matches a single theoretical mass from the database, the sequence of the corresponding LC is determined to be the sequence of the LC of the given intact antibody or antibody fragment.

Similarly, in the case of an antibody fragment whose Fd mass is determined via MS/MS analysis, an algorithm that determines the theoretical mass of all known Fd sequences in the database can be used. The database may include intact HC sequences and the algorithm calculates theoretical masses for the Fd portion (which is a defined portion of the HC sequence) of each intact HC sequence. The theoretical masses are compared to the measured mass of the Fd of the analyzed antibody fragment, and results are filtered to include theoretical masses that are within a threshold mass error of the queried mass. Based on a match between mass values, one or more candidate sequences are identified for the given Fd, and thereby the given HC from which the Fd was generated. In one example, where the mass of the Fd determined via MS/MS matches a single theoretical mass from the database, the sequence of the Fd is determined to be the sequence of the HC of the given antibody fragment, and the sequence of the HC corresponding to the identified Fd is determined to be the sequence of the HC of the original intact antibody from which the antibody fragment was generated (e.g., via cleavage of the intact antibody at the hinge region).

As discussed above, the likelihood of cleavage of a sufficient number of disulfide bonds in an intact antibody is lower than an antibody fragment, and therefore the likelihood of detection of an intact HC product ion (or an Fd product ion) for F(ab')$_2$ in the MS/MS spectra of an intact antibody is lower. This is because the intact antibody has two or more disulfide bonds linking the two HC in the hinge region and one linking the HC to LC. In comparison, the F(ab')$_2$ fragment is a result of enzymatic cleavage below the hinge, so it has two disulfide bonds linking the Fd to Fd and one Fd to LC. The Fab is a result of enzymatic cleavage above the hinge region, so there is only one disulfide bond linking Fd to LC. Therefore, when the starting material includes an intact antibody 10 (e.g., not an antibody fragment 14, and thus step 12 is omitted), the method can optionally determine the mass of the intact HC of an intact antibody 46 based on a calculated difference between the measured mass of the intact antibody sample (as determined via ESI at 26) and the measured mass of the intact LC (as determined via MS/MS at 42).

Once the mass of the intact HC is determined 46, the algorithm can be used to query the B cell genomic sequencing database for HC sequences whose theoretical masses are within a threshold mass error of the queried HC mass or that generate a similar peak profile 48. Based on a match between mass values, one or more candidate sequences are identified for the given HC. In one example, where the calculated mass of the HC matches a single theoretical mass from the database, the sequence of the corresponding HC is determined to be the sequence of the HC of the given intact antibody.

In the de novo sequencing approach ("B" in FIG. 2A, 2B, steps 30, 32, 34, 36, 38, 39), ions are assigned to the MS/MS spectra for the LC peaks generated via the two or more dissociation methods 34. For example, a first ion type (e.g., a-ions) is obtained from a first dissociation method while a second ion type (e.g., b-ions or c-ions) is obtained from a second/different dissociation method. Similarly, Fd peaks and HC peaks from set of spectra generated via a first dissociation method can be compared to corresponding peaks from spectra generated via the other dissociation methods and corresponding ions (e.g., a-, b-, and c-ions) are assigned. Herein, each set of LC peaks corresponds to different LC fragments generated via a particular dissociation method. Likewise, each set of Fd peaks corresponds to different Fd fragments generated via a particular dissociation method, and each set of HC peaks corresponds to different HC fragments generated via a particular dissociation method.

For a given set of peaks (e.g., for LC peaks, HC peaks, or Fd peaks), a first ion is assigned to a first spectrum generated via a first dissociation method (e.g., a-ions for spectra generated via UVPD) and a second ion is assigned to a second spectrum generated via a second dissociation method (e.g., c-ions for spectra generated via ECD). The first ions from the first spectrum of the LC or HC or Fd peaks are compared to the second ions from the second spectrum 36 of the corresponding LC or HC or Fd peaks. In one example, a-ions for peaks corresponding to the LC, dissociated via UVPD for example, are compared to c-ions for peaks corresponding to the LC dissociated via ECD (or ETD). FIG. 6C shows an example assignment of a-ions to LC spectra for an intact antibody dissociated via UVPD while FIG. 6C shows an example assignment of c-ions to LC spectra for the same intact antibody dissociated via ECD.

After comparing the spectra of at least two different ions 36, the spectra comparison is used to determine the sequence of the corresponding precursor ion 38. For a given precursor ion dissociated via two different methods to generate first product ions and second product ions that are aligned to have a constant difference, the method then determines the mass difference of individual amino acids in the sequence of the product ion. A mass difference between consecutive first ions of the first spectra and/or consecutive second ions of the second spectra is used to determine the mass of an amino acid at that position, and thereby the identity of the amino acid.

For example, where a first spectra of LC or HC peaks generated from an intact antibody via UVPD or a first spectra of LC or Fd peaks generated from an antibody fragment via UVPD is compared to a corresponding second spectra of LC or HC peaks generated from the intact antibody via ECD, or a second spectra of LC and Fd peaks generated from an antibody fragment via ECD, after aligning, the mass difference between consecutive a-ions and/or consecutive c-ions is used to learn the mass of the corresponding amino acid that was cleaved at that location. From the mass of the amino acid, the identity of the amino acid is determined. An example sequence determination is shown at FIG. 4. It will be appreciated that the method may determine an entire sequence of the LC or HC or Fd portion (based on whether the spectra of LC or HC or Fd peaks was compared), or portions of the entire sequence.

The determined sequence of the LC or HC portion of the intact antibody, or LC or Fd portion of the antibody fragment is used to query a B-cell genomic sequencing database to identify a corresponding sequence 39. For example, where the LC spectra comparison is used to determine the sequence of at least a portion of the LC, the sequence is compared to known sequences in a database to identify a corresponding sequence. Filter stringency during the matching may be determined as a function of the portion of the sequence that is identified via MS/MS analysis. For example, a higher stringency may be applied when a larger portion of the total LC sequence is covered by the de novo sequence while a lower stringency may be applied when a smaller portion of the total LC sequence is covered by the de novo sequence. Similarly, when Fd spectra comparison is used to determine the Fd de novo sequence, a comparison is made to Fd portion for Fd portion of known HC sequences in the database; and when HC spectra comparison is used to determine the HC de novo sequence, a comparison is made to known HC sequences in the database.

In one example, where the de novo sequence of the LC matches a single LC sequence from the database, the sequence of the corresponding LC is determined to be the sequence of the LC of the given intact antibody or antibody fragment. In another example, where the de novo sequence of the Fd portion matches the Fd portion of a single HC sequence from the database, the sequence of the corresponding HC is determined to be the sequence of the HC of the intact antibody from which the Fd portion of the antibody fragment is derived. In yet another example, where the de novo sequence of the HC matches a single HC sequence from the database, the sequence of the corresponding HC is determined to be the sequence of the LC of the given intact antibody.

In the case of an intact antibody, where Fd data is not available, and MS/MS spectra for the HC was not generated, after determining the identity of the LC, the method may determine the mass of the HC based on the mass of the intact antibody relative to the mass of the intact LC 46 and then query the database for HC sequences having a match in corresponding theoretical mass 48 as discussed above with reference to the proteomics approach.

In some examples, the de novo sequencing approach is used to determine at least the sequence of the complementarity determining regions (CDR) of the antibody or antibody fragment. Antibodies, or antibody fragments, may include CDRs 1-3 which are each part of the variable regions of the LC and HC. Together the CDRs create the paratope of the antibody that binds to the epitope of the corresponding antigen. CDRs constitute the most variable part of the antibody, or antibody fragment, and are found at the N-terminal region. Based on the type or class of immunoglobulin, the position of the CDRs varies relative to the disulfide bonds that connect the LC to the HC. For example, in IgG1, CDR3 lies outside the region that is tied by the disulfide binds (see FIG. 1) while CDR1 and CDR2 lie within the region. Due to the high variability of the CDR sequence relative to the remainder of an antibody sequence, the CDR sequence can be advantageously used as a unique tag for identifying LC and HC sequences.

In one example, when performing de novo sequencing of an LC peak or spectra for an intact antibody of the IgG class, or an antibody fragment of the IgG class, generated via UVPD or ECD, the amino acid sequence at the N-terminal region of the LC, corresponding to the CDR3 region of the LC, may be determined (for example, as described above, by comparing the UVPD spectra to the ECD spectra). The unique CDR3 sequence is then used to query the database of LC sequences. Herein, even when the de novo determined sequence covers less than the entire length of the LC, by relying on the unique sequence region, the LC identity can be reliably and accurately determined. For example, the CDR3 sequence of the LC of the antibody or antibody fragment determined via the de novo approach may be compared to the CDR3 sequence for all LCs in the database, and an LC having a CDR3 region with a higher than 90% match is identified as the LC sequence. In other examples, such as where the antibody or antibody fragment is an IgA or IgM, based on the position of the disulfide bond, the sequence of the CDR1 or CDR2 region of the LC may be determined and compared to the CDR1 or CDR2 region of LC sequences available in the database.

Similarly, when performing de novo sequencing of an HC peak or spectra (of an intact antibody of the IgG class) or an Fd peak or spectra (for an antibody fragment of the IgG class), generated via UVPD or ECD, the amino acid sequence at the N-terminal region of the HC or Fd portion, corresponding to the CDR3 region of the HC or Fd portion, may be determined (for example, as described above, by comparing the UVPD spectra to the ECD spectra). The unique CDR3 sequence is then used to query the database of HC sequences. Herein, even when the de novo determined sequence covers less than the entire length of the HC or Fd portion, by relying on the unique sequence region, the identity of the HC can be reliably and accurately determined. For example, the CDR3 sequence of the HC or Fd portion of the antibody or antibody fragment, respectively, determined via the de novo approach may be compared to the CDR3 sequence for all HCs in the database, and an HC having a CDR3 region with a higher than 90% match to the sequence is identified as the HC sequence. In other examples, such as where the antibody or antibody fragment is an IgA or IgM, based on the position of the disulfide bond, the sequence of the CDR1 or CDR2 region of the HC or Fd portion may be determined and compared to the CDR1 or CDR2 region of HC sequences available in the database.

Once the HC and LC sequences are identified, the method identifies the specific HC and LC pairing 50 for the given intact antibody 10 or antibody fragment for the given antigen that it was exposed to. The identification of the HC and LC pairing can then be used for various applications. In one example, based on the identified pairing, therapeutic mAbs may be created for the given antigen 52 wherein the mAbs are engineered to include the specific HC and LC identities learned via the MS/MS analysis. For example, identified from heavy and light chains (such as a CDR3 sequences) can be grafted into another framework, such as a single chain variable fragment (scFv) framework scaffold. In some examples, the sequence identified is used to make a humanized mAb.

A. Exemplary Antibodies and Antibody Fragments

Referring to FIGS. 2A-2B, in one example, a single intact antibody 10 is analyzed, such as a monoclonal antibody or a polyclonal antibody. The polyclonal antibody can be one that specifically binds to a target. In one example, a plurality of distinct single antibodies 10 are analyzed, such as a population or mixture of two or more different polyclonal antibodies (such as at least two, at least three, at least four, at least 5, at least 6, at least 7, at least 8, at least 9, at least 10, at least 20, at least 50, or at least 100 different polyclonal antibodies). Such a mixture of antibodies may all specifically bind to the same antigen, or may include populations of antibodies each binding to distinct/different antigens. In some examples, the intact antibody or antibody fragment analyzed with the disclosed methods is isolated or purified.

In some examples, the intact antibody analyzed is an IgG, IgM, IgA, IgE or IgD antibody. In some examples, the intact antibody analyzed is IgA1 or IgA2. In some examples, the intact antibody analyzed is IgG1, IgG2, IgG3 or IgG4.

In another example, a single antibody fragment 14 is analyzed, such as an Fab fragment or F(ab')$_2$ fragment. The single antibody fragment 14 can be one that specifically binds to a target. In one example, a plurality of distinct antibody fragments 14 are analyzed, such as a population or mixture of two or more different antibody fragments 14 (such as at least two, at least three, at least four, at least 5, at least 6, at least 7, at least 8, at least 9, at least 10, at least 20, at least 50, or at least 100 different/unique antibody fragments 14). Such a mixture of antibody fragments may all specifically bind to the same antigen, or may include populations of fragments each binding to distinct/different antigens. In some examples, the mixture of antibody fragments includes both Fab fragments and F(ab')$_2$ fragments. In some examples, the mixture of antibody fragments includes Fab fragments. In some examples, the mixture of antibody fragments includes F(ab')$_2$ fragments. In some examples, antibody fragments 14 analyzed using the disclosed methods are produced from intact antibodies 10 (see step 12).

A sample containing a plurality of the single intact antibodies 10, plurality of distinct single antibodies 10, single antibody fragment 14 or plurality of antibody fragments 14 can be analyzed. In one example, such a sample is one obtained from a subject. In some examples the sample is obtained from a mammalian subject (such as a human, non-human primate, rat, mouse or rabbit). In some examples, the sample used to obtain the antibodies or antibody fragments is a blood sample or fraction thereof (e.g., plasma, serum) or ascites fluid. In some examples, the sample is one obtained from ex vivo culturing conditions, such as a cell or tissue culture, such as an antibody or antibody fragment in a cell culture media (e.g., excreted by a cell), or one obtained from a cell in culture media (e.g., obtained following lysis or other disruption of a cell membrane).

B. Exemplary Methods of Cleaving Antibodies at the Hinge Region

In some examples, an intact antibody (such as a polyclonal antibody), is exposed to an enzyme capable of digesting or cleaving an antibody at or near the hinge, to produce antibody fragments from the intact antibody, such as Fab and F(ab')$_2$ fragments see step 12, FIG. 2A). Examples of such enzymes include papain (a thiol-type protease). In another example, the enzyme digests an intact antibody into an F(ab')2 region and a pFc' region. Examples of such antibodies include pepsin (an acid-type protease). In one example, the enzyme is ficin (a thiol-type protease), which can digest mouse monoclonal IgG1 into either F(ab')2 or Fab fragments.

In one example, the intact Ab to be cleaved is an IgG. IgG can be cleaved into one F(ab')2 fragment and numerous small peptides of the Fc portion using pepsin. The resulting F(ab')2 fragment is composed of two disulfide-connected Fab units. Pepsin is a nonspecific endopeptidase that is active at acidic pH. The Fc fragments can be separated from F(ab')2 by dialysis, gel filtration or ion exchange chromatography. IgG can be cleaved into two Fab fragments and one Fc fragment using papain. Papain is a nonspecific, thiol-endopeptidase that has a sulfhydryl group in the active site, which is used in its reduced form. In one example, the intact Ab to be cleaved is a mouse IgG. Mouse mAb IgG1 can be cleaved with ficin (a thiol-type protease) to generate F(ab')2 in the presence of 4 mM cysteine, or Fab in the presence of 25 mM cysteine.

In one example, the FabRICATOR® (IdeS) cysteine protease is used to digest IgG at a specific site below the hinge yielding F(ab')2 and Fc/2 fragments. FabRICATOR® cysteine protease can be used to digest all subclasses of human, monkey, rabbit and sheep IgG. FabRICATOR Z® cysteine protease can be used to digest mouse IgG2a and IgG3. The primary digestion site For FabRICATOR® cysteine protease is . . . CPPCPAPELLG/GPSVF . . . .

In one example, the FabALACTICA® (IgdE) cysteine protease is used to digest human IgG1 at a specific site above the hinge generating intact Fab and Fc fragments. FabALACTICA® (IgdE) cysteine protease digests human IgG1 at one specific site above the hinge (KSCDKT/HTCPPC), generating intact Fab and Fc fragments.

In one example, the GingisKHAN® cysteine protease is used to digest human IgG1 at a specific site above the hinge generating intact Fab and Fc fragments. GingisKHAN® cysteine protease digests human IgG1 at a specific site above the hinge (KSCDK/THTCPPC), generating intact Fab and Fc fragments. A second digestion site on the Fc may appear if the N-glycans are removed.

In one example, the FabULOUS® (SpeB) cysteine protease is used to digest human, mouse, rat or goat IgG1 at a specific site above the hinge generating Fab and Fc fragments. The primary digestion site on human IgG1 for FabULOUS® (SpeB) cysteine protease is . . . KTHT/CPPCPAPE . . . .

In one example, the FabRICATOR® Z (IdeZ) cysteine protease is used to digest mouse IgG2a and IgG3 at a specific site below the hinge, generating a homogenous pool of F(ab')2 and Fe fragments.

In one example, the intact Ab to be cleaved is IgM. Pepsin can be used to produce F(ab')2, Fab and Fv fragments from IgM. Trypsin can generate F(ab')2, Fab, "IgG"-type and Fc5µ fragments from IgM.

In one example, the intact Ab to be cleaved is IgA. An IgA specific serine endopeptidase protease (EC 3.4.21.7) can be used to cleave IgA1 or IgaA2 at the hinge. IgA proteases cleave proteins with the amino acid sequence N-X-Z-Pro-Pro/-Y-Pro-C, where the X in the sequence preferably is a Proline or Serine; the Y=Threonine, Serine or Alanine; and Z preferably is Arginine or Threonine.

C. Exemplary Methods of Separating Intact Antibodies or Antibody Fragments.

In some examples, the intact antibody 10 or antibody fragments 14 are exposed to an optional separation step 20. Separation 20 can include the use of methods that result in purification or isolation of unique intact antibody populations or unique/distinct antibody fragment populations. Antibody purification can include selective enrichment or specific isolation of antibodies from serum (polyclonal antibodies), ascites fluid or cell culture supernatant of a hybridoma cell line (monoclonal antibodies). Separating intact antibodies 10 or antibody fragments prior to subsequent steps can simplify downstream analysis, as it allows for individual intact antibodies or individual antibody fragments to be introduced into the mass spec. In one example, a sample to be analyzed contains a mixture of different intact antibodies 10, such as a mixture of antibodies (e.g., pAbs) that bind to the same antigen, or a mixture of intact antibodies (e.g., pAbs) that bind to different antigens. In one example, a sample to be analyzed contains a mixture of different antibody fragments 14, such as a mixture of antibody fragments that bind to the same antigen, a mixture of antibody fragments that bind to different antigens, or a mixture of antibody fragment types (such as a mixture of Fab and Fc, or F(ab')$_2$ and pFc').

Exemplary methods of separation 20 include those that separate or purify intact antibody 10 or antibody fragments 14 by mass, total charge, and hydrophobicity.

In one example, reverse phase chromatography is used for the separation 20. Resins containing varying lengths of hydrocarbon chain (C4, C8, or C18 for example) can be used to bind antibodies and antibody fragments, which can be eluted. In one example, reverse phase liquid chromatography is used for the separation 20, such as high-pressure liquid chromatography (HPLC). In such a method the mobile/liquid phase (which includes antibodies or antibody fragments) passes through columns under 10-400 atmospheric pressure, and with a high (0.1-5 cm/sec) flow rate. Components of a HPLC device are solvent depot, high-pressure pump, commercially prepared column, detector, and recorder. Duration of separation is controlled with the aid of a computerized system, and material is accrued.[

In one example, where LC is used for separation, the matrix (or column type) used for the separation, as well as the elution buffer, is selected based on the parameter being used for separation. Further, the buffer being used to elute each individual antibody 10 or antibody fragment 14 from the column is selected to vary the pH of the eluting individual intact antibody or fragment. By adjusting the pH, the individual intact antibody 10 or antibody fragment 14 can be eluted in either a denatured state (such as where the pH of the elution buffer is further from the pKa of the eluting intact antibody or antibody fragment) or closer to their native state (such as where the pH of the elution buffer is closer to the pKa of the eluting intact antibody or antibody fragment). For some antibodies and antibody fragments, higher peak resolution between individual fractions can be achieved by eluting in the denatured state. For other antibodies and antibody fragments, higher peak resolution between individual fractions can be achieved by eluting in the native state. By improving peak resolution, each eluted fraction obtained by the separation 22 containing individual intact antibodies or antibody fragments can be directly used for ionization and mass spectrometric analysis 24, allowing for more reliable and accurate mass determination.

Figure 15A:
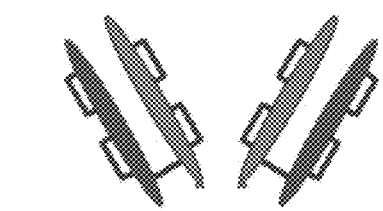
FIGS. 15A-15D. Towards polyclonal antibody analysis using ECD. Following GingisKHAN digestion of 13 different mAbs, including Herceptin, targeted analysis was performed on the resulting mixture of Fab fragments (A). After the mixture of fragments was separated using reverse phase liquid chromatography on a C4 column (B), each fragment was ionized by ESI-MS at an instrument setting of RP=15 k @m/z 200 (C). A precursor ion for the Fab fragment of Herceptin (C, marked in red) was selected for further MS/MS analysis. ECD spectra of the Fab fragment of Herceptin at an instrument setting of RP=15 k @m/z 200 was used to determine the mass of LC and Fd portions of the Herceptin Fab fragment (D).
Figure 15B:
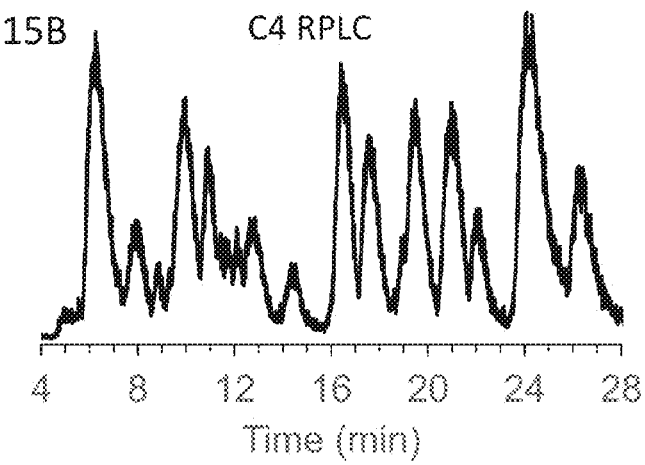
Figure 16A:
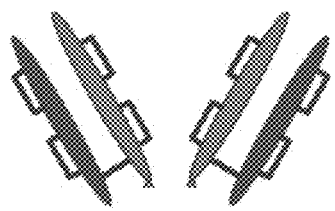
FIGS. 16A-16D. Towards polyclonal antibody analysis using UVPD. Following GingisKHAN digestion of 13 different mAbs, including Herceptin, targeted analysis was performed on the resulting mixture of Fab fragments (A). After the mixture of fragments was separated using reverse phase liquid chromatography on a C4 column (B), each fragment was ionized by ESI-MS at an instrument setting of RP=15 k @m/z 200 (C). A precursor ion for the Fab fragment of Herceptin (C, marked in red) was selected for further MS/MS analysis. UVPD spectra of the Fab fragment of Herceptin at an instrument setting of RP=15 k @m/z 200 was used to determine the mass of LC and Fd portions of the Herceptin Fab fragment (D).
Figure 16B:
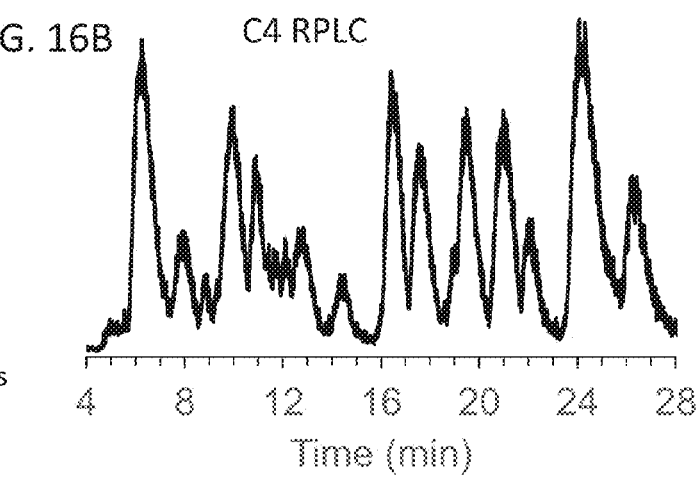

FIGS. 15B and 16B show example reverse phase LC separation of a sample containing a combination of Fab fragments from different mAbs. Separation of the individual samples was achieved over a C4 reverse phase column. Each eluting peak includes one or more Fab fragments from the combination of Fab fragments (e.g., each peak may have only one type of Fab fragment and no Fab fragments of any other type, or at least a portion of two or more types of Fab fragments from the combination of Fab fragments). Each eluting peak can then be directed into a mass spectrometer for targeted analysis.

In one example, physicochemical fractionation is used for the separation 20. Such methods result in differential precipitation, size-exclusion or solid-phase binding of immunoglobulins based on size, charge or other shared chemical characteristics of antibodies in a sample. This isolates a subset of sample proteins that includes the immunoglobulins. The main classes of serum immunoglobulins (e.g., IgG, IgM) share the same general structure, including overall amino acid composition and solubility characteristics. These general properties are sufficiently different from most other abundant proteins in serum, such as albumin and transferrin, that the immunoglobulins can be selected and enriched on the basis of these differentiating physicochemical properties. Examples of physicochemical fractionation methods that can be used include size exclusion chromatography, ammonium sulfate precipitation, immobilized metal chelate chromatography, thiophilic adsorption, and melon gel chromatography.

In one example, class-specific affinity is used for the separation 20. In such a method, solid-phase binding of a particular antibody class (e.g., IgG) by immobilized biological ligands (proteins, lectins, etc.) that have specific affinity to immunoglobulins is used. This purifies all antibodies of the target class without regard to antigen specificity. Examples of class-specific affinity methods that can be used include protein A, G, and L antibody-binding ligands, as well as IgA purification using jacalin.

In one example, antigen-specific affinity is used for the separation 20. In such a method, affinity purification of only those antibodies or antibody fragments in a sample that bind to a particular antigen molecule through their specific antigen-binding domains. This purifies all antibodies or antibody fragments that bind the antigen without regard to antibody class or isotype. Examples of antigen-specific affinity methods that can be used include those that utilize peptide antigens and affinity ligands and protein antigens and affinity ligands.

In one example, capillary electrophoresis, such as capillary gel electrophoresis, capillary isoelectric focusing, or capillary zone electrophoresis (CZE), is used for the separation 20 (see for example Espinosa-de la Garza et al., J. Vis. Exp 119:55082, 2017, herein incorporated by reference). Capillary electrophoresis (CE) is a high-performance separation technology performed using a narrow fused-silica tube (µm range) filled with a background electrolyte (BGE). Upon application of an electrical field (up to 30,000 V), charged molecules migrate towards the electrode with opposite charge (i.e., electro-driven separation). CZE can be conducted without using denaturants or solid-phase interfaces, allowing the analysis of the inherent heterogeneity of intact antibodies or antibody fragments close to their native state. CZE separation of antibodies or antibody fragments occurs inside of a fused-silica capillary covered with a hydrophilic polymer (neutral capillary) and is based on their different electrophoretic mobility, which is ruled by charge, mass, size and shape (or hydrodynamic volume). Antibodies or antibody fragments are detected when they are mobilized and pass through the detection window, which is sensed by an ultraviolet (UV) absorbance detector at 214 nm.

D. Exemplary Methods of Performing Ionization

One or more intact antibodies or antibody fragments, which may be purified or isolated (or not), are subjected to ionization to generate precursor ions. In one example, one or more intact antibodies or antibody fragments, which may be purified or isolated (or not), are subjected to electrospray ionization (ESI), thereby generating multiple charged precursor ions (step 24, FIG. 2A). ESI can result in precursor ions of the intact antibody or antibody fragment having many different positively charged states such as a +1 state, +2 state, +3 state, +10 state, +25 state, and so on. In other examples, the one or more intact antibodies or antibody fragments are subjected to matrix assisted laser desorption ionization (MALDI) to generate precursor ions. When used, MALDI generates singly charged precursor ions compared to the multiple charged ions generated by ESI.

With reference to the example discussed above in FIGS. 15B and 16B, separation may result in each of the eluting fractions (represented by peaks) shown in FIGS. 15B and 16B including only a single type of Fab fragment when starting with a combination of Fab fragments (such as Fab fragments generated from multiple different intact antibodies). Alternatively, each fraction (peak) may include Fab fragments from two or more but less than all the types of Fab fragments.

In one example, where intact antibodies or antibody fragments are separated prior to performing ESI, as they elute, each separated fraction is analyzed by ESI mass spectrometry wherein precursor ions are generated for the intact antibodies and antibody fragments present in that fraction.

E. Determining Total Mass

Intact antibodies 10 and antibody fragments 14 can be directly used for mass spectrometric analysis. The method may include performing ionization, such as ESI, on the intact antibodies or antibody fragments to generate multiple charged precursor ions 24. Alternatively, if separation and elution of the intact antibodies 10 and antibody fragments 14 was performed 20, 22, ESI may be performed on the fractions resulting from elution 22. In some examples, the ESI equipment may be coupled to LC equipment allowing for individual eluting fractions having significant separation of individual or populations of intact antibodies or individual or populations of antibody fragments to be directly electrospray ionized into a mass spectrometer. If eluting fractions do not have significant separation, individual elution peaks corresponding to the eluting fractions may be selected for ESI analysis to reduce multiplexing errors.

In one example, ESI of one or more intact antibodies 10, one or more antibody fragments 14, or the individual fractions obtained from the elution 22, generates a corresponding ESI spectra which includes m/z values for each of the multiple charged precursor ions. The ESI spectra generated for a given intact antibody 10 or antibody fragment 14 (which may be in a fraction) is used to determine the total mass of the intact antibody or total mass of the antibody fragment 26. Each mass is determined based on one or more of: (1) the m/z value of a given peak, (2) the multiple charged state of the precursor ion corresponding to the given peak, and (3) the relative distribution of other multiple charged precursor ions. In one example, the mass of the intact antibody or the mass of the antibody fragment can be determined from the m/z value of the precursor ion having a +1 charge state.

In one example, the molecular weight of an intact antibody or antibody fragment may be determined using the equation:

$$m/z=(MW+nH+)/n,$$

where m/z is the mass-to-charge ratio of a selected ion peak, MW is the molecular mass of the sample, n is the integer number of charges on the selected ion peak, and H is the mass of a proton (which is 1.008 Da).

By analyzing sets of peaks, the mass of the selected ion can be determined. For example, take a first peak for a selected precursor ion that appears at m/z 1431.6 and is assumed to have "n" charges. Further, a neighboring peak for the selected precursor ion appears at m/z 1301.4. Since the peaks are aligned in terms of their m/z, and m is constant, the series of peaks are separated by their "z" value. Thus, this second peak is assumed to have "n+1" charges. Rewriting the above equation for these two ions gives:

$$1431.6=(MW+nH+)/n \text{ and } 1301.4=[MW+(n+1)H+]/(n+1)$$

Solving these simultaneous equations and rearranging to exclude the MW term: gives n=(1301.4–H+)/(1431.6–1301.4). Therefore the number of charges on the ions at m/z 1431.6=1300.4/130.2=10. Putting the value of n back into the equation results in: 1431.6=(MW+nH+) n and therefore a mass (or molecular weight) of 14,305.9 Da (or 14.309 kDa).

Figure 15C:
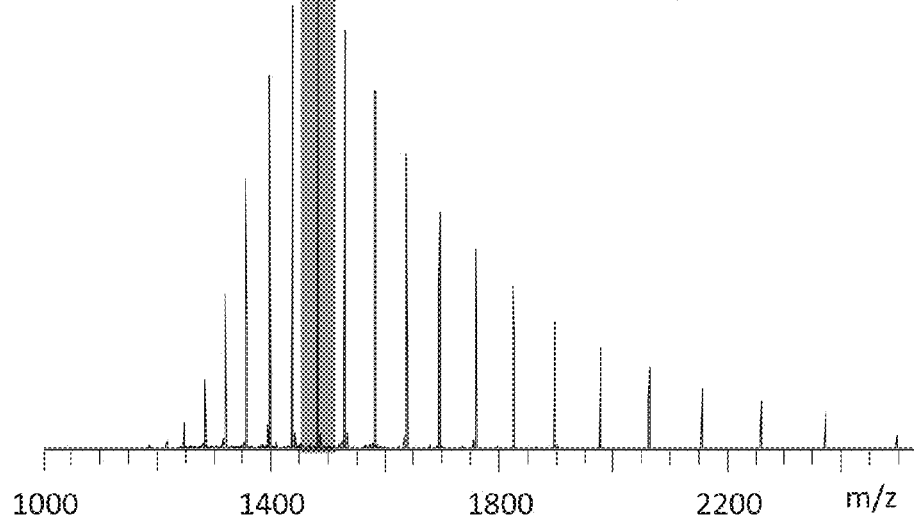
Figure 15D:
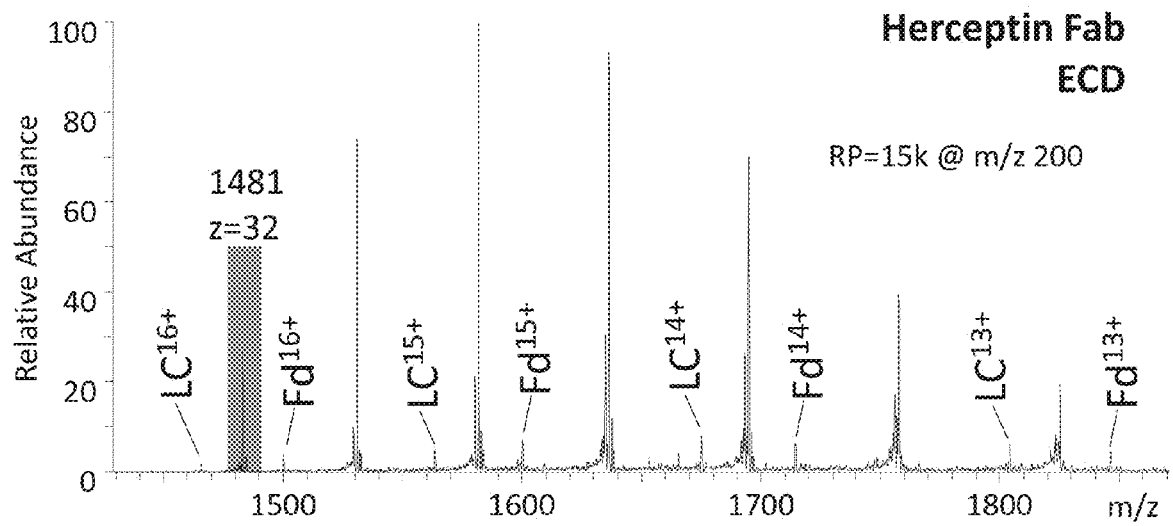
Figure 16C:
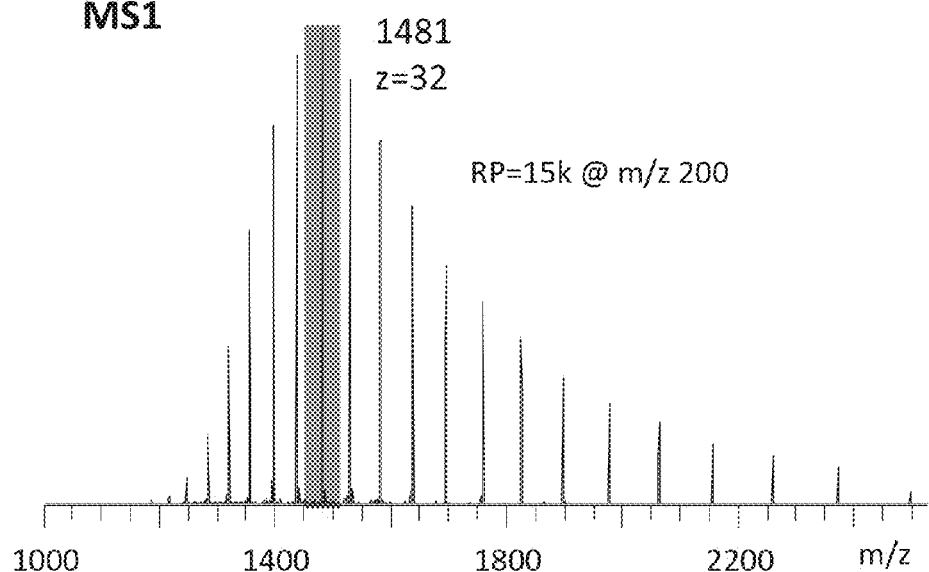
Figure 16D:
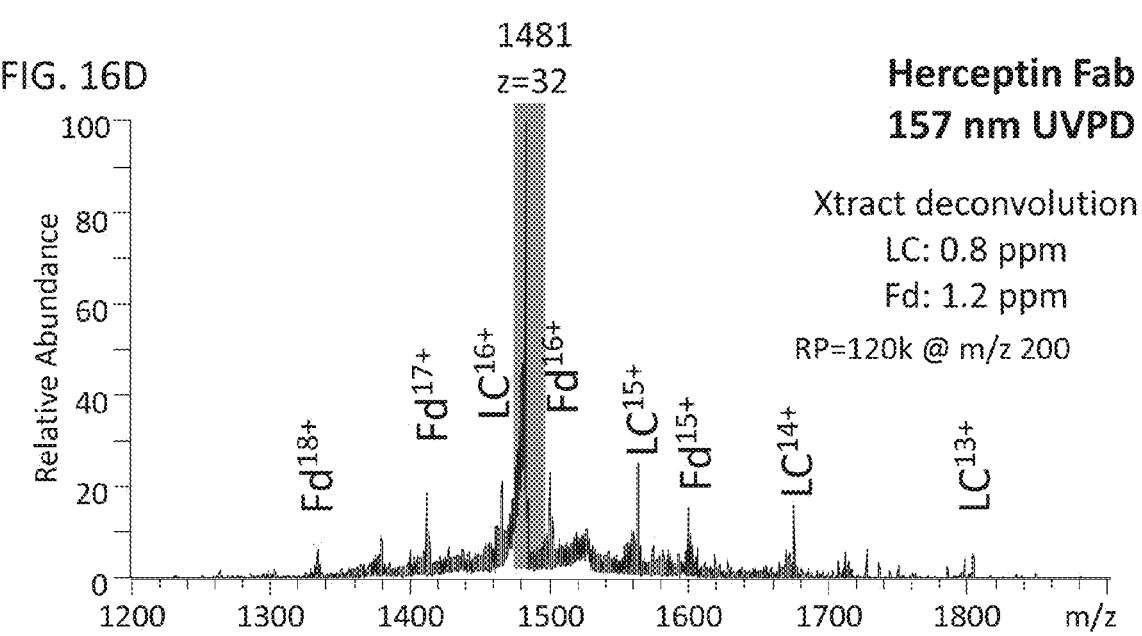

FIGS. 15B and 16B show example reverse phase LC separation of a sample containing a combination of Fab fragments from different mAbs. Separation of the individual samples is achieved over a C4 reverse phase column. The ESI spectra generated from one individual sample is shown at FIGS. 15C and 16C. Analysis of the spectra shown in FIGS. 15C, 16C is used to determine the mass of the individual antibody or antibody fragment. The mass of the selected peak is determined by using the m/z value and charge state of the peak. The charge state can be determined based on the spacing of isotopic peaks (i.e. z=1/isotope peak spacing).

F. Selecting Precursor Ion(s) for MS/MS Analysis

Ionization of an intact antibody or antibody fragment (which may or may not be purified/isolated) generates a plurality of precursor ions having a variety of multiple charge states. Each precursor ion represents an ionized version of the intact antibody or antibody fragment. A portion of the total amount of intact antibody or antibody fragment that is ionized into a precursor ion relative to the portion that remains unionized, as well as the distribution of multiple charged states of the precursor ions (that is, the abundance of precursor ions in a +1 state relative to a +2 state and so on) is determined by settings of the electrospray ionization including electrospray voltage.

In the ionization spectrum of a given intact antibody 10 or antibody fragment 14, each peak (e.g., each peak generated upon electro spray ionization of the given intact antibody or antibody fragment) represents a different precursor ion having a distinct multiple charged state. Any precursor ion, or combination of precursor ions, can be selected for further MS/MS analysis.

In one example, where the ionization spectrum (e.g., the ESI-MS spectrum) has a clear resolution of peaks, the most abundant precursor ion(s) (visible as the tallest peak(s)) is selected for MS/MS analysis. The ionization spectrum may have a clear resolution of peaks when an intact antibody or antibody fragment of only a single type is being analyzed. In one example, when antibody or antibody fragments are separated into distinct fractions prior to ionization, each analyzed fraction may generate an ionization spectrum having a clear resolution of peaks. By selecting the most abundant precursor ion(s) for further MS/MS analysis, product ions corresponding to the LC portion of the intact antibody or antibody fragment can be better identified, as discussed below.

In some examples, a distribution of precursor ions within the ionization spectrum is selected for further MS/MS analysis. Therein, a subset of all the precursor ions, or all of the precursor ions, may be selected for further MS/MS analysis. This may occur, for example, if multiple precursor ions of a given antibody or antibody fragment have similar abundance due to the nature of electrospray settings (e.g., precursor ions of the +2 state of the intact antibody are just as abundant as precursor ions of the +3 state of the intact antibody). Alternatively, this may occur due to distribution of precursor ions from multiple antibody or antibody fragment species eluting in the same fraction during the separation step 22. For example, each fraction from the separation 22 may include two or more types (or species) of intact antibody or antibody fragments resulting in an ESI spectra having multiple families of precursor ions. The distribution of precursor ions selected for MS/MS analysis 28 then includes a distribution of precursor ions for one species or type of antibody or antibody fragment from the two or more types that eluted in the same fraction.

G. Disulfide Bond Cleavage and Identification of Product Ions During MS/MS Analysis The selected precursor ions 28 are subjected to a disulfide bond dissociation or cleavage method 40, 30. That is, the method 40, 30 includes cleaving one or more disulfide bonds (such as 1, 2, 3, 4, 5, 6, 7, 8, 9, or 10 different disulfide bonds) of the selected precursor ion(s) of the intact antibody or antibody fragment 30, 40.

In examples where the methods uses a proteomic approach to determine the HC and LC chain pairing, one method can be used to cleave one or more disulfide bonds of the intact antibody or antibody fragment 40. This results in the generation of one set of MS/MS spectra. In some examples, for example when de novo sequencing is used to determine the HC and LC chain pairing, the method uses at least two different methods (such as 2, 3, 4, 5, or 6 different dissociation methods) to cleave one or more disulfide bonds of the intact antibody or antibody fragment 30. This results in at least two different sets of MS/MS spectra, each set corresponding to one of the cleavage methods used. Methods that can be used to cleave or dissociate one or more disulfide bonds of the intact antibody or antibody fragment 30, 40 include one or more of electron capture dissociation (ECD), electron transfer dissociation (ETD), electron detachment dissociation (EDD), ultraviolet photodissociation (UVPD) (for example at 266 nm, 248 nm, 213 nm, 193 nm, 157 nm, etc.), and high energy collision induced dissociation (CID).

Examples of combinations of dissociation methods 30 that can be used in de novo sequencing are shown below, along with the ions produced:

|  | Dissociation Method 1 | Dissociation Method 2 | Constant (kDa) |
|---|---|---|---|
| Example 1 | UVPD (a-ions) | ECD or ETD (c-ions) | 45.0215 |
| Example 2 | UVPD (a-ions, radical) | ECD or ETD (c-ions) | 44.0136 |

-continued

|  | Dissociation Method 1 | Dissociation Method 2 | Constant (kDa) |
| --- | --- | --- | --- |
| Example 3 | UVPD (a-ions) | CID (b-ions) | 27.9949 |
| Example 4 | UVPD (a-ions, radical) | CID (b-ions) | 26.9871 |
| Example 5 | UVPD (x-ions) | ECD or ETD (z-ions, radical) | 41.998 |
| Example 6 | UVPD (x-ions, radical) | CID (y-ions, radical) | 43.0058 |
| Example 7 | UVPD (x-ions) | CID (y-ions) | 25.9792 |
| Example 8 | UVPD (x-ions, radical) | CID (y-ions) | 26.987 |
| Example 9 | CID (y-ions) | ETD or ECD (z-ions, radical) | 16.0188 |

1. Intact Antibody

When the precursor ion is an intact antibody, during the MS/MS analysis, the disulfide bond cleavage method(s) causes fragmentation of the intact antibody and release of the LC. In one example class of the intact antibody, as shown at FIG. 1, the LC is coupled to the HC via a disulfide bond, and further, the HCs are coupled to each other via two disulfide bond. However, when the intact antibody is of a different class, there may be additional disulfide bonds coupling the HC chains to each other. During the cleavage treatment 30, 40, due to the likelihood of cleavage of one disulfide bond being higher than the cleavage of two disulfide bonds, there is a higher likelihood of release of the intact LC from the intact antibody 10, and a lower likelihood of release of the intact HC from the intact antibody. Therefore, typically, the MS/MS spectra from the intact antibody treated with any method of disulfide bond cleavage (e.g., UVPD, ECD, ETD, etc.) will generate predominantly LC product ions.

LC product ions are identified on the MS/MS spectrum based on their position relative to the precursor ion (which may be a precursor ion of an intact antibody or a precursor ion of an antibody fragment, based on the starting material). For example, due to the higher mass difference between the intact antibody and the LC, distinct peaks having a mass difference in the expected range between an average intact antibody and an average LC can be used to identify the LC product ion.

Alternatively, LC product ions are identified based on a defined distribution profile. Since cleavage of the precursor ion occurs at the location of a disulfide bond, product ions corresponding to the LC can be identified based on m/z values that have a distribution wherein product ions differ from each other by the addition or subtraction of an S atom.

By accurately identifying the intact LC product ion peak, the mass of the intact LC can be accurately determined, allowing for more a more reliable determination of the sequence of the intact LC when compared to a database of LC sequences.

2. Antibody Fragment

When the precursor ion is antibody fragment 14 (such as Fab or F(ab')$_2$ fragments), during the MS/MS analysis, the selected disulfide bond cleavage method(s) causes further fragmentation of the antibody fragment and release of the LC and Fd portions of the fragment. In the antibody fragment, as shown at FIG. 1, the LC is coupled to the variable region of the HC via a disulfide bond. The first ~220 amino acids at the N-terminal region of the HC form the Fd portion. Since this is included in the variable region of the HC, the Fd portion has a unique signature sequence tag which can be used to identify the corresponding HC. During the cleavage treatment 30, 40, cleavage of the one disulfide bond between the LC and variable region of the HC results in release of the intact LC from the intact antibody 10, as well as release of the intact Fd portion. Therefore, typically, the MS/MS spectra from the antibody fragment will generate predominantly LC and Fd product ions.

LC and Fd product ions are identified on the MS/MS spectrum based on their position relative to the precursor ion. For example, due to the smaller mass difference between the antibody Fab or F(ab')$_2$ fragment and the LC or Fd portion, distinct peaks having a mass difference in the expected range between an average antibody fragment and an average LC or Fd portion can be used to identify the LC or Fd product ions.

Alternatively, LC product ions are identified based on a defined distribution profile. Since it is known that the cleavage of the precursor ion occurs at the location of a disulfide bond, product ions corresponding to the LC can be identified based on m/z values that have a distribution wherein product ions differ from each other by the addition or subtraction of an S atom.

Similarly, Fd product ions are identified based on a defined distribution profile. Since it is known that the cleavage of the precursor ion occurs at the location of a disulfide bond, product ions corresponding to the Fd portion can be identified based on m/z values that have a distribution wherein product ions differ from each other by the addition or subtraction of an S atom.

By accurately identifying the intact LC or Fd product ion peak, the mass of the intact LC or Fd portion can be accurately determined, allowing for more a more reliable determination of the sequence of the intact LC or Fd portion when compared to a database of LC or HC sequences, respectively.

FIGS. 9, 10, 15D and 16D depict examples of identification of LC and/or Fd product ions based on their position in the MS/MS spectra relative to a corresponding precursor ion. FIGS. 5C, 6C and 14 depict examples of identification of LC and/or Fd product ions based on their relative distribution profile with the addition or removal of an S atom.

H. Determining HC-LC Chain Pairing by De Novo Sequencing

After selecting the precursor ion(s) for MS/MS analysis 28, in one example the method includes determining HC and LC pairing using de novo sequencing. In this method, the method includes cleaving one or more disulfide bonds of the intact antibody or antibody fragment using at least two different methods 30. Methods that can be used to cleave or dissociate one or more disulfide bonds of the intact antibody or antibody fragment 30 include two or more of electron capture dissociation (ECD), electron transfer dissociation (ETD), electron detachment dissociation (EDD), ultraviolet photodissociation (UVPD) (for example at 266 nm, 248 nm, 213 nm, 193 nm, 157 nm, etc.), and high energy collision induced dissociation (CID). In some examples, the two or more different methods of disulfide bond dissociation used are ECD and UVPD.

The application of two or more kinds of dissociation results in the generation of corresponding two or more sets of MS/MS spectra. Each dissociation method produces a unique ion, and the different dissociation methods are selected to generate different sets of ions.

1. Intact Antibody

When the precursor ion is intact antibody, during the MS/MS analysis, each of two or more disulfide bond cleavage methods causes fragmentation of the intact antibody and release of the LC, and a lower likelihood of release of the intact HC from the intact antibody. Therefore, typically, the MS/MS spectra from the intact antibody treated with each method of disulfide bond cleavage (e.g., UVPD, ECD, ETD, etc.) will generate predominantly LC product ions.

LC product ion peaks are identified on the MS/MS spectrum generated via each dissociation method. As discussed above, the LC product ion peaks are identified based on their position relative to the precursor ion and/or based on a defined distribution profile.

Based on the nature of the dissociation, the type of ions generated are different. Thus, for a first LC spectrum generated via a first dissociation method, a first ion type is assigned to the LC product ions. Likewise, for a second LC spectrum generated via a second dissociation method, a second ion type is assigned to the LC product ions. For example, the first dissociation method may be UVPD and accordingly a-ions of the LC product peaks are identified. Further, the second dissociation method may be ECD and accordingly c-ions of the LC product peaks are identified.

In still other examples, the dissociation device may generate b-ions (or x-, y-, or z-ions) based on the position of the bond that the given dissociation method dissociates (see FIG. 4). Accordingly, corresponding ions of the LC peaks may be identified.

The method then aligns the spectra for the LC product ions generated via the different dissociation methods so that the first set of ions for a given LC peak are aligned with the second set of ions for the given LC peak. In one example, based on the nature of the two or more dissociations selected, a-ions for the LC peaks generated in the MS/MS spectrum via use of UVPD may be compared to c-ions of the LC peaks generated in the MS spectrum via use of ECD. In other examples, a-ions of the LC peaks may be compared to b-ions of the LC peaks or b-ions may be compared to c-ions of the LC peaks. In still further examples, a-, b-, and c-ions may be compared from three different sets of spectra of LC peaks generated via three different methods of dissociation.

The spectra comparison is used to identify family of ions that are separated by a constant mass. As one example, a family of a-ions for the LC (generated via UVPD) may be identified that differ from the c-ions of the LC (generated via ECD) by a constant mass. The constant mass is a function of the nature of the dissociation and the nature of the ions. For example, when comparing a-ions to c-ions, a constant difference of 45.02 kDa may be used. As another example, when comparing a-ions to b-ions, a constant difference of 28 kDa may be used. Spectra are aligned to compare the ions having the constant mass difference. An example alignment of LC spectra having a-ions and c-ions of a constant mass difference in shown in FIG. 4.

Following alignment of at least the first set of ions and the second set of ions (when at least two methods of dissociation is used), consecutive ions of the first set and/or the second set are compared to determine the sequence of the LC product ion. For example, based on the resolution of the ion peaks, a difference between consecutive ions of the first set, second set, or both the first and second set is used to determine the LC sequence.

In one example, a difference between consecutive a-ions is used to learn a mass difference of a first amino acid in the LC, and thereby an identity of the first amino acid. In another example, a difference between consecutive c-ions is used to learn a mass difference of a first amino acid in the LC, and thereby an identity of the first amino acid.

In another example, a difference between consecutive a-ions is compared to the difference between corresponding consecutive c-ions to confirm or verify the identity of the amino acid residue. In one example, a first UVPD spectrum may not have clearly defined a-ions while the second ECD spectrum has clearly defined c-ions. In this case, the mass difference determined via the c-ions is used to learn the identity of the amino acid. In another example, a first UVPD spectrum may have clearly defined a-ions while the second ECD spectrum does not have clearly defined c-ions. In this case, the mass difference determined via the a-ions is used to learn the identity of the amino acid.

In this way, the mass difference between consecutive ions is used to determine the amino acid sequence of all or at least a portion of the product ion. In one example, the comparison is used to determine the amino acid sequence of the entire LC product ion. In other examples, at least 50% of the sequence of the LC is determined via the comparison.

The sequence of the LC is then used to query a B cell genomic sequencing database for LC sequences that match. Example databases that may be queried include IMGT (International Immunogenetics information systems), DIGIT (Database of ImmunoGlobulins with Integrated Tools) and NCBI germline V gene database. In another example, the database may be patient-specific (e.g., specific to the subject from whom the antibody was collected for analysis). The patient specific database may comprise the sequence of all B-cells extracted the subject following exposure to one or more antigens. In still another example, the database may be a sample specific database that comprises the sequence of all B-cells extracted from one or more subjects following exposure to a defined antigen. Still other custom databases may be queried. A stringency of the match may be determined based on the number of percentage of total LC sequence that is determined via de novo sequencing. For example, a higher stringency may be applied when 90% of the LC sequence is determined via de novo sequencing than when 60% of the LC sequence is determined.

Algorithms such as IgBLAST (from NCBI) can be used to query the database. In one example, the output of the algorithm includes one or more candidate LC sequences having a higher than 90% match (such as 90%, 91%, 92% 93%, 94%, 95%, 96%, 97% 98%, or 99% match) with the queried LC sequence. In one example, where the do novo sequence of the LC determined via MS/MS matches a single candidate sequence, the sequence of the corresponding LC is determined to be the sequence of the LC of the given intact antibody.

A theoretical mass of the LC corresponding to the determined sequence can be determined (e.g., calculated or retrieved from the database) and this may in turn be used to calculate the theoretical mass of the corresponding HC chain for the intact antibody. In particular, the theoretical mass of the GC of the intact antibody is determined as the difference between the mass of the intact antibody determined via ESI and the mass of the LC matching the determined de novo sequence. In some examples, in addition to or in lieu comparing the mass values, the actual MS/MS spectrum generated from the LC product ions is compared to theoretical MS/MS spectra of LC sequences available in the database.

Example software that may be used to query the database, including to calculate the theoretical mass of LC sequences in the database or to generate a theoretical MS/MS profile of an LC sequence in the database, include Sequest, Mascot, MSAmanda, ProteomeDiscoverer, and Byonic.

In some examples, the algorithm analyzes each tandem mass spectrum (MS/MS spectra of a given product ion or groups of product ions) individually and evaluates protein sequences from the database to compute the list of fragments or peptides that could result from each. The fragment's intact mass is known from the mass spectrum, and the software uses this information to determine the set of candidate sequences that could meaningfully be compared to the spectrum by including only those near the mass of the observed product ion. For each candidate peptide, the algorithm projects a theoretical tandem mass spectrum, and then compares these theoretical spectra to the observed tandem mass spectrum by the use of cross correlation. The candidate sequence with the best matching theoretical tandem mass spectrum is reported as the best identification for this spectrum.

As described below with reference to the proteomic approach, the mass of the HC is used to query a B cell genomic sequencing database for corresponding HC sequences have a theoretical mass that corresponds to the calculated HC mass (or within a threshold mass error tolerance).

Once the identity and sequence of the LC and HC pair of the intact antibody or antibody fragment is determined, the pairing of the HC and LC is learned as a function of the given epitope against which the intact antibody was selected.

2. Antibody Fragments

When the precursor ion is an antibody fragment, during the MS/MS analysis, each of two or more disulfide bond cleavage methods causes fragmentation of the antibody fragment and release of the intact LC and the Fd portion of the HC. Therefore, typically, the MS/MS spectra from the antibody fragment treated with any method of disulfide bond cleavage (e.g., UVPD, ECD, ETD, etc.) will generate LC and Fd product ions.

LC and Fd product ion peaks are identified on the MS/MS spectrum generated via each dissociation method. As discussed above, the LC and Fd product ion peaks are identified based on their position relative to the precursor ion and/or based on a defined distribution profile.

For a first LC spectrum generated via a first dissociation method, a first ion type is assigned to the LC product ions. Likewise, for a second LC spectrum generated via a second dissociation method, a second ion type is assigned to the LC product ions. For example, the first dissociation method may be UVPD and accordingly a-ions of the LC product peaks are identified. Further, the second dissociation method may be ECD and accordingly c-ions of the LC product peaks are identified.

Likewise, for a first Fd spectrum generated via a first dissociation method, a first ion type is assigned to the Fd product ions. Likewise, for a second Fd spectrum generated via a second dissociation method, a second ion type is assigned to the Fd product ions. For example, the first dissociation method may be UVPD and accordingly a-ions of the Fd product peaks are identified. Further, the second dissociation method may be ECD and accordingly c-ions of the Fd product peaks are identified.

In still other examples, the dissociation device may generate b-ions (or x-, y-, or z-ions) and the corresponding ions of the LC peaks and Fd peaks may be identified.

The method then aligns the spectra for the LC product ions generated via the different dissociation methods so that the first set of ions for a given LC peak are aligned with the second set of ions for the given LC peak, as described above. In the same manner, the spectra for the Fd product ions generated via the different dissociation methods are aligned so that the first set of ions for a given Fd peak are aligned with the second set of ions for the given Fd peak.

In one example, a-ions for the LC peaks generated in the MS/MS spectrum via use of UVPD may be compared to c-ions of the LC peaks generated in the MS spectrum via use of ECD and a-ions for the Fd peaks generated in the MS/MS spectrum via use of UVPD may be compared to c-ions of the fd peaks generated in the MS spectrum via use of ECD. In other examples, a-ions of the LC or Fd peaks may be compared to b-ions of the LC or Fd peaks or b-ions may be compared to c-ions of the LC or Fd peaks. In still further examples, a-, b-, and c-ions may be compared from three different sets of spectra for LC (or Fd) peaks generated via three different methods of dissociation.

The spectra comparison is used to identify family of ions that are separated by a constant mass. As one example, a family of a-ions for the Fd portion (generated via UVPD) may be identified that differ from the c-ions of the Fd portion (generated via ECD) by a constant mass. The constant mass is a function of the nature of the dissociation and the nature of the ions. For example, when comparing a-ions to c-ions, a constant difference of 45.02 kDa may be used. As another example, when comparing a-ions to b-ions, a constant difference of 28 kDa may be used. Spectra are aligned to compare the ions having the constant mass difference.

Following alignment of at least the first set of ions and the second set of ions (when at least two methods of dissociation is used) of the LC peaks, consecutive ions of the first set and/or the second set are compared to determine the sequence of the LC product ion. Likewise, following alignment of at least the first set of ions and the second set of ions (when at least two methods of dissociation is used) of the Fd peaks, consecutive ions of the first set and/or the second set are compared to determine the sequence of the Fd product ion. For example, based on the resolution of the ion peaks for the LC or Fd portions, a difference between consecutive ions of the first set, second set, or both the first and second set is used to determine the LC or Fd sequence, respectively.

In one example, a difference between consecutive a-ions in the Fd spectrum is used to learn a mass difference of a first amino acid in the Fd portion, and thereby an identity of the first amino acid. In another example, a difference between consecutive c-ions in the Fd portion is used to learn a mass difference of a first amino acid in the LC, and thereby an identity of the first amino acid.

In another example, a difference between consecutive a-ions is compared to the difference between corresponding consecutive c-ions of the Fd spectrum to confirm or verify the identity of the amino acid residue.

The sequence of the LC is then used to query a B cell genomic sequencing database for LC sequences that match and the sequence of the Fd portion is used to query the database for HC sequences that have a matching Fd portion. Example databases that may be queried include IMGT (International Immunogenetics information systems), DIGIT (Database of ImmunoGlobulins with Integrated Tools) and NCBI germline V gene database. A stringency of the LC match may be determined based on the percentage of total LC sequence that is determined via de novo sequencing. For example, a higher stringency may be applied when 90% of the LC sequence is determined via de novo sequencing than when 60% of the LC sequence is determined. A stringency of the Fd match may be determined based on the percentage of total Fd portion sequence that is determined via de novo sequencing. For example, a higher stringency may be applied when 90% of the Fd sequence is determined via de novo sequencing than when 60% of the Fd sequence is determined.

Algorithms such as IgBLAST (from NCBI) can be used to query the database. In one example, the output of the algorithm includes one or more candidate LC sequences (when querying the database with the de novo LC sequence) or one or more candidate HC sequences (when querying the database with the de novo Fd sequence) having a higher than 90% match (such as 90%, 91%, 92% 93%, 94%, 95%, 96%, 97% 98%, or 99% match) with the queried sequence. In one example, where the do novo sequence of the LC determined via MS/MS matches a single candidate LC sequence, the sequence of the corresponding LC is determined to be the sequence of the LC of the given antibody fragment. In one example, where the do novo sequence of the Fd portion determined via MS/MS matches a single candidate HC sequence, the sequence of the corresponding HC is determined to be the sequence of the HC of the given antibody fragment.

Once the identity and sequence of the LC and HC pair of the antibody fragment is determined, the pairing of the HC and LC is learned as a function of the given epitope against which the intact antibody (from which the antibody fragment was generated), was selected.

I. Determining HC-LC chain pairing using a database

1. Intact Antibody

Upon determination that a given product ion (or a distribution of product ions) corresponds to the LC of the intact antibody 42, the mass of the LC for the intact antibody precursor ion can be determined. The mass is determined based on the mass of the given product ion and the charge state of the product ion. Since the product ions are arranged in the spectra in terms of their m/z ratio, in one example, identification of a singly charged state (+1 state) of the product ion corresponding to the LC of the intact antibody may allow for calculation of the mass of the LC.

The mass of the LC is then used to query a B cell genomic sequencing database for corresponding LC sequences that correspond to the same mass (or within a threshold mass error tolerance) 44. Example databases that may be queried include IMGT (International Immunogenetics information systems), DIGIT (Database of ImmunoGlobulins with Integrated Tools) and NCBI germline V gene database.

Algorithms such as IgBLAST (from NCBI) can be used to query the database for intact LC sequences whose theoretical mass matches the measured mass of the LC of the intact antibody as determined via MS/MS analysis. The results are filtered to include theoretical masses that are within a threshold mass error of the queried mass. The threshold mass error tolerance, and thereby the filter stringency, may be a function of the accuracy of the mass spectrometer. For example, a higher stringency may be applied for spectrometers having an accuracy of 1 ppm while a lower stringency may be applied for spectrometers having an accuracy of 10 ppm.

The output of the algorithm includes one or more candidate LC sequences having theoretical mass values that are within the threshold error of the determined mass of the LC of the intact antibody. In one example, where the mass of the LC determined via MS/MS matches a single theoretical mass from the database, the sequence of the corresponding LC is determined to be the sequence of the LC of the given intact antibody.

In another example, where multiple candidate sequences are identified, a sequence of the variable region of the LC may be used to filter through the candidate sequences. In another example, de novo sequencing of the variable region of the LC from the intact antibody may be used to identify a single candidate sequence from the multiple candidate sequences.

In some examples, though less frequently, MS/MS analysis of the intact antibody may also enable the determination that a given product ion (or a distribution of product ions) corresponds to the HC of the intact antibody 42, and the mass of the HC for the intact antibody precursor ion can be determined from the m/z value of the product ion(s). In this case, the mass of the HC is used to query a B cell genomic sequencing database for corresponding HC sequences that correspond to the same mass (or within a threshold mass error tolerance) 44.

However, when starting with an intact antibody sample, the predominant product ions correspond to the LC since the likelihood of cleavage of two disulfide bonds in an intact antibody is lower. In such a case, the method can determine the mass of the intact HC of the intact antibody 46 based on a calculated difference between the measured mass of the intact antibody sample (as determined via ESI at 26) and the measured mass of the intact LC (as determined via MS/MS at 42). The mass of the intact HC is then used to query the B cell genomic sequencing database for HC sequences whose theoretical masses are within a threshold mass error of the queried HC mass.

The output of the algorithm includes one or more candidate HC sequences having theoretical mass values that are within the threshold error of the determined mass of the HC of the intact antibody. In one example, where the mass of the HC determined via MS/MS matches a single theoretical mass from the database, the sequence of the corresponding HC is determined to be the sequence of the HC of the given intact antibody.

In another example, where multiple candidate sequences are identified, a sequence of the variable region of the HC may be used to filter through the candidate sequences. For example, the intact antibody may be treated to generate Fab or F(ab)'$_2$ fragments and de novo sequencing of the Fd portion, in particular at the CDR of the HC (e.g., the CDR3 region for an IgG), may be used to identify a single candidate sequence from the multiple candidate sequences. Herein the CDR region of the HC includes a CDR region that is not tied up between the disulfide bonds and therefore is part of the Fd portion of the HC. For example, as shown at FIG. 1, in the case of the IgG, the CDR3 region is outside the region tied by between the disulfide bond while CDR1 and CDR2 are within the region. Therefore when the intact antibody is of the IgG type, the sequence of the CDR3 region may be used as the query for the database. In other types of antibodies, such as IgA, or IgE, an alternate CDR region, such as CDR1 or CDR2 may be used as the query for the database.

2. Antibody Fragment

Upon determination that a given product ion (or a distribution of product ions) corresponds to the LC or Fd portion of the intact antibody 42, the mass of the LC or Fd portion of the antibody fragment precursor ion can be determined. The mass is determined based on the mass of the given product ion and the charge state of the product ion. Since the product ions are arranged in the spectra in terms of their m/z ratio, in one example, identification of a singly charged state (+1 state) of the product ion corresponding to the LC of the antibody fragment may allow for calculation of the mass of the LC and identification of a singly charged state (+1 state)

of the product ion corresponding to the Fd portion of the antibody fragment may allow for calculation of the mass of the Fd portion.

Similarly, the mass of the Fd portion is used to query a B cell genomic sequencing database for corresponding LC sequences that correspond to the same mass (or within a threshold mass error tolerance) 44. Example databases that may be queried include IMGT (International Immunogenetics information systems), DIGIT (Database of Immuno-Globulins with Integrated Tools) and NCBI germline V gene database.

Algorithms such as IgBLAST (from NCBI) can be used to query the database for intact LC sequences whose theoretical mass matches the measured mass of the LC of the intact antibody as determined via MS/MS analysis. The results are filtered to include theoretical masses that are within a threshold mass error of the queried mass. The threshold mass error tolerance, and thereby the filter stringency, may be a function of the accuracy of the mass spectrometer. For example, a higher stringency may be applied for spectrometers having an accuracy of 1 ppm while a lower stringency may be applied for spectrometers having an accuracy of 10 ppm.

The output of the algorithm includes one or more candidate LC sequences having theoretical mass values that are within the threshold error of the determined mass of the LC of the antibody fragment. In one example, where the mass of the LC determined via MS/MS matches a single theoretical mass from the database, the sequence of the corresponding LC is determined to be the sequence of the LC of the given antibody fragment.

In another example, where multiple candidate sequences are identified, a sequence of the variable region of the LC may be used to filter through the candidate sequences. In another example, de novo sequencing of the variable region of the LC from the antibody fragment may be used to identify a single candidate sequence from the multiple candidate sequences.

Similarly, the mass of the Fd portion is used to query a B cell genomic sequencing database for corresponding HC sequences whose Fd portions (generated via the algorithm from the database of HC sequences) correspond to the same mass (or within a threshold mass error tolerance) 44. Algorithms such as IgBLAST (from NCBI) can be used to query the database for Fd fragments generated from known HC sequences whose theoretical mass matches the measured mass of the Fd portion of the antibody fragment as determined via MS/MS analysis. The results are filtered to include theoretical masses that are within a threshold mass error of the queried mass. The threshold mass error tolerance, and thereby the filter stringency, may be a function of the accuracy of the mass spectrometer.

The output of the algorithm includes one or more candidate HC sequences having Fd portions whose theoretical mass values are within the threshold error of the determined mass of the Fd portion of the antibody fragment. In one example, where the mass of the Fd portion determined via MS/MS matches a single theoretical mass from the database, the sequence of the corresponding HC is determined to be the sequence of the HC of the given antibody fragment.

In another example, where multiple candidate sequences are identified, a sequence of the variable region of the HC may be used to filter through the candidate sequences. In another example, de novo sequencing of the Fd portion of the antibody fragment, particularly in the CDR3 region, may be used to identify a single candidate HC sequence from the multiple candidate sequences.

Thus, for an intact antibody, the LC identity is directly determined based on the mass of the LC product ion calculated from the MS/MS spectrum of the LC product ion. In comparison, the HC identity is typically determined by indirectly estimating the mass of the HC product ion from the mass of the intact antibody relative to the mass of the LC.

For an antibody fragment, the LC identity is directly determined based on the mass of the LC product ion calculated from the MS/MS spectrum of the LC product ion. The HC identity is also directly determined based on the mass of the Fd product ion calculated from the MS/MS spectrum of the Fd product ion.

Once the identity and sequence of the LC and HC pair of the intact antibody or antibody fragment is determined, the pairing of the HC and LC is learned as a function of the given epitope against which the intact antibody or antibody fragment was selected. In one example, the determined LC-HC chain pairing is applied for the development of therapeutic mAbs for the given epitope.

Example 1

Materials and Methods

This example describes the materials and methods used to generate the results described in Example 2 and 3 below.

Materials

FabRICATOR® and GingisKHAN® enzymes were from Genovis Inc. (Cambridge, Mass., USA) and were used following the manufacturer's protocols. Trastuzumab (Herceptin, Genentech, Inc., South San Francisco, Calif., USA) was reconstituted in phosphate buffered saline. Intact mAbs or mAb fragments were buffer exchanged into 100 mM ammonium acetate using Amicon Ultra 0.5 mL 10 kDa centrifugal molecular weight cutoff filters (Sigma-Aldrich, St. Louis, Mo., USA). Working solution of intact mAb or mAb fragments were prepared at 0.1 mg/mL in 100 mM ammonium acetate. All other chemicals and supplies were from Fisher Scientific (Fairlawn, N.J., USA).

Mass Spectrometry

Experiments were performed using a modified Q Exactive HF/UHMR Orbitrap mass spectrometer (Thermo Fisher Scientific, Bremen, Germany) modified to enable UVPD and ECD similar to what has been previously described.[36] The charge detector was removed from the end of the HCD cell to allow irradiation of the HCD cell trapping volume from the rear of the mass spectrometer. Mass selected precursor ions were transferred to the HCD cell with a collision energy of 5 eV/q and stored in the HCD cell during UVPD MS/MS acquisitions for a period of time sufficient for a user defined number of laser pulses. A pulse generator (Berkeley Nucleonics, San Rafael, Calif., USA) produced a 30 µs pulse to trigger each 5 ns laser pulse at a repetition rate of 500 Hz. A TTL pulse was used to gate the pulse generator on for the desired number of laser pulses. 157 nm or 193 nm photons were generated by a $F_2$ or ArF excimer laser (Excistar XS 500, Coherent Inc., Santa Clara, Calif., USA), respectively. A CF16 quartz window was added to the rear flange of the mass spectrometer vacuum chamber on axis with the HCD cell for 193 nm UVPD. For 157 nm UVPD, the output of the laser was coupled directly to the vacuum system of the mass spectrometer. The output flange of the 157 nm laser was adapted to a standard KF25 vacuum flange. A duplicate rear flange for the mass spectrometer was made and incorporated a KF25 flange on axis with the HCD cell. A flexible stainless vacuum tube was used to couple to the laser output to the mass spectrometer vacuum chamber. Supplemental activation after UVPD was provided to the remaining precursor and product ions during the transfer of ions from the HCD cell to the C-trap. This was achieved by raising the HCD cell offset relative to the C-trap which was held at 0 V. Due to the small dimensions of the C-trap, trapping efficiency in the C-trap dropped significantly with HCD cell offset greater than ~25V. The C-trap exit lens was biased 1-2 V less than the HCD cell offset ECD was performed using an electro-magnetostatic ExD cell (e-MSion Inc, Corvallis, Oreg., USA). The ExD cell replaced the small transmission octa-pole between the mass selective quadrupole and the C-trap. Electrons were emitted from a 0.75 mm diameter filament loop with 1.2 A heating current. Electron capture higher energy collision dissociation (EChcD) was performed by accelerating ECD products into the HCD cell after passing through the ExD cell. Typical collision energy for EChcD was 50-100 eV/q.

Static nano-electrospray ionization was performed using glass capillary emitters with a 2 μm tip (GlassTip; New Objective, Inc., Woburn, Mass., USA). A stainless steel union with a platinum wire were used to hold the capillary and apply the electrospray voltage directly to the analyte solution. Typical electrospray voltage was 900 V. An in-source trapping potential of 100 V was used for desolvation and unfolding of protein ions in the source region of the mass spectrometer. An inlet capillary temperature of 300° C., S-lens RF of 80, and a fixed ion injection time of 50-200 ms was used for all experiments. Precursor ions were mass selected with an isolation width of 10-20 m/z, and mass analysis was performed with a resolving power of 240,000 at m/z 200. Approximately five minutes of averaging was used to produce MS/MS spectra for direct infusion experiments.

MS/MS spectra were annotated using LCMS Spectator with a signal-to-noise ratio threshold of 3, isotopic fit of 0.7, and mass tolerance of 5 ppm. The Xtract deconvolution algorithm as part of Xcalibur version 3.0.63 (Thermo Fisher Scientific Inc.) was used for spectral deconvolution.

Example 2

Identification of Trastuzumab Light Chain and Heavy Chain Pairing

An EChcD spectrum of the 25+ charge state of Trastuzumab is shown in FIG. 5C. In-source trapping potential of 100 V was used along with 80 eV/q HCD collision energy after ECD. This set of conditions yielded abundant c/z-ions and relatively few b/y-ions corresponding to peptide backbone cleavage of both the HC and LC. Additionally, an abundant charge state distribution for the intact LC was observed as a result of cleavage of the intermolecular disulfide bond with the HC. Intact HC was not observed likely due to the required cleavage of three disulfide bonds to liberate a HC. An inset in the EChcD spectrum in FIG. 5C shows the characteristic triplet of species associated with disulfide bond cleavage and confirms disulfide bond cleavage has occurred. Competition between cleavage of the S—S and C—S bonds yielded LC (i.e. R—C—SH) as wells as LC plus or minus a sulfur. Mass measurement accuracy of 0.4 ppm was achieved for the intact LC. 5 ppm mass tolerance was used for product ion assignments to minimize to likelihood of false annotations and the assignment of multiple product ions to the same isotopic distributions in these multiplexed spectra. Native charge state precursor ions combined with the charge neutralization of the ECD process yielded product ions spread over a 4000 m/z range. FIGS. 5A and 5B show product ions maps for the HC and LC, respectively. Overall, 42% coverage was achieved for the LC and 20% for the HC. For both chains the product ions are generally concentrated in the regions between disulfide bridges and at the termini of the chains. Branched product ions were not considered in this study. Complete sequence coverage was achieved for the CDR3 of the HC while two missed cleavages N-terminal to proline residues were observed in the LC CDR3.

De Novo Sequencing Using Complementary Pairs of Ions

Figure 7A:
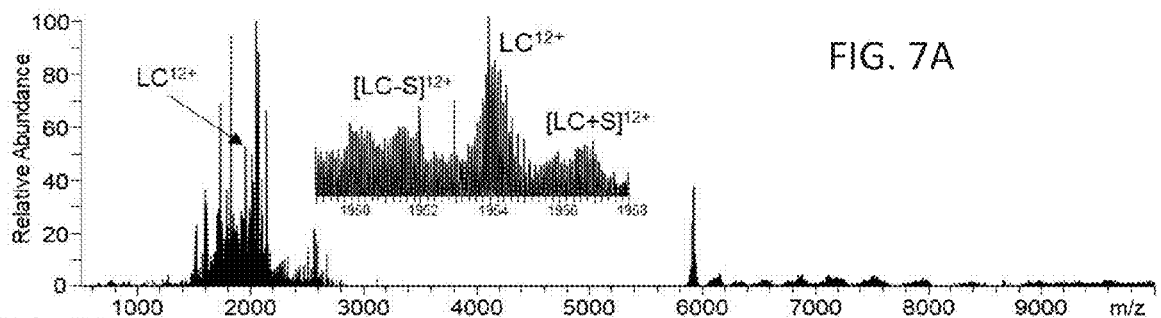
FIGS. 7A-7C. 193 nm UVPD spectrum (A) of the 25+ charge state of Trastuzumab acquired using four laser pulse at 0.3 mJ per pulse and product ion maps for the light chain (B) and heavy chain (C). 193 nm UVPD yielded 37% and 16% sequence coverage for the light chain and heavy chain, respectively. Yellow highlight shows CDR3 for each chain.
Figure 7B:
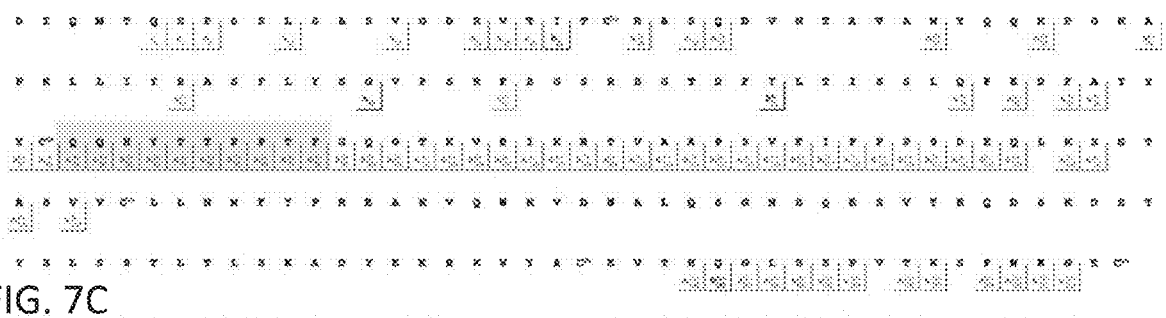
Figure 7C:
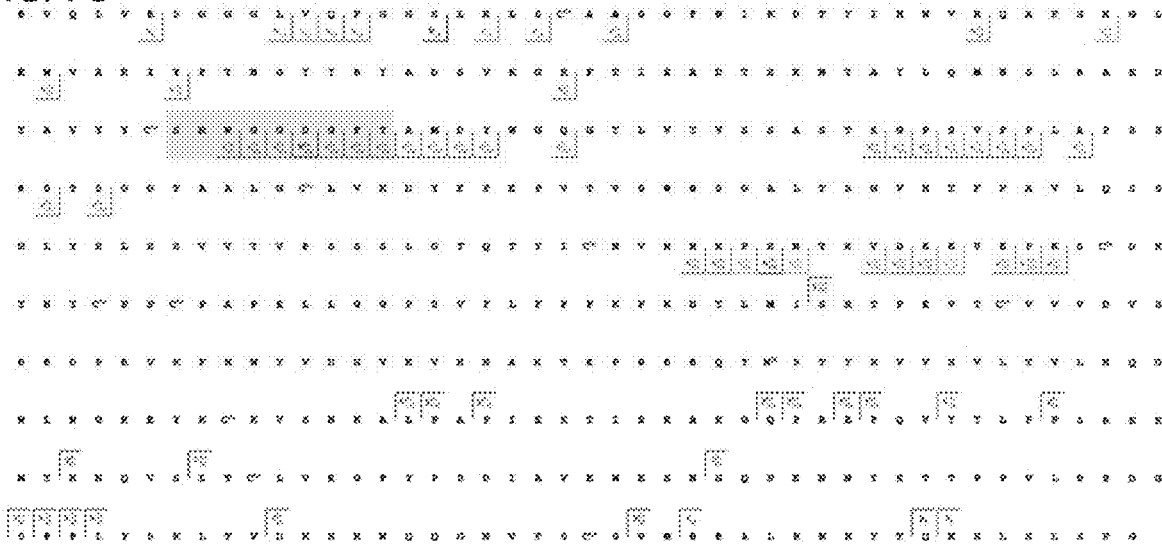

De novo sequencing using "golden" complementary pairs of ions [10, 39, 40], was performed using 157 nm UVPD [19]. 157 nm UVPD predominantly yields a/x-ions; however, relative to other short wavelength UV photons, 157 nm showed more specificity for disulfide bonds cleavage. FIG. 6C shows 157 nm UVPD results for Trastuzumab electro-sprayed under native conditions with all disulfide bonds intact. Two laser pulses at 1 mJ/pulse were used and ions were transferred from the HCD cell to the C-trap with 20 eV/q collision energy. As with EChcD, backbone cleavage product ions for both the HC and LC are predominantly located between the regions containing disulfide bridges (FIGS. 6A and 6B). Complete coverage of the LC CDR3 is achieved with a-ions and only a single missed cleavage was observed in the region between disulfide bonds. Two missed cleavages were observed in the HC CDR3. The major contrast between EChcD and UVPD is the absence of charge reduction in both the precursor and product ions for UVPD. Consequently, UVPD product ions are spread over a much narrower m/z range (FIG. 6C). Overall, 157 nm yielded 32% sequence coverage for the LC and 17% for the HC. One of the most abundant product ions in the 157 nm UVPD spectrum is the 13+ charge state of the intact LC resulting from cleavage of the intermolecular disulfide bond between LC and the HC. The additional collision energy during ion transfer from the HCD cell to C-trap increased the yield of intact LC. This is presumably a result of dissociation of noncovalent interactions or mobilized radicals/H atoms within product ions yielding additional disulfide bond cleavage. An inset in FIG. 6C shows the isotopic distributions of the intact LC (i.e., R—C—S'; 0.8 ppm mass error) and LC plus or minus sulfur. 157 nm also produced a relatively abundant species corresponding the loss of $CO_2$ from the intact LC that was not observed with EChcD. The loss of CO2 was not observed in significant abundance from other product ions (e.g. a/x-ions). FIGS. 7A-7C contains 193 nm UVPD data for native intact Trastuzumab.

The experimental conditions used (see Example 1) were optimized to maximize yield for the intact LC. MS/MS conditions utilizing different ECD cell tuning, UVPD parameters, or supplemental collisional activation can significantly alter the yield of intact LC. MS/MS parameters utilized herein were relatively "soft" to minimize secondary dissociation of the intact LC. Nevertheless, sequence coverage is comparable to or better than previously published values for a single experimental condition.

Figure 8:
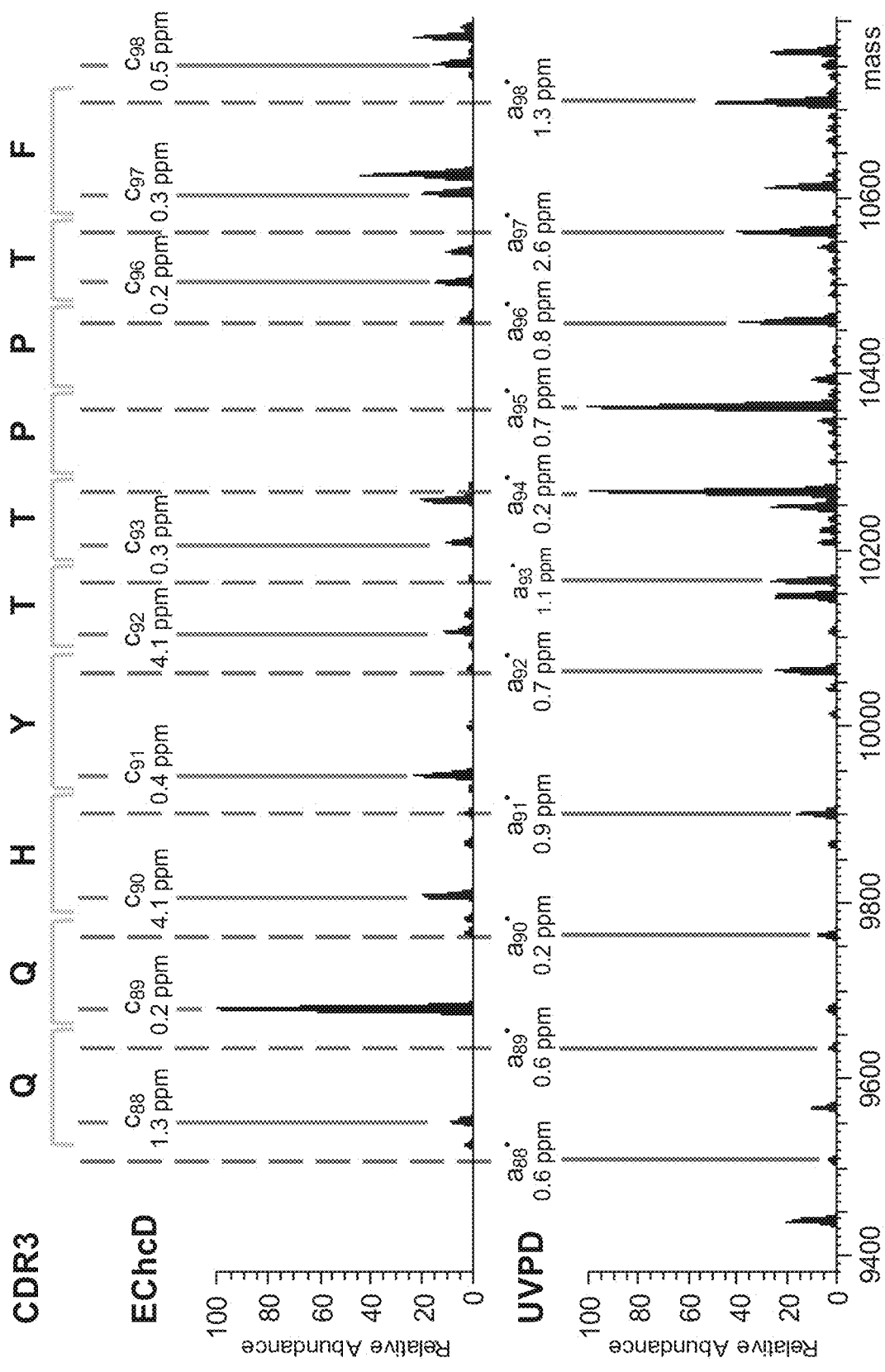
FIG. 8. Complementary ion pairs from EChcD and 157 nm UVPD can be used to enhance de novo sequencing capabilities of antibody complementarity determining regions. Zoomed in Xtract decharged spectra produced by EChcD with 80 eV/q collision energy (top) and 157 nm UVPD with (two 1 mJ pulses and 20 eV/q collision energy during transfer from the HCD cell to the C-trap; bottom) of the 25+ and 27+ charge states, respectively, of intact Trastuzumab. Product ion mass measurement accuracy calculated based on neutral monoisotopic mass generated by Xtract.

FIG. 8 demonstrates the ability to use "golden" complementary ion pairs [10] to de novo sequence the CDR3 of the LC. EChcD yielded a series of c-ions spanning the entire CDR3, except two N-terminal to proline cleavages, and 157 nm UVPD yielded a complete series of a-ions. Very high mass accuracy was observed for the neutral monoisotopic masses of the a-ion and c-ion series. The fixed mass difference between a-ions and c-ions at the same residue (e.g., 44.0136 Da as shown in the table above) enables alignment of the spectra and determination of residues based on the spacing of pairs of a/c-ions. EChcD and 157 nm UVPD yielded complete coverage of the heavy chain CDR3 and thus the ability for complete de novo sequence determination as well.

These results demonstrate the capability to generate all the information required for determination of chain pairing from native intact Trastuzumab with both EChcD and 157 nm UVPD. Efficient cleavage of intermolecular disulfide bonds enabled sub-ppm mass measurement accuracy for intact LC. Additionally, extensive sequence coverage of regions between intramolecular disulfide bonds of the HC and LC enabled confirmation of the CDR3 regions. However, when moving to online analyses of antibody mixtures, smaller antibody fragments that retain all of the required information for the determination of chain pairing can be used. Additionally, removal of the constant region of the heavy chain may improve separation efficiency and thus depth of coverage.

Figure 9:
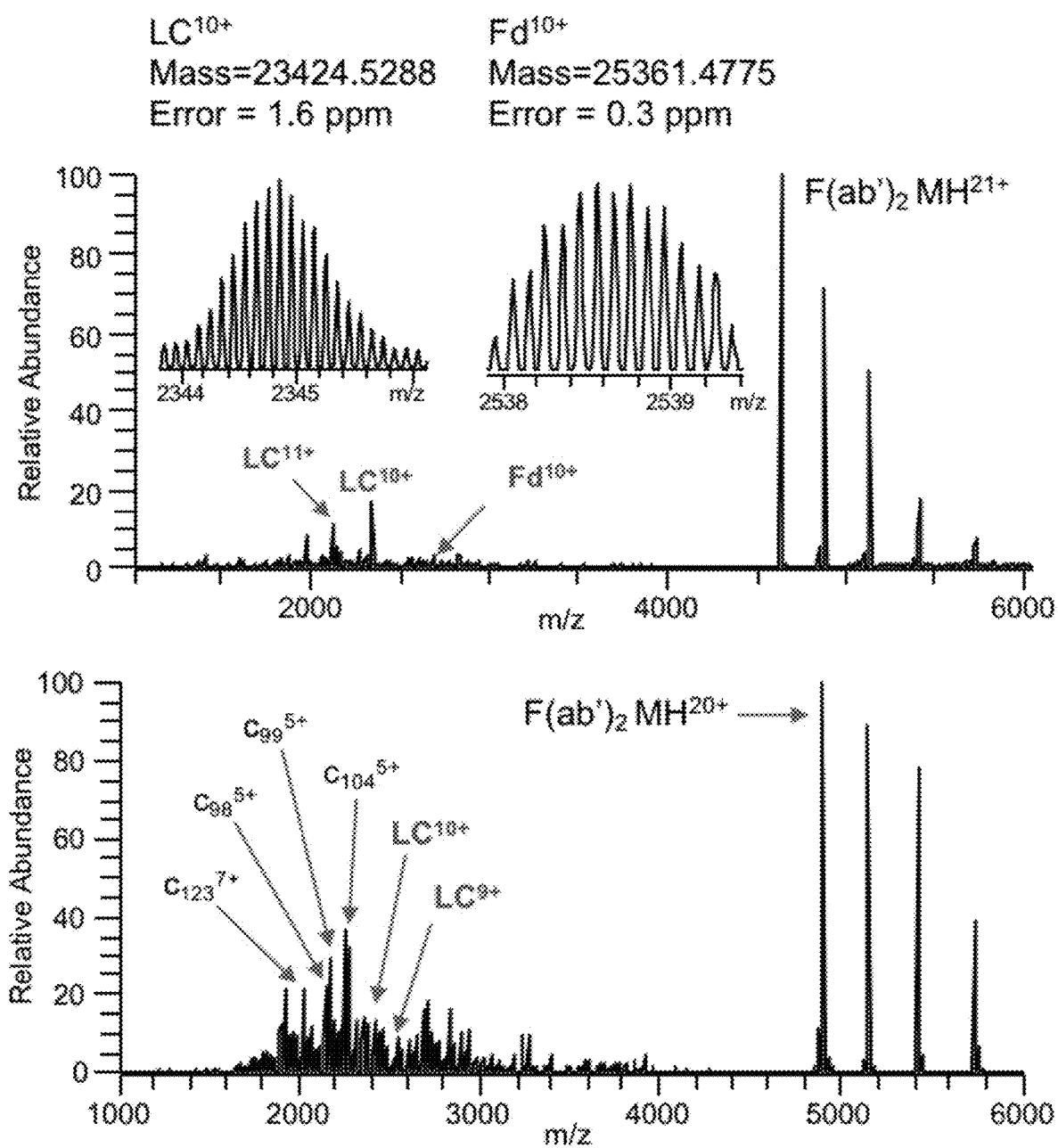
FIG. 9 EChcD spectra of the F(ab')2 fragment of Trastuzumab. The top spectrum was acquired with ExD setting that yielded less efficient ECD. The bottom spectrum was acquired with ExD cell setting that yielded more efficient ECD and secondary dissociation of the free LC and Fd chains. The Fd subunit was not observed in the bottom spectrum.

Many enzymes are available to cleave antibodies below or above the inter-HC disulfide bonds in the hinge region. Cleavage below the hinge region with IdeS® enzyme yields the $F(ab')_2$ fragment, while cleavage above the hinge region with GingisKHAN® enzyme yields the Fab fragment. Three disulfide bonds are cleaved in order to observe the intact Fd subunit from a $F(ab')_2$ fragment. For the Fab fragment, a single disulfide bond is cleaved to yield the intact LC and Fd subunit. This makes the Fab fragment an attractive target for the determination of chain pairing. FIG. 9 contains data for EChcD of the F(ab')2 fragment. Intact LC and Fd were observed, but the Fd was very low abundance due to the low probability of cleaving three disulfide bonds. This workflow was not pursued further due to the benefits associated with a workflow utilizing the Fab fragment.

FIGS. 10A-10B show EChcD and 157 nm UVPD spectra of the Fab fragment of Trastuzumab under native-like conditions with all disulfide bonds intact. EChcD yielded abundant intact LC and Fd subunit as a result of intermolecular disulfide bond cleavage. Both chains were observed in fairly broad charge state distributions. The 9+ and 5+ charge states were the most abundant for the Fd and light chain respectively; when combined, they yield the precursor charge state after a single electron capture event. Likewise, 157 nm UVPD yielded intact Fd subunit and LC. However, the Fd subunit and LC were observed in almost exclusively a single charge state, the 9+ and 6+ charge states, respectively, and combine to give the precursor charge state. For reference, the 9+ charge state of the Fd subunit in the 157 nm UVPD spectrum is twice as abundant in absolute intensity as in the EChcD spectrum with equivalent acquisition parameters. Product ion maps illustrating sequence coverage for the Fd and LC subunits are shown in (FIGS. 11A-11B, 12A-12B, 13A-13B).

Neutral losses of small molecules and amino acid side chains are very common in both electron-based and high-energy photon-based MS/MS methods. Abundant neutral losses from the intact chains after disulfide bond cleavage have the potential to interfere with determination of accurate masses due to overlapping isotopic distributions. FIGS. 14A-14D show zoomed in portions of the intact Fd subunit and light chain produced by EChcD and 157 nm UVPD of the Trastuzumab Fab fragment. EChcD predominantly exhibited the expected competition between S—S and C—S bond cleavage as well as lesser amounts of water or ammonia loss. 157 nm UVPD yielded a significant amount of C—S bond cleavage as wells as $CO_2$ loss. The gain or loss of sulfur and neutral loss of $CO_2$ are relatively large mass shifts. This combined with the relatively wide spacing of product ion isotopic distributions due to working with native-like precursor charge states minimized interferences caused by these species. Additional radical directed neutral losses are expected, but the extent and type of neutral losses observed may vary based on surrounding amino acid sequence and the higher order structure of the ions.

Example 3

Identification of Light Chain and Heavy Chain Pairing of an Intact Ab or Ab Fragment of Unknown Sequence Determining chain pairing of an antibody or antibody fragment with an unknown sequence can follow the methods used in Examples 1-2 above. The unknown antibody or antibody fragment can be pure or part of a mixture (e.g., a mixture of polyclonal antibodies or antibody fragments) and in intact form or as a fragment, such as the Fab or F(ab)2 fragment. The unknown antibody or antibody fragment is ionized and subject to MS/MS to yield product ion(s) resulting from the cleavage of disulfide bonds linking the chains as well as the polypeptide backbone. Product ions corresponding to the intact heavy chain, light chain, or Fd fragment can be identified as a triplet of peaks corresponding to the intact chain and two peaks corresponding to the loss or gain of sulfur during disulfide bond cleavage as shown in FIGS. 5C, 6C, and 7A. For an intact antibody, the heavy chain and light chain masses, using an IgG1 for example, are readily differentiated as the masses are significantly different, ~50 kDa and ~25 kDa respectively. The masses of the light chain and Fd from an antibody fragment are not as easily differentiated due to both having a mass of ~25 kDa. Due to the conserved nature of antibody sequences and structures, product ions corresponding to the complementarity determining regions (CDRs) will be in the same mass range. Using an IgG1 for example, product ions corresponding to polypeptide backbone cleavage in the CDR3 will be in the mass range of roughly 9-12 kDa. This enables differentiation of product ions corresponding to CDRs from other parts of the antibody or antibody fragment. The CDR sequences could be determined by de novo sequencing as demonstrated in FIG. 8 or by comparison to theoretical MS/MS spectra generated from sequence databases. The combination of intact antibody/fragment mass, heavy chain/Fd mass, light chain mass, and CDR sequence enables identification and validation of the chain sequences selected from a database and determination of chain pairing for the unknown antibody.

FIGS. 15A-15D and 16A-16D show results for a mixture of antibodies Fab fragments analyzed using ECD and UVPD, respectively. The mixture of 13 Fab fragments was separated by C4 reversed phase liquid chromatography online with mass spectrometry analysis. The eluting Fab fragments were subject to precursor ion selection and MS/MS to cleave the disulfide bonds linking the LC and Fd chains and produce product ions in the CDRs. Herceptin was a component of the mixture and was used to exemplify the process.

REFERENCES (1) Bornholdt et al., Isolation of Potent Neutralizing Antibodies from a Survivor of the 2014 Ebola Virus Outbreak. Science 2016, 351 (6277), 1078-1083. https://doi.org/10.1126/science.aad5788.
(2) Smith et al., Human Monoclonal Antibodies Derived From Memory B Cells Following Live Atten-uated Dengue Virus Vaccination or Natural Infection Exhibit Similar Characteristics. J. Infect. Dis. 2013, 207 (12), 1898-1908. https://doi.org/10.1093/infdis/jit119.
(3) Cheung et al., A Proteomics Approach for the Identification and Cloning of Monoclonal Antibodies from Serum. Nat. Biotechnol. 2012, 30 (5), 447-452. https://doi.org/10.1038/nbt.2167.
(4) Sato et al., Proteomics-Directed Cloning of Circulating Antiviral Human Monoclonal Antibodies. Nat. Biotechnol. 2012, 30 (11), 1039-1043. https://doi.org/10.1038/nbt.2406.
(5) Guthals et al., Shotgun Protein Sequencing with Meta-Contig Assembly. Mol. Cell. Proteomics 2012, 11 (10), 1084-1096. https://doi.org/10.1074/mcp.M111.015768.
(6) Guthals et al., Sequencing-Grade De Novo Analysis of MS/MS Triplets (CID/HCD/ETD) From Overlapping Peptides. J. Proteome Res. 2013, 12 (6), 2846-2857. https://doi.org/10.1021/pr400173d.
(7) Guthals et al., De Novo MS/MS Sequencing of Native Human Antibodies. J. Proteome Res. 2017, 16 (1), 45-54. https://doi.org/10.1021/acs.jproteome.6b00608.
(8) Bradbury et al., When Monoclonal Antibodies Are Not Monospecific: Hybridomas Frequently Express Additional Functional Variable Regions. mAbs 2018, 10 (4), 539-546. https://doi.org/10.1080/19420862.2018.1445456.
(9) Georgiou et al., The Promise and Challenge of High-Throughput Sequencing of the Antibody Repertoire. Nat. Biotechnol. 2014, 32 (2), 158-168. https://doi.org/10.1038/nbt.2782.
(10) Horn et al., Automated de Novo Sequencing of Proteins by Tandem High-Resolution Mass Spectrometry. Proc. Natl. Acad. Sci. U.S.A. 2000, 97 (19), 10313-10317.
(11) Liu et al., De Novo Protein Sequencing by Combining Top-Down and Bottom-Up Tandem Mass Spectra. J. Proteome Res. 2014, 13 (7), 3241-3248. https://doi.org/10.1021/pr401300m.
(12) Vyatkina et al., De Novo Sequencing of Peptides from Top-Down Tandem Mass Spectra. J. Proteome Res. 2015, 14 (11), 4450-4462. https://doi.org/10.1021/pr501244v.
(13) Vyatkina et al., Top-down Analysis of Protein Samples by de Novo Sequencing Techniques. Bioinformatics 2016, 32 (18), 2753-2759. https://doi.org/10.1093/bioinformatics/btw307.
(14) Vyatkina, K. De Novo Sequencing of Top-Down Tandem Mass Spectra: A Next Step towards Retrieving a Complete Protein Sequence. Proteomes 2017, 5 (4), 6. https://doi.org/10.3390/proteomes5010006.
(15) Srzentić et al., Multiplexed Middle-Down Mass Spectrometry as a Method for Revealing Light and Heavy Chain Connectivity in a Monoclonal Antibody. Anal. Chem. 2018, 90 (21), 12527-12535. https://doi.org/10.1021/acs.analchem.8b02398.
(16) Bookwalte et al., Bond-Selective Photodissociation of Aliphatic Disulfides. J. Am. Soc. Mass Spectrom. 1995, 6 (9), 872-876.
(17) Chrisman et al., SO2-. Electron Transfer Ion/Ion Reactions with Disulfide Linked Polypeptide Ions. J. Am. Soc. Mass Spectrom. 2005, 16 (7), 1020-1030. https://doi.org/10.1016/j.jasms.2005.02.010.
(18) Zubarev et al., Electron Capture Dissociation of Gaseous Multiply-Charged Proteins Is Favored at Disulfide Bonds and Other Sites of High Hydrogen Atom Affinity. J. Am. Chem. Soc. 1999, 121 (12), 2857-2862. https://doi.org/10.1021/ja981948k.
(19) Fung et al., Facile Disulfide Bond Cleavage in Gaseous Peptide and Protein Cations by Ultraviolet Photodissociation at 157 Nm. Angew. Chem. Int. Ed. 2005, 117 (39), 6557-6561. https://doi.org/10.1002/ange.200501533.
(20) Gunawardena et al., Electron Transfer Dissociation of Multiply Protonated and Fixed Charge Disulfide Linked Polypeptides. Int. J. Mass Spectrom. 2007, 265 (2-3), 130-138. https://doi.org/10.1016/j.ijms.2007.01.017.
(21) Kalli, A.; Hakansson, K. Preferential Cleavage of SS and CS Bonds in Electron Detachment Dissociation and Infrared Multiphoton Dissociation of Disulfide-Linked Peptide Anions. Int. J. Mass Spectrom. 2007, 263 (1), 71-81. https://doi.org/doi: DOI: 10.1016/j.ijms.2007.01.001.
(22) Agarwal et al., Direct Elucidation of Disulfide Bond Partners Using Ultraviolet Photodissociation Mass Spectrometry. Anal. Chem. 2011, 83 (17), 6455-6458.
(23) Liu et al., Facilitating Protein Disulfide Mapping by a Combination of Pepsin Digestion, Electron Transfer Higher Energy Dissociation (EThcD), and a Dedicated Search Algorithm SlinkS. Mol. Cell. Proteomics 2014, 13 (10), 2776-2786. https://doi.org/10.1074/mcp.O114.039057.
(24) Wongkongkathep et al., Enhancing Protein Disulfide Bond Cleavage by UV Excitation and Electron Capture Dissociation for Top-down Mass Spectrometry. Int. J. Mass Spectrom. 2015, 390, 137-145. https://doi.org/10.1016/j.ijms.2015.07.008.
(25) Fort et al., Exploring ECD on a Benchtop Q Exactive Orbitrap Mass Spectrometer. J. Proteome Res. 2018, 17, 926-933. https://doi.org/10.1021/acs.jproteome.7b00622.
(26) Bonner et al., Simplified Identification of Disulfide, Trisulfide, and Thioether Pairs with 213 Nm UVPD. Analyst 2018, 143 (21), 5176-5184. https://doi.org/10.1039/C8AN01582A.
(27) Quick et al., Characterization of Disulfide Linkages in Proteins by 193 Nm Ultraviolet Photodissociation (UVPD) Mass Spectrome-try. Anal. Chem. 2018, 90 (14), 8523-8530. https://doi.org/10.1021/acs.analchem.8b01556.
(28) Ganisl, B.; Breuker, K. Does Electron Capture Dissocia-tion Cleave Protein Disulfide Bonds? CHEMISTRYOPEN 2012, 1 (6), 260-268. https://doi.org/10.1002/open.201200038.
(29) Bean, M. F.; Can, S. A. Characterization of Disulfide Bond Position in Proteins and Sequence Analysis of Cystine-Bridged Peptides by Tandem Mass Spectrometry. Analytical Biochemistry 1992, 201 (2), 216-226. https://doi.org/10.1016/0003-2697(92)90331-Z.
(30) Schnaible et al., Screening for Di-sulfide Bonds in Proteins by MALDI In-Source Decay and LIFT-TOF/TOF-MS. Anal. Chem. 2002, 74 (19), 4980-4988. https://doi.org/10.1021/ac025807j.
(31) Nicolardi et al., Structural Analysis of an Intact Monoclonal Anti-body by Online Electrochemical Reduction of Disulfide Bonds and Fourier Transform Ion Cyclotron Resonance Mass Spectrometry. Analytical Chemistry 2014, 86 (11), 5376-5382. https://doi.org/10.1021/ac500383c.
(32) Tsybin et al., Structural Analysis of Intact Monoclonal Antibodies by Electron Transfer Disso-ciation Mass Spectrometry. Anal. Chem. 2011, 83 (23), 8919-8927. https://doi.org/10.1021/ac201293m.
(33) Fornelli et al., Analysis of Intact Monoclonal Antibody IgG1 by Electron Transfer Dissocia-tion Orbitrap FTMS. Mol. Cell. Proteomics 2012, 11 (12), 1758-1767. https://doi.org/10.1074/mcp.M112.019620.
(34) Mao et al., Top-Down Structural Analysis of an Intact Monoclonal Antibody by Electron Capture Dissociation- Fourier Transform Ion Cyclotron Resonance-Mass Spectrometry. Anal. Chem. 2013, 85 (9), 4239-4246. https://doi.org/10.1021/ac303525n.
(35) Fornelli et al., Accurate Sequence Analysis of a Monoclonal Antibody by Top-Down and Middle-Down Orbitrap Mass Spectrometry Applying Multiple Ion Activation Techniques. Anal. Chem. 2018, 90 (14), 8421-8429. https://doi.org/10.1021/acs.analchem.8b00984.
(36) Shaw et al., Sequencing Grade Tandem Mass Spectrometry for Top-Down Proteomics Using Hybrid Electron Capture Dissociation Methods in a Benchtop Orbitrap Mass Spectrometer. Anal. Chem. 2018, 90 (18), 10819-10827. https://doi.org/10.1021/acs.analchem.8b01901.
(37) Liu, H.; May, K. Disulfide Bond Structures of IgG Molecules: Structural Variations, Chemical Modifications and Possible Impacts to Stability and Biological Function. mAbs 2012, 4 (1), 17-23. https://doi.org/10.4161/mabs.4.1.18347.
(38) Fort, et al., Expanding the Structural Analysis Capabilities on an Orbitrap-Based Mass Spectrometer for Large Macromolecular Complexes. Analyst 2018, 143 (1), 100-105. https://doi.org/10.1039/C7AN01629H.
(39) Savitski et al., Proteomics-Grade de Novo Sequencing Approach. J. Proteome Res. 2005, 4 (6), 2348-2354. https://doi.org/10.1021/pr050288x.
(40) Horton et al., Comprehensive de Novo Peptide Sequencing from MS/MS Pairs Generated through Complementary Collision Induced Dissociation and 351 Nm Ultravio-let Photodissociation. Anal. Chem. 2017, 89 (6), 3747-3753. https://doi.org/10.1021/acs.analchem.7b00130.

In view of the many possible embodiments to which the principles of the disclosure may be applied, it should be recognized that the illustrated embodiments are only examples of the invention and should not be taken as limiting the scope of the invention. Rather, the scope of the invention is defined by the following claims. I therefore claim as my invention all that comes within the scope and spirit of these claims.

I claim:

1. A method of determining chain pairing of an intact antibody, comprising:
   ionizing the intact antibody into precursor ions;
   determining a mass of the intact antibody from a mass spectrum of the precursor ions;
   selecting one or more precursor ions for MS/MS analysis;
   dissociating by a first dissociation method, a light chain of the intact antibody from a heavy chain of the intact antibody to generate a first type of product ions of the light chain and produce a first mass spectrum of the light chain;
   dissociating by a second dissociation method, the light chain of the intact antibody from the heavy chain of the intact antibody to generate a second type of product ions of the light chain and produce a second mass spectrum of the light chain, wherein the first dissociation method cleaves a backbone of the light chain at a different location than the second dissociation method;
   comparing the first mass spectrum to the second mass spectrum to identify a first group of the first type of product ions that differ in mass from a second group of the second type of product ions by a constant value;
   determining an amino acid sequence of the light chain based on a mass difference between consecutive product ions of the first group and/or consecutive product ions of the second group;
   determining a mass of the light chain from the first or second mass spectrum;
   determining a mass of the heavy chain of the intact antibody based on the mass of the intact antibody and the mass of the light chain;
   comparing the determined sequence of the light chain and the mass of the heavy chain with a database comprising amino acid sequences of light chain sequences and heavy chain sequences; and
   determining heavy chain and light chain pairing of the intact antibody or antibody fragment.

2. The method of claim 1, wherein the method further comprises enzymatically cleaving the intact antibody at or near the hinge with a hinge cleavage enzyme, to generate one or more antibody fragments.

3. The method of claim 1, wherein the intact antibody is an IgG or IgA.

4. The method of claim 3, wherein the IgG antibody is IgG1.

5. The method of claim 1, further comprising prior to ionizing the intact antibody, separating the intact antibody into individual intact antibody populations.

6. The method of claim 5, wherein the separating is by mass, total charge, or hydrophobicity of the intact antibody or antibody fragment.

7. The method of claim 5, further comprising following the separating, eluting the individual intact antibody populations or antibody fragment populations into separate fractions.

8. The method of claim 1, wherein the first dissociation method comprises ultraviolet photodissociation (UVPD) and the first type of product ions are a-ions, and the second dissociation method comprises electron capture dissociation (ECD) and the second type of product ions are c-ions, and the constant value is 45.0215.

9. The method of claim 1, wherein
   the first type of product ions are a-ions, and the second type of product ions are c-ions, and the constant value is 45.0215
   the first type of product ions are a-ions, and the second type of product ions are b-ions, and the constant value is 27.99495, or
   the first type of product ions are c-ions, and the second type of product ions are b-ions, and the constant value is 17.0267.

10. The method of claim 1, wherein the ionizing comprises electrospray ionization (ESI).

11. The method of claim 10, wherein determining a mass of the intact antibody from a mass spectrum of the precursor ions comprises determining an m/z value of a precursor ion having a +1 charge state.

12. The method of claim 1, wherein selecting one or more precursor ions for MS/MS analysis comprises selecting a most abundant precursor ion for MS/MS analysis.

13. The method of claim 1, further comprising determining a mass of an intact heavy chain from the intact antibody.

14. The method of claim 1, wherein the intact antibody comprises a plurality of intact antibodies or a plurality of antibody fragments.

15. The method of claim 1, further comprising,
   comparing the identified mass of the light chain with a calculated theoretical mass of each light chain sequence of a database comprising a plurality of light chain sequences, and selecting a candidate light chain having the calculated theoretical mass within a threshold error of the identified mass of the light chain; and comparing the identified mass of the heavy chain with a calculated theoretical mass of each heavy chain sequence of a database comprising a plurality of heavy chain sequences, and selecting a candidate heavy chain having the calculated theoretical mass within a threshold error of the identified mass of the Fd portion.

16. The method of claim 1, wherein the intact antibody or antibody fragment is selected for an antigen, the method further comprising, generating a monoclonal antibody selected for the antigen, wherein the monoclonal antibody comprises a light chain corresponding to the candidate light chain sequence and a heavy chain corresponding to the candidate heavy chain sequence.

17. A method of determining chain pairing of an antibody fragment, comprising:
   ionizing the antibody fragment into precursor ions;
   determining a mass of the antibody fragment from a mass spectrum of the precursor ions;
   selecting one or more precursor ions for MS/MS analysis;
   dissociating by a first dissociation method, a light chain of the antibody fragment from an Fd portion of the antibody fragment to generate a first type of product ions of the light chain and a first mass spectrum of the light chain, and a first type of product ions of the Fd portion and a first mass spectrum of the Fd portion, wherein the Fd portion is derived from a heavy chain;
   dissociating by a second dissociation method, the light chain of the antibody fragment from the Fd portion of the antibody fragment to generate a second type of product ions of the LC chain and a second mass spectrum of the LC chain, and a second type of product ions of the Fd portion and a second mass spectrum of the Fd portion, wherein the first dissociation method cleaves a backbone of the Fd portion at a different location than the second dissociation method;
   comparing the first mass spectrum of the light chain to the second mass spectrum of the light chain to identify a first group of the first type of product ions that differ in mass from a second group of the second type of product ions by a constant value;
   comparing the first mass spectrum of the Fd portion to the second mass spectrum of the Fd portion to identify a first group of the first type of product ions that differ in mass from a second group of the second type of product ions by a constant value;
   determining, from the first and/or second mass spectrum of the light chain, an amino acid sequence of the light chain based on a mass difference between consecutive product ions of the first group and/or consecutive product ions of the second group;
   determining an amino acid sequence of the light chain based on a mass difference between consecutive product ions of the first group and/or consecutive product ions of the second group;
   determining, from the first and/or second mass spectrum of the Fd portion, an amino acid sequence of the Fd portion based on a mass difference between consecutive product ions of the first group and/or consecutive product ions of the second group;
   determining an amino acid sequence of the Fd portion based on a mass difference between consecutive product ions of the first group and/or consecutive product ions of the second group;
   comparing the determined sequence of the light chain and Fd portion with a database comprising amino acid sequences of light chain sequences and heavy chain sequences; and
   determining heavy chain and light chain pairing of the antibody fragment.

18. The method of claim 17, wherein the antibody fragment comprises Fab, F(ab')$_2$, or both.

19. The method claim 2, wherein the dissociation method comprises electron capture dissociation (ECD), electron transfer dissociation (ETD), electron detachment dissociation (EDD), or ultraviolet photodissociation (UVPD).

20. The method of claim 2, further comprising,
   comparing the identified mass of the light chain with a calculated theoretical mass of each light chain sequence of a database comprising a plurality of light chain sequences, and selecting a candidate light chain having the calculated theoretical mass within a threshold error of the identified mass of the light chain; and
   comparing the identified mass of the Fd portion with a calculated theoretical mass of an Fd portion of each heavy chain sequence of a database comprising a plurality of heavy chain sequences, and selecting a candidate heavy chain having the calculated theoretical mass within a threshold error of the identified mass of the Fd portion.

21. A method of determining chain pairing in an intact antibody or antibody fragment, comprising:
   ionizing the intact antibody or antibody fragment into precursor ions;
   determining a mass of the intact antibody or a mass of the antibody fragment from a mass spectroscopy spectrum of the precursor ions;
   selecting one or more precursor ions for MS/MS analysis;
   dissociating at least a light chain from the intact antibody by cleaving one or more disulfide bonds linking a heavy chain and the light chain of the intact antibody, or dissociating an intact light chain and a heavy chain fragment from the antibody fragment by cleaving disulfide bonds linking the heavy chain fragment and the light chain of the antibody fragment;
   determining a mass of the light chain of the intact antibody from a mass spectroscopy spectrum of a product ion of the light chain of the intact antibody, or determining a mass of the light chain of the antibody fragment from a mass spectroscopy spectrum of a product ion of the light chain of the antibody fragment and determining a mass of the heavy chain fragment from a mass spectroscopy spectrum of a product ion of the heavy chain fragment of the antibody fragment;
   comparing the identified mass of the light chain and the mass of the intact antibody with a database comprising amino acid sequences of light chain sequences and heavy chain sequences or comparing the identified mass of the light chain and the mass of the heavy chain fragment with a database comprising amino acid sequences of light chain sequences and heavy chain sequences; and
   determining heavy chain and light chain pairing of the intact antibody or antibody fragment.

* * * * *